United States Patent
Takeuchi et al.

(10) Patent No.: US 12,240,871 B2
(45) Date of Patent: Mar. 4, 2025

(54) METHOD FOR PRODUCING PEPTIDE COMPOUND

(71) Applicants: NISSAN CHEMICAL CORPORATION, Tokyo (JP); PeptiDream Inc., Kawasaki (JP)

(72) Inventors: Hisayuki Takeuchi, Funabashi (JP); Yukio Asaka, Funabashi (JP); Akihiro Nagaya, Funabashi (JP); Michiharu Handa, Funabashi (JP); Keiichi Masuya, Kawasaki (JP); Tomonori Taguri, Kawasaki (JP); Yoshitaka Nemoto, Kawasaki (JP); Yutaka Kobayashi, Kawasaki (JP); Ayumu Matsuda, Kawasaki (JP); Haruaki Kurasaki, Kawasaki (JP); Douglas Robert Cary, Kawasaki (JP)

(73) Assignees: Nissan Chemical Corporation, Tokyo (JP); PeptiDream Inc., Kawasaki (JP)

( * ) Notice: Subject to any disclaimer, the term of this patent is extended or adjusted under 35 U.S.C. 154(b) by 63 days.

(21) Appl. No.: 17/439,601

(22) PCT Filed: Mar. 16, 2020

(86) PCT No.: PCT/JP2020/011420
§ 371 (c)(1),
(2) Date: Sep. 15, 2021

(87) PCT Pub. No.: WO2020/189621
PCT Pub. Date: Sep. 24, 2020

(65) Prior Publication Data
US 2022/0153777 A1 May 19, 2022

(30) Foreign Application Priority Data
Mar. 15, 2019 (JP) .................................. 2019-048930

(51) Int. Cl.
*C07K 1/08* (2006.01)
*C07C 69/96* (2006.01)

(52) U.S. Cl.
CPC ................ *C07K 1/08* (2013.01); *C07C 69/96* (2013.01)

(58) Field of Classification Search
CPC ...... C07K 1/08; C07K 5/0202; C07K 5/0205; C07K 5/06026; C07K 5/06034; C07K 5/06052; C07K 5/0606; C07K 5/06078; C07K 5/06147; C07K 5/0806; C07K 5/0812; C07K 5/0817; C07K 5/1016; C07K 5/1021; C07K 5/1024; C07K 7/06; C07K 1/02; C07C 69/96; Y02P 20/55
See application file for complete search history.

(56) References Cited

U.S. PATENT DOCUMENTS

| 5,739,104 | A | 4/1998 | Cooper et al. |
| 2010/0280221 | A1* | 11/2010 | Callens ................ C07K 5/0819 530/331 |
| 2010/0298537 | A1 | 11/2010 | Callens et al. |
| 2012/0107902 | A1 | 5/2012 | Liebeskind et al. |
| 2013/0345423 | A1 | 12/2013 | Kershen et al. |

FOREIGN PATENT DOCUMENTS

| JP | 01313476 A | * 12/1989 |
| JP | 2011-503223 A | 1/2011 |
| JP | 2011-504175 A | 2/2011 |
| JP | 2013-028536 A | 2/2013 |
| JP | 2014-513663 A | 6/2014 |
| WO | WO 2009/134405 A2 | 11/2009 |

OTHER PUBLICATIONS

Kawase et al, Journal of Oleo Science, 59, (4) 191-201 (2010) (Year: 2010).*
Kahns et al, International, Journal of Pharmaceutics, 71 (1991) 31-43 (Year: 1991).*
Bibi et al., "Design and Comparative Evaluation of the Anticonvulsant Profile, Carbonic-Anhydrate Inhibition and Teratogenicity of Novel Carbamate Derivatives of Branched Aliphatic Carboxylic Acids with 4-Aminobenzensulfonamide," *Neurochemical Res.*, 42(7): 1972-1982 (2017).
Ryakhovsky et al., "Study of intramolecular aminolysis in peptides containing N-alkylamino acids at position 2," *Tetrahedron*, 68(35): 7070-7076 (2012).
Tantry et al., "Synthesis of $N^\alpha$-protected peptide acids by the N→C chain extension employing O,N-bis-trimethylsilyl-amino acids using the mixed anhydride method," *Indian Journal of Chemistry*, 43B: 1282-1287 (2004).
Japanese Patent Office, International Search Report in International Patent Application No. PCT/JP2020/011420 (Jun. 9, 2020).
European Patent Office, Extended European Search Report in European Patent Application No. 20773236.3 (Oct. 24, 2022).
Nagano et al., "Specialty Peptide Drug Discovery That Opens Up the Future," *Pharmacia*, 50(8): 751-755 (2014).

* cited by examiner

*Primary Examiner* — Sudhakar Katakam
(74) *Attorney, Agent, or Firm* — Leydig, Voit & Mayer, Ltd.

(57) ABSTRACT

The present invention is to provide a method for producing a peptide containing an N-alkylamino acid, which comprises the following Steps (1) to (3). Step (1): a step of mixing an N-terminal protected amino acid or an N-terminal protected peptide with a carboxylic acid halide or a halogenated alkyl formate; Step (2): a step of mixing an amino acid or a peptide in which the N-terminal and the C-terminal are not protected with a trialkylsilylating agent; and Step (3): a step of mixing the product obtained in Step (1) with the product obtained in Step (2).

20 Claims, No Drawings

METHOD FOR PRODUCING PEPTIDE COMPOUND

TECHNICAL FIELD

The present invention relates to a method for producing a peptide having an N-alkylamino acid.

BACKGROUND ART

In recent years, as a next-generation drug in place of protein pharmaceuticals, expectations are increasing for unique peptides having a relatively low molecular weight (1,000-3,000) and containing unnatural amino acids. Examples of the unique peptides may be mentioned peptides containing N-alkylamino acids other than natural amino acids. The peptides containing N-alkylamino acids have the characteristics that, as compared with natural peptides, they have restricted conformation and can bind strongly to the targets, have membrane permeability, have low immunogenicity, and are stable in vivo. Thus, it has been strongly desired to develop an efficient method for producing a peptide containing an N-alkylamino acid (for example, see Non-Patent Document 1).

As a method for producing a peptide containing an N-alkylamino acid, there have been known, for example, the following methods.

(1) A peptide in which the C-terminal of the product is protected
  A method in which the C-terminal of an N-terminal protected amino acid is activated with pivaloyl chloride, and a benzyl ester of an N-methylamino acid is reacted therewith (for example, see Patent Document 1).

(2) A peptide in which the C-terminal the product is unprotected
  A method in which the C-terminal of an N-terminal protected amino acid is activated with isobutylchloroformate, and silylated N-methylglycine (sarcosine) or proline is reacted therewith (for example, see Non-Patent Document 2).
  A method in which the C-terminal of an N-terminal protected peptide is activated with 1-[bis(dimethylamino)methylene]-1H-1,2,3-triazolo[4,5-b]pyridinium 3-oxide hexafluorophosphate (HATU), and an N-methylalanine is reacted therewith (for example, see Patent Document 2).

Also, as a method for producing a peptide in which N-methylamino acids are continued, it has been known a method in which the C-terminal of N-Boc-N-methyl-leucine is activated by pivaloyl chloride and N-methylphenylalanine methyl ester is reacted therewith (for example, see Non-Patent Document 3).

PRIOR ART DOCUMENTS

Patent Documents

Patent Document 1: U.S. Pat. No. 5,739,104
Patent Document 2: WO 2009/134405

Non-Patent Documents

Non-Patent Document 1: Pharmacia 2014, vol. 50, pp. 751-755
Non-Patent Document 2: Indian Journal of Chemistry 2004, vol. 43B. p. 1282
Non-Patent Document 3: Tetrahedron 2012, vol. 68, p. 7070

SUMMARY OF THE INVENTION

Problems to be Solved by the Invention

When the present inventors have confirmed, using the method described in Non-Patent Document 2, when an amino acid having an alkyl group at the N-terminal is introduced into the C-terminal of an amino acid in which the N-terminal is protected, the reaction does not always proceed at a sufficient conversion rate depending on the type of the amino acid to be introduced, in particular, in an acyclic N-alkylamino acid such as N-methylglycine or in a peptide, a large amount of the starting material remains so that the objective product cannot be obtained with a satisfactory yield. Residual of the raw material becomes a cause of forming a peptide which lacks some amino acids, which is difficultly removed since the physical properties thereof are close to those of the objective peptide, whereby it poses a problem in quality. Also, the method described in Patent Document 2 uses HATU containing a triazole structure which has explosive property as a condensing agent, and it cannot necessarily be applied to the industrial production of a peptide.

On the other hand, in the methods described in Patent Document 1 and Non-Patent Document 3, the C-terminal of the peptide to be produced is protected, and for obtaining a peptide in which the C-terminal is unprotected, it is necessary to further carry out a deprotection step. Accordingly, a deprotection step was necessarily required in addition to the condensation step so that it could not be applied as an efficient producing method of a peptide.

The present invention is to provide a method for producing a peptide which contains an N-alkylamino acid(s) and the C-terminal of which is unprotected. Also, the present invention is to provide a method for producing a peptide using an amino acid or a peptide which contains an N-alkyl group and the N-terminal and the C-terminal of which is not protected and an N-terminal protected amino acid or peptide as materials.

Means to Solve the Problems

The present inventors have intensively studied, and as a result, they have found that the above-mentioned problems can be solved by mixing an unprotected amino acid or peptide which contains an N-alkyl group and the N-terminal and the C-terminal of which are not protected with a silylating agent, and further mixing an N-terminal protected amino acid or peptide with a carboxylic acid activating agent having a specific structure, whereby the present invention has accomplished. That is, the present invention has the following characteristics.

[1] A method for producing a peptide which comprises the following Steps (1) to (3):

(1) a step of mixing an N-terminal protected amino acid or an N-terminal protected peptide represented by the formula (I): P-A$^1$-OH (wherein P is an N-terminal protective group, and A$^1$ represents a group derived from an amino acid, a group derived from an N—C$_{1-6}$ alkylamino acid (the C$_{1-6}$ alkyl may have a substituent(s)) or a group derived from a peptide)
with an activating agent selected from the group consisting of a carboxylic acid halide represented by the formula (II):

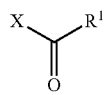

(wherein X represents a halogen atom, and $R^1$ represents a secondary or tertiary aliphatic hydrocarbon group having 5 or more carbon atoms which may have a substituent(s), or a primary aliphatic hydrocarbon group having 4 or more carbon atoms which have a substituent(s) (here, the substituent(s) on the primary aliphatic hydrocarbon group exists on the carbon atom bonded to the carbonyl carbon)), and a halogenated alkyl formate represented by the formula (III):

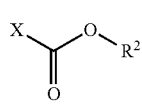

(wherein X represents a halogen atom, and $R^2$ represents a secondary aliphatic hydrocarbon group having 5 or more carbon atoms which may have a substituent(s));
(2) a step of mixing an amino acid or a peptide represented by
the formula (IV): H-$A^2$-OH (wherein $A^2$ represents a group derived from an N—$C_{1-6}$ alkylamino acid (the $C_{1-6}$ alkyl may have a substituent(s)), or a group derived from a 4- to 6-membered cyclic secondary amino acid (the 4- to 6-membered ring may be fused with a cyclic compound selected from the group consisting of a $C_{6-14}$ aryl ring, a $C_{6-14}$ haloaryl ring and a $C_{3-8}$ cycloalkyl ring), or a group derived from a peptide in which the N-terminal residue is an N—$C_{1-6}$ alkylamino acid (the $C_{1-6}$ alkyl may have a substituent(s)) or a 4- to 6-membered cyclic secondary amino acid (the 4- to 6-membered ring may be fused with a cyclic compound selected from the group consisting of a $C_{6-14}$ aryl ring, a $C_{6-14}$ haloaryl ring and a $C_{3-8}$ cycloalkyl ring)) with a silylating agent; and
(3) a step of mixing a product obtained in Step (1) and a product obtained in Step (2).
[2] A method for producing a peptide which comprises the following Steps (1) to (3):
(1) a step of mixing an N-terminal protected amino acid represented by the formula (I): P-$A^1$-OH (wherein P is an N-terminal protective group, and $A^1$ represents a group derived from an amino acid or a group derived from an N—$C_{1-6}$ alkylamino acid (the $C_{1-6}$ alkyl may have a substituent(s)))
with an activating agent selected from the group consisting of a carboxylic acid halide represented by the formula (II):

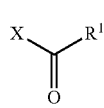

(wherein X represents a halogen atom, and $R^1$ represents a secondary or tertiary aliphatic hydrocarbon group having 5 or more carbon atoms which may have a substituent(s), or a primary aliphatic hydrocarbon group having 4 or more carbon atoms which have a substituent(s) (here, the substituent(s) on the primary aliphatic hydrocarbon group exists on the carbon atom bonded to the carbonyl carbon)) and a halogenated alkyl formate represented by the formula (III):

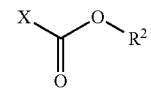

(wherein X represents a halogen atom, and $R^2$ represents a secondary aliphatic hydrocarbon group having 5 or more carbon atoms which may have a substituent(s));
(2) a step of mixing an amino acid or a peptide represented by the formula (IV): H-$A^2$-OH (wherein $A^2$ represents a group derived from an N-methylamino acid, a group derived from an N—$C_{1-6}$ alkylglycine (the $C_{1-6}$ alkyl may have a substituent(s)), or a group derived from a 4- to 6-membered cyclic secondary amino acid, or a group derived from a peptide in which the N-terminal residue is an N-methylamino acid, an N—$C_{1-6}$ alkylglycine (the $C_{1-6}$ alkyl may have a substituent(s)), or a 4- to 6-membered cyclic secondary amino acid) with a silylating agent; and
(3) a step of mixing a product obtained in Step (1) and a product obtained in Step (2).
[3] A method for producing a peptide which comprises the following Steps (1) to (3):
(1) a step of mixing an N-terminal protected peptide represented by the formula (V): P-$A^3$-OH (wherein P is an N-terminal protective group, and $A^3$ represents a group derived from a peptide)
with a carboxylic acid halide represented by the formula (II):

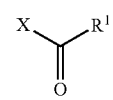

(wherein X represents a halogen atom, and $R^1$ represents a secondary or tertiary aliphatic hydrocarbon group having 5 or more carbon atoms which may have a substituent(s), or a primary aliphatic hydrocarbon group having 4 or more carbon atoms which have a substituent(s) (here, the substituent(s) on the primary aliphatic hydrocarbon group exists on the carbon atom bonded to the carbonyl carbon));
(2) a step of mixing an amino acid represented by the formula (IV'): H-$A^{2'}$-OH (wherein $A^{2'}$ represents a group derived from an N-methylamino acid, a group derived from an N—$C_{1-6}$ alkylglycine (the $C_{1-6}$ alkyl may have a substituent(s)), or a group derived from a 4- to 6-membered cyclic secondary amino acid) with a silylating agent;
(3) a step of mixing a product obtained in Step (1) and a product obtained in Step (2).
[4] The method for producing a peptide described in any of the above-mentioned [1] to [3], which comprises a step of removing the protective group of the N-terminal of the peptide obtained in Step (3).
[5] The method for producing a peptide described in any of the above-mentioned [1] to [3], which further comprises repeating one or more times of the following Steps (4) and (5):
(4) a step of removing the protective group of the N-terminal of the peptide obtained in Step (3) or (5);

(5) a step of reacting an N-terminal protected amino acid or an N-terminal protected peptide with the N-terminal of the peptide obtained in Step (4).

[6] The method for producing a peptide described in the above-mentioned [1] or [3], wherein the amino acid positioned at the C-terminal in the N-terminal protected peptide represented by the formula (I): P-A$^1$-OH or the formula (V): P-A$^3$-OH (wherein P is an N-terminal protective group, and A$^1$ and A$^3$ each represent a group derived from a peptide) is an amino acid other than the N—C$_{1-6}$ alkylamino acid (the C$_{1-6}$ alkyl may have a substituent(s)) or a 4- to 6-membered cyclic secondary amino acid (the 4- to 6-membered ring may be fused with a cyclic compound selected from the group consisting of a C$_{6-14}$ aryl ring, a C$_{6-14}$ haloaryl ring and a C$_{3-8}$ cycloalkyl ring).

[7] The method for producing a peptide described in the above-mentioned [1] or [2], wherein A$^1$ is a group derived from an amino acid.

[8] The method for producing a peptide described in the above-mentioned [1] or [2], wherein the N-terminal protected amino acid represented by the formula (I) or the amino acid positioned at the C-terminal in the N-terminal protected peptide represented by the formula (I) is an α-amino acid, a β-amino acid or a γ-amino acid.

[9] The method for producing a peptide described in the above-mentioned [8], wherein the N-terminal protected amino acid represented by the formula (I) or the amino acid positioned at the C-terminal in the N-terminal protected peptide represented by the formula (I) is an α-amino acid.

[10] The method for producing a peptide described in the above-mentioned [1], wherein the amino acid represented by the formula (IV) or the amino acid positioned at the N-terminal in the peptide represented by the formula (IV) is an N—C$_{1-6}$ alkyl-α-amino acid (the C$_{1-6}$ alkyl may have a substituent(s)) or a 4- to 6-membered cyclic secondary-α-amino acid.

[11] The method for producing a peptide described in the above-mentioned [1], wherein the amino acid represented by the formula (IV) or the amino acid positioned at the N-terminal in the peptide represented by the formula (IV) is an N-methyl-α-amino acid or an N-ethyl-α-amino acid (N-methyl and N-ethyl each may have a substituent(s)), or a 4- to 6-membered cyclic secondary-α-amino acid.

[12] The method for producing a peptide described in any one of the above-mentioned [1] to [11], wherein the activating agent is a carboxylic acid halide represented by the formula (II), R$^1$ has 5 to 20 carbon atoms, and X is a chlorine atom.

[13] The method for producing a peptide described in any one of the above-mentioned [1] to [12], wherein the activating agent is a carboxylic acid halide represented by the formula (II), and is selected from the following compound group.

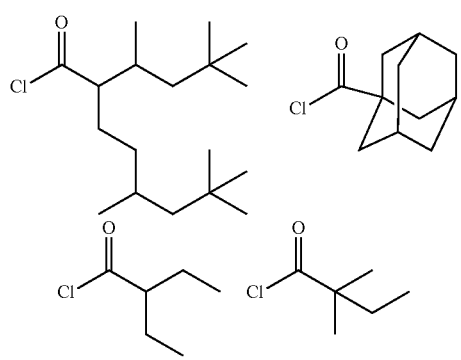

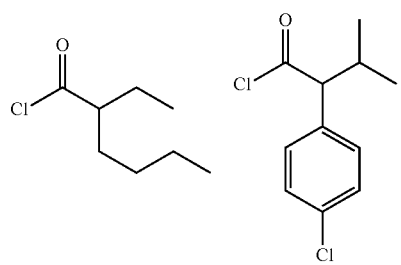

[14] The method for producing a peptide described in any one of the above-mentioned [1] to [12], wherein the activating agent is a carboxylic acid halide represented by the formula (II), and is selected from the following compound group.

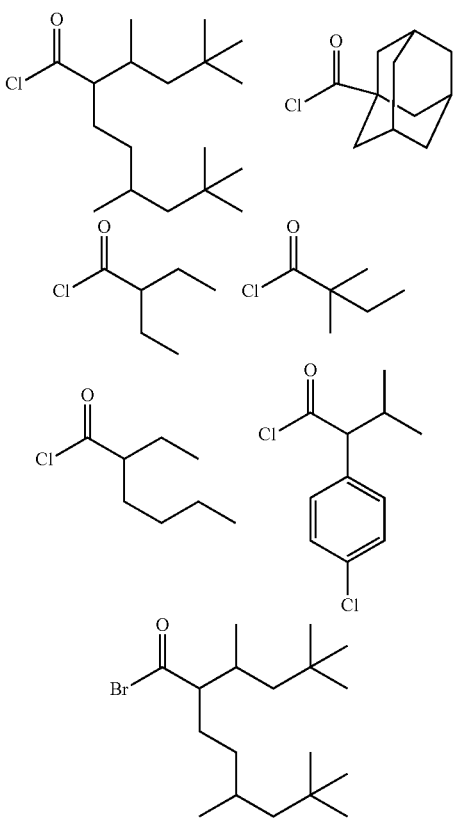

[15] The method for producing a peptide described in the above-mentioned [13] or [14], wherein the activating agent is the following compound.

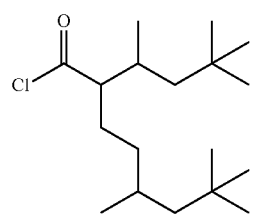 [SMILES: CC(CCC(C(=O)Cl)C(C)CC(C)(C)C)CC(C)(C)C]

[16] The method for producing a peptide described in the above-mentioned [1] or [2], wherein the activating agent is a halogenated alkyl formate represented by the formula (III), and X is a chlorine atom.

[17] The method for producing a peptide described in the above-mentioned [1] or [2], wherein the activating agent is a halogenated alkyl formate represented by the formula (III), and is selected from the following compound group.

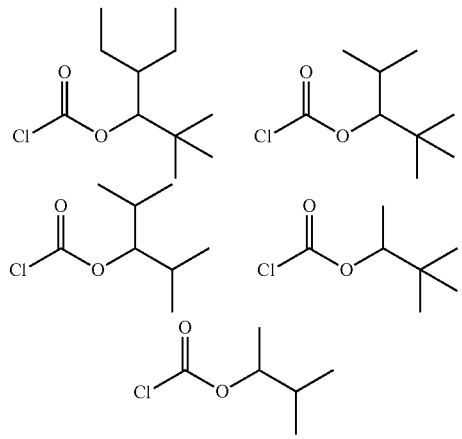

[18] The method for producing a peptide described in the above-mentioned [1] or [2], wherein the activating agent is a halogenated alkyl formate represented by the formula (III), and is selected from the following compound group.

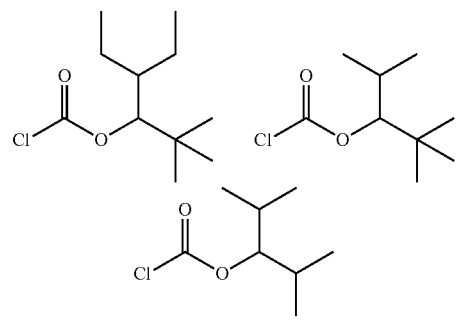

[19] The method for producing a peptide described in any one of the above-mentioned [1] to [18], wherein the silylating agent is a trimethylsilylating agent.

[20] The method for producing a peptide described in any one of the above-mentioned [1] to [19], wherein the silylating agent is N,O-bis(trimethylsilyl)acetamide, N,N'-bis(trimethylsilyl)urea or N,O-bis(trimethylsilyl)trifluoroacetamide.

[21] The method for producing a peptide described in any one of the above-mentioned [1] to [20], wherein the silylating agent is N,O-bis(trimethylsilyl)acetamide.

[22] The method for producing a peptide described in the above-mentioned [1], wherein the amino acid or peptide represented by the formula (IV) are each an amino acid other than proline or a peptide in which the N-terminal residue is an amino acid residue other than proline.

[23] The method for producing a peptide described in the above-mentioned [3], wherein the amino acid represented by the formula (IV') is an amino acid other than proline.

[24] A compound represented by the following formula:

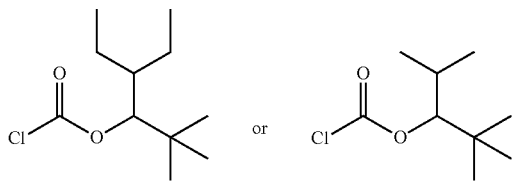

Effects of the Invention

According to the present invention, it could be provided a novel method for producing a peptide in which the C-terminal is unprotected by using an amino acid or a peptide containing an N-alkyl group and the N-terminal and the C-terminal are not protected and an N-terminal protected amino acid or peptide are used as materials. According to the producing method of the present invention, the objective peptide can be obtained with a satisfactory yield by using an industrially applicable reagent, with a small number of steps, and regardless of the type of an N-alkylamino acid to be introduced, and further regardless of the type of an N-alkylamino acid at the N-terminal residue of a peptide to be introduced.

EMBODIMENTS TO CARRY OUT THE INVENTION

Hereinafter, the present invention will be explained in detail.

In the present specification, "n-" means normal, "s-" means secondary, "t-" and "tert-" mean tertiary, "Me" means methyl, "Et" means ethyl, "Pr" means propyl, "Bu" means butyl, "Ph" means phenyl, "Bn" means benzyl, "Boc" means t-butoxycarbonyl, "Cbz" means benzyloxycarbonyl, "Fmoc" means 9-fluorenylmethoxycarbonyl, "Trt" means trityl, "TMS" means trimethylsilyl, and "TFA" means trifluoroacetic acid.

The terms "halogen atom" mean a fluorine atom, a chlorine atom, a bromine atom or an iodine atom.

In the present invention, the terms "alkyl group" mean a linear or branched, monovalent group of a saturated aliphatic hydrocarbon. The terms "$C_{1-6}$ alkyl group" mean a linear or branched alkyl group having 1 to 6 carbon atoms, and specific examples thereof may be mentioned a methyl group, an ethyl group, an n-propyl group, an isopropyl group, an n-butyl group, an isobutyl group, an s-butyl group, a t-butyl group, an n-pentyl group, a 3-pentyl group, a 2-methylbutyl group, a 3-methylbutyl group, a 1,1-dimethylpropyl group, a 1,2-dimethylpropyl group, a 2,2-dimethylpropyl group, a 1-ethylpropyl group, an n-hexyl group, a 3,3-dimethylbutan-2-yl group, etc.

The terms "secondary or tertiary $C_{5-40}$ alkyl group" mean a monovalent group in which hydrogen on a secondary or tertiary carbon atom is removed from a saturated aliphatic hydrocarbon having 5 to 40 carbon atoms and containing at least one secondary or tertiary carbon atom, and specific examples thereof may be mentioned a 2-methylbutan-2-yl group, a 3-methylbutan-2-yl group, a 3,3-dimethylbutan-2-yl group, a 3-pentyl group, a 2,2,4-trimethylpentan-3-yl group, a 2,4-dimethylpentan-3-yl group, a 4-ethyl-2,2-dimethylhexan-3-yl group, a 3-heptyl group, a 2,2,4,8,10,10-hexamethyl-undecan-5-yl group, etc. Also, the terms "secondary or tertiary $C_{5-20}$ alkyl group" mean a secondary or tertiary alkyl group having 5 to 20 carbon atoms.

The terms "primary $C_{4-40}$ alkyl group" mean a monovalent group in which hydrogen on a primary carbon atom is removed from a linear or branched, saturated aliphatic hydrocarbon having 4 to 40 carbon atoms, and there may be mentioned an n-butyl group, an isobutyl group, an n-pentyl group, a 2-methylbutyl group, a 3-methylbutyl group, an n-hexyl group, an n-heptyl group, an n-octyl group, an n-nonyl group, an n-decyl group, an n-dodecyl group, an n-icosyl group, an n-triacontyl group, an n-tetracontyl group or a primary alkyl group which is an isomer thereof, etc. Also, the terms "primary $C_{4-20}$ alkyl group" mean a primary alkyl group having 4 to 20 carbon atoms.

In the present invention, the terms "alkenyl group" mean a linear or branched, monovalent group of an unsaturated aliphatic hydrocarbon containing at least one carbon-carbon double bond. The terms "secondary or tertiary alkenyl group" mean a monovalent group in which a hydrogen on a secondary or tertiary carbon atom is removed from at least one secondary or tertiary carbon atom, and an unsaturated aliphatic hydrocarbon containing at least one carbon-carbon double bond, and specific examples thereof may be mentioned an isopropenyl group, a 1-methyl-1-propenyl group, etc. Also, the terms "secondary or tertiary $C_{5-40}$ alkenyl group" mean a secondary or tertiary alkenyl group having 5 to 40 carbon atoms, and the terms "secondary or tertiary $C_{5-20}$ alkenyl group" mean those having 5 to 20 carbon atoms.

The terms "primary $C_{4-40}$ alkenyl group" mean a monovalent group in which a hydrogen on a primary carbon atom is removed from a linear or branched unsaturated aliphatic hydrocarbon having 4 to 40 carbon atoms and containing at least one carbon-carbon double bond, and may be mentioned a 2-butenyl group, a 3-butenyl group, a 2-pentenyl group, etc. Also, the terms "primary $C_{4-20}$ alkenyl group" mean a primary alkenyl group having 4 to 20 carbon atoms.

The terms "$C_{6-14}$ aryl group" mean an aromatic hydrocarbon group having 6 to 14 carbon atoms, and specific examples thereof may be mentioned a phenyl group, a 1-naphthyl group, a 2-naphthyl group, a 1-anthryl group, a 2-anthryl group, a 9-anthryl group, a biphenyl group, etc. Also, the terms "$C_{6-14}$ aryl ring" mean an aromatic hydrocarbon ring having 6 to 14 carbon atoms.

The terms "$C_{6-14}$ haloaryl group" mean an aromatic hydrocarbon group having 6 to 14 carbon atoms which is substituted by one or more halogen atoms, and specific examples thereof may be mentioned a 4-chlorophenyl group, a 2,4-dichlorophenyl group, a 5-fluoro-1-naphthyl group, a 6-bromo-2-naphthyl group, a 6,7-diiodo-1-anthryl group, a 10-bromo-9-anthryl group, a 4'-chloro-(1,1'-biphenyl)-2-yl group, etc. The terms "$C_{6-14}$ haloaryl ring" mean an aromatic hydrocarbon ring having 6 to 14 carbon atoms which is substituted by one or more halogen atoms.

The terms "$C_{6-14}$ aryloxy group" mean an aryloxy group having 6 to 14 carbon atoms, and specific examples thereof may be mentioned a phenoxy group, a 1-naphthyloxy group, a 2-naphthyloxy group, a 1-anthryloxy group, a 2-anthryloxy group, a 9-anthryloxy group, a biphenyloxy group, etc.

The terms "5-10-membered heterocyclic group" mean a monocyclic-based or a fused ring-based heterocyclic group having a number of the atoms constituting the ring of 5 to 10, and containing 1 to 4 hetero atoms independently selected from the group consisting of a nitrogen atom, an oxygen atom and a sulfur atom in the atoms constituting the ring. The heterocyclic group may be either of saturated, partially unsaturated or unsaturated, and specific examples thereof may be mentioned a pyrrolidinyl group, a tetrahydrofuryl group, a tetrahydrothienyl group, a piperidyl group, a tetrahydropyranyl group, a tetrahydrothiopyranyl group, a pyrrole group, a furyl group, a thienyl group, a pyridyl group, a pyrimidinyl group, a pyridazinyl group, an azepanyl group, an oxepanyl group, a thiepanyl group, an azepinyl group, an oxepinyl group, a thiepinyl group, an imidazolyl group, a pyrazolyl group, an oxazolyl group, a thiazolyl group, an imidazolinyl group, a pyrazinyl group, a morpholinyl group, a thiazinyl group, an indolyl group, an isoindolyl group, a benzimidazolyl group, a purinyl group, a quinolyl group, an isoquinolyl group, a quinoxalinyl group, a cinnolinyl group, a pteridinyl group, a chromenyl group, an isochromenyl group, etc.

The terms "$C_{1-6}$ alkoxy group" mean a linear or branched alkoxy group having 1 to 6 carbon atoms, and specific examples thereof may be mentioned a methoxy group, an ethoxy group, an n-propoxy group, an isopropoxy group, an n-butoxy group, an isobutoxy group, a t-butoxy group, an n-pentyloxy group, an n-hexyloxy group, etc.

The terms "$C_{3-6}$ cycloalkyl group" mean a monovalent group of a cyclic saturated aliphatic hydrocarbon having 3 to 6 carbon atoms, and specific examples thereof may be mentioned a cyclopropyl group, a cyclobutyl group, a cyclopentyl group, a cyclohexyl group, etc.

The terms "$C_{3-8}$ cycloalkyl group" mean a cycloalkyl group having 3 to 8 carbon atoms, and specific examples thereof may be mentioned, in addition to the examples of the above-mentioned "$C_{3-6}$ cycloalkyl group", a cycloheptyl group, a cyclooctyl group, etc. Also, the terms "$C_{5-8}$ cycloalkyl group" mean a cycloalkyl group having 5 to 8 carbon atoms, and the terms "$C_{5-6}$ cycloalkyl group" mean a cycloalkyl group having 5 to 6 carbon atoms. The terms "$C_{3-8}$ cycloalkyl ring" mean a cycloalkyl ring having 3 to 8 carbon atoms.

The terms "$C_{3-6}$ cyclo alkoxy group" mean a cycloalkyloxy group having 3 to 6 carbon atoms, and specific examples thereof may be mentioned a cyclopropoxy group, a cyclobutoxy group, a cyclopentyloxy group, a cyclohexyloxy group, etc.

The terms "mono-$C_{1-6}$ alkylamino group" mean a group in which one of the above-mentioned "$C_{1-6}$ alkyl group" is bonded to an amino group, and specific examples thereof may be mentioned a monomethylamino group, a monoethylamino group, a mono-n-propylamino group, a monoisopropylamino group, a mono-n-butylamino group, a monoisobutylamino group, a mono-t-butylamino group, a mono-n-pentylamino group, a mono-n-hexylamino group, etc.

The terms "di-$C_{1-6}$ alkylamino group" mean a group in which the same or different two above-mentioned "$C_{1-6}$ alkyl groups" are bonded to an amino group, and specific examples thereof may be mentioned a dimethylamino group, a diethylamino group, a di-n-propylamino group, a diisopropylamino group, a di-n-butylamino group, a diisobutylamino group, a di-t-butylamino group, a di-n-pentylamino group, a di-n-hexylamino group, an N-ethyl-N-methylamino group, an N-methyl-N-n-propylamino group, an N-isopropyl-N-methylamino group, an N-n-butyl-N-methylamino group, an N-isobutyl-N-methylamino group, an N-t-butyl-N-methylamino group, an N-methyl-N-n-pentylamino group, an N-n-hexyl-N-methylamino group, an N-ethyl-N-n-propyl-amino group, an N-ethyl-N-isopropylamino group, an N-n-butyl-N-ethylamino group, an N-ethyl-N-isobutylamino group, an N-t-butyl-N-ethylamino group, an N-ethyl-N-n-pentylamino group, an N-ethyl-N-n-hexylamino group, etc.

The terms "$C_{1-6}$ alkoxycarbonyl group" mean a linear or branched alkoxy-carbonyl group having 1 to 6 carbon atoms, and specific examples thereof may be mentioned a methoxycarbonyl group, an ethoxycarbonyl group, an n-propoxycarbonyl group, an isopropoxycarbonyl group, an n-butoxycarbonyl group, an isobutoxycarbonyl group, a t-butoxycarbonyl group, an n-pentyloxycarbonyl group, an n-hexyloxycarbonyl group, etc.

The terms "tri-$C_{1-6}$ alkylsilyl group" mean a group in which the same or different three above-mentioned "$C_{1-6}$ alkyl groups" are bonded to a silyl group, and specific examples thereof may be mentioned a trimethylsilyl (TMS) group, a triethylsilyl group, a triisopropylsilyl group, a t-butyldimethylsilyl group, a di-t-butylisobutylsilyl group, etc.

The terms "tri-$C_{1-6}$ alkylsilyloxy group" mean a group in which the same or different three above-mentioned "$C_{1-6}$ alkyl groups" are bonded to a silyloxy group, and specific examples thereof may be mentioned a trimethylsilyloxy group, a triethylsilyl-oxy group, a triisopropylsilyloxy group, a t-butyldimethylsilyloxy group, a di-t-butylisobutylsilyloxy group, etc.

The terms "bicycloalkyl group" mean a monovalent group of a saturated aliphatic hydrocarbon containing two bridgehead carbons and having two rings, and specific examples thereof may be mentioned an octahydroinden-3-yl group, an octahydronaphthalen-4-yl group, a bicyclo[2.2.1]heptane-1-yl group or a bicyclo-[2.2.1]heptane-2-yl group, etc. Also, the terms "$C_{5-10}$ bicycloalkyl group" mean a bicycloalkyl group having 5 to 10 carbon atoms, and the terms "$C_{7-10}$ bicycloalkyl group" mean those having 7 to 10 carbon atoms.

The terms "tricycloalkyl group" mean a monovalent group of a saturated aliphatic hydrocarbon containing at least three bridgehead carbons and having three rings, and specific examples thereof may be mentioned a tricyclo[3.3.1.1$^{3.7}$]decan-1-yl(adamanthan-1-yl) group or tricyclo[3.3.1.1$^{3.7}$]decan-2-yl(adamanthan-2-yl) group, etc. Also, the terms "$C_{5-15}$ tricycloalkyl group" mean a tricycloalkyl group having 5 to 15 carbon atoms, and the terms "$C_{7-15}$ tricycloalkyl group" mean a tricycloalkyl group having 7 to 15 carbon atoms.

The terms "secondary or tertiary aliphatic hydrocarbon group" are a monovalent group in which hydrogen on a secondary or tertiary carbon atom is removed from a branched or cyclic saturated or unsaturated aliphatic hydrocarbon containing at least one secondary or tertiary carbon atom in a hydrocarbon chain, and may be mentioned a secondary or tertiary alkyl group, a bicycloalkyl group, a tricycloalkyl group, secondary or tertiary alkenyl group, etc., and specific examples thereof may be mentioned a secondary or tertiary alkyl group, a bicycloalkyl group, a tricycloalkyl group, a secondary or tertiary alkenyl group each having 5 or more carbon atoms, etc., preferably a secondary or tertiary $C_{5-40}$ alkyl group, a $C_{5-10}$ bicycloalkyl group, a $C_{5-15}$ tricycloalkyl group, a secondary or tertiary $C_{5-40}$ alkenyl group, etc., and more preferably a secondary or tertiary $C_{5-20}$ alkyl group, a $C_{7-10}$ bicycloalkyl group, a $C_{7-15}$ tricycloalkyl group, a secondary or tertiary $C_{5-20}$ alkenyl group, etc.

The terms "secondary aliphatic hydrocarbon group" mean a monovalent group in which hydrogen on a secondary carbon atom is removed from a branched or cyclic saturated or unsaturated aliphatic hydrocarbon containing at least one secondary carbon atom on the hydrocarbon chain, and may be mentioned a secondary alkyl group, a cycloalkyl group, a secondary alkenyl group, etc., and specific examples thereof may be mentioned a secondary alkyl group, a cycloalkyl group, a secondary alkenyl group each having 5 or more carbon atoms, etc., preferably mentioned a secondary $C_{5-40}$ alkyl group, a $C_{3-8}$ cycloalkyl group, a secondary $C_{5-40}$ alkenyl group, etc., and more preferably mentioned a secondary $C_{5-20}$ alkyl group, $C_{3-6}$ cycloalkyl group, a secondary $C_{5-20}$ alkenyl group, etc.

The terms "primary aliphatic hydrocarbon group" mean a monovalent group in which hydrogen on a primary carbon atom is removed from a linear or branched saturated or unsaturated aliphatic hydrocarbon, and may be mentioned a primary alkyl group, a primary alkenyl group, etc., and specific examples thereof may be mentioned a primary alkyl group, a primary alkenyl group each having 4 or more carbon atoms, etc., preferably mentioned a primary $C_{4-40}$ alkyl group, a primary $C_{4-40}$ alkenyl group, etc., and more preferably mentioned a primary $C_{4-20}$ alkyl group, a primary $C_{4-20}$ alkenyl group, etc.

The terms "which may have a substituent(s)" mean that it is unsubstituted, or substituted by an optional number of an optional substituent(s).

The terms "having a substituent(s)" mean that it is substituted by an optional number of an optional substituent(s).

With regard to the above-mentioned "optional substituent(s)", the kind thereof is not particularly limited as long as it is a substituent which does not exert any bad effect to the reaction which is the target of the present invention.

The "substituent" in the case that the "$C_{1-6}$ alkyl group may have a substituent(s)" may be mentioned, for example, a $C_{6-14}$ aryl group, a $C_{6-14}$ haloaryl group, a $C_{6-14}$ aryloxy group, a 5- to 10-membered heterocyclic group, a hydroxy group, a $C_{1-6}$ alkoxy group, a $C_{3-6}$ cycloalkoxy group, an acetoxy group, a benzoyloxy group, a mono-$C_{1-6}$ alkylamino group, an N-acetylamino group, a di-$C_{1-6}$ alkylamino group, a halogen atom, a $C_{1-6}$ alkoxycarbonyl group, a phenoxycarbonyl group, an N-methyl-carbamoyl group, an N-phenylcarbamoyl group, a tri-$C_{1-6}$ alkylsilyl group, a tri-$C_{1-6}$ alkylsilyloxy group, a $C_{3-8}$ cycloalkyl group, cyano group, a nitro group, etc., preferably a $C_{6-14}$ aryl group, a $C_{6-14}$ haloaryl group, a $C_{1-6}$ alkoxy group, a di-$C_{1-6}$ alkylamino group, a tri-$C_{1-6}$ alkylsilyl group, a tri-$C_{1-6}$ alkylsilyloxy group and, a $C_{3-8}$ cycloalkyl group, more preferably a $C_{6-14}$ aryl group, a $C_{6-14}$ haloaryl group, a $C_{1-6}$ alkoxy group, a tri-$C_{1-6}$ alkylsilyl group and a $C_{3-8}$ cycloalkyl group, further preferably a $C_{6-14}$ aryl group or a $C_{3-8}$ cycloalkyl group, and particularly preferably a phenyl group or a cyclohexyl group.

The "substituent" in the "secondary or tertiary aliphatic hydrocarbon group which may have a substituent(s)" or the "primary aliphatic hydrocarbon group having a substituent(s)" may be mentioned, for example, a $C_{6-14}$ aryl group, a $C_{6-14}$ haloaryl group, a $C_{6-14}$ aryloxy group, a 5- to 10-membered heterocyclic group, a hydroxy group, a $C_{1-6}$ alkoxy group, a $C_{3-6}$ cyclo alkoxy group, an acetoxy group, a benzoyloxy group, a mono-$C_{1-6}$ alkylamino group, an N-acetylamino group, a di-$C_{1-6}$ alkylamino group, a halogen atom, $C_{1-6}$ alkoxycarbonyl group, a phenoxycarbonyl group, an N-methyl-carbamoyl group, an N-phenylcarbamoyl group, a tri-$C_{1-6}$ alkylsilyl group, a tri-$C_{1-6}$ alkylsilyloxy group, a $C_{3-8}$ cycloalkyl group, cyano group, a nitro group, etc., preferably a $C_{6-14}$ aryl group, a $C_{6-14}$ haloaryl group, a $C_{1-6}$ alkoxy group, a di-$C_{1-6}$ alkylamino group, a tri-$C_{1-6}$ alkylsilyl group, a tri-$C_{1-6}$ alkylsilyloxy group, a $C_{3-8}$ cycloalkyl group, more preferably a $C_{6-14}$ aryl group, a $C_{6-14}$ haloaryl group, a $C_{1-6}$ alkoxy group, a tri-$C_{1-6}$ alkylsilyl group and a $C_{3-8}$ cycloalkyl group, and further preferably a $C_{6-14}$ aryl group or a $C_{3-8}$ cycloalkyl group. Incidentally, the "substituent(s)" in the "primary aliphatic hydrocarbon group having a substituent(s)" as $R^1$ of the carboxylic acid halide represented by the formula (II) can be substituted with the hydrogen atom on the primary carbon atom bonded to the carbonyl carbon.

The terms "N-terminal protected amino acid" and "N-terminal protected peptide" mean an amino acid and a peptide, respectively, in which the amino group at the N-terminal is protected, and the carboxy group at the C-terminal is not protected. Also, the "C-terminal protected amino acid" and the "C-terminal protected peptide" mean an amino acid and a peptide, respectively, in which the carboxy group at the C-terminal is protected, and the amino group at the N-terminal is not protected.

The terms "amino acid in which the N-terminal and the C-terminal are not protected" and the terms "peptide in which the N-terminal and the C-terminal are not protected" mean an amino acid and a peptide, respectively, in which the amino group at the N-terminal and the carboxy group of the C-terminal are not protected. Incidentally, in the amino acid in which the N-terminal and the C-terminal are not protected, when a reactive functional group which does not participate in formation of the peptide is present at the side chain, etc., the functional group may be protected or may not be protected. It is preferably a side chain protected amino acid.

The amino acid used in the present invention is an organic compound having both functional groups of the amino group and the carboxy group, and means a natural and unnatural amino acid. It is preferably an α-, β- or γ-amino acid, or a homoamino acid, and more preferably an α-amino acid. In addition, when two or more amino groups are present in these amino acids (for example, arginine, lysine, 2,3-diaminopropionic acid (Dap), etc.), when two or more carboxy groups are present (for example, glutamic acid, aspartic acid, etc.), or when a reactive functional group is present (for example, cysteine, serine, tyrosine, glutamine, histidine, tryptophane, etc.), the amino acid used in the present invention also includes an amino acid in which the amino group, the carboxy group and/or the reactive functional group which does not participate in the formation of the peptide is/are protected and/or modified.

The "4- to 6-membered cyclic secondary amino acid" used in the present invention means an amino acid in which the nitrogen atom of the amino group and two alkyl groups bonded to the amino group are combined together to form a 4- to 6-membered ring, and specific examples thereof may be mentioned proline. When the 4- to 6-membered ring is fused with a cyclic compound selected from the group consisting of a $C_{6-14}$ aryl ring, a $C_{6-14}$ haloaryl ring and a $C_{3-8}$ cycloalkyl ring, a preferred cyclic compound is a $C_{6-14}$ aryl ring, and more preferably benzene. Accordingly, specific examples of the case where the 4- to 6-membered cyclic secondary amino acid is fused with a cyclic compound may be mentioned 1,2,3,4-tetrahydroisoquinoline-3-carboxylic acid (Tic).

The N—$C_{1-6}$ alkylamino acid used in the present invention is an amino acid in which the amino group of the amino acid is substituted by a $C_{1-6}$ alkyl group which may have a substituent(s), preferably an amino acid in which the amino group of the amino acid is substituted by a $C_{1-6}$ alkyl group which may have a $C_{6-14}$ aryl group, a $C_{6-14}$ haloaryl group, a $C_{1-6}$ alkoxy group, a di-$C_{1-6}$ alkylamino group, a tri-$C_{1-6}$ alkylsilyl group, a tri-$C_{1-6}$ alkylsilyloxy group or a $C_{3-8}$ cycloalkyl group, more preferably an amino acid in which the amino group of the amino acid is substituted by a $C_{1-6}$ alkyl group which may have a $C_{6-14}$ aryl group, a $C_{6-14}$ haloaryl group, a $C_{1-6}$ alkoxy group, a tri-$C_{1-6}$ alkylsilyl group or a $C_{3-8}$ cycloalkyl group, further preferably an amino acid in which the amino group of the amino acid is substituted by a methyl group, an ethyl group, a propyl group, a butyl group, a benzyl group or a cyclohexylmethyl group, more further preferably an amino acid in which the amino group of the amino acid is substituted by a methyl group or an ethyl group, and particularly preferably an amino acid in which the amino group of the amino acid is substituted by a methyl group.

The "group derived from an amino acid" and the "group derived from an N—$C_{1-6}$ alkylamino acid" used in the present invention means a divalent group in which a hydrogen atom is removed from a nitrogen atom of the amino group of the amino acid or of the N—$C_{1-6}$ alkylamino group of the N—$C_{1-6}$ alkylamino acid, and a hydroxy group is removed from the carboxy group. Similarly, the "group derived from an N-methyl amino acid" means a divalent group in which a hydrogen atom is removed from a nitrogen atom of the N-methylamino group of the N-methylamino acid, and a hydroxy group is removed from the carboxy group, the "group derived from the N—$C_{1-6}$ alkylglycine" means a divalent group in which a hydrogen atom is removed from a nitrogen atom of the N—$C_{1-6}$ alkylamino group of the N—$C_{1-6}$ alkylglycine, and a hydroxy group is removed from the carboxy group, the "cyclic secondary a group derived from an amino acid" means a divalent group in which a hydrogen atom is removed from a nitrogen atom of the secondary amino group of the cyclic secondary amino acid, and a hydroxy group is removed from the carboxy group, and the "group derived from a 4- to 6-membered cyclic secondary amino acid" means a divalent group in which a hydrogen atom is removed from a nitrogen atom of the secondary amino group of the 4- to 6-membered cyclic secondary amino acid, and a hydroxy group is removed from the carboxy group.

The amino acid constituting the peptide used in the present invention is the amino acid mentioned above.

The "group derived from a peptide" used in the present invention means a divalent group in which a hydrogen atom is removed from the primary or secondary amino group of various kinds of amino acids constituting the N-terminal, and a hydroxy group is removed from the carboxy group of the amino acid constituting the C-terminal.

The steric structure of the amino acid is not specifically limited, and it is preferably L-isomer.

The "N-terminal protective group" used in the present invention, and, for example, represented by P in the formula (I) and (V) is a protective group at the N-terminal side when the peptide elongation reaction (amidation reaction) is carried out, and conventionally known protective group can be used. Specific examples thereof may be mentioned a carbamate-based protective group (a 9-fluorenylmethoxycarbonyl group, a t-butoxycarbonyl group, a benzyloxycarbonyl group, an allyloxycarbonyl group, a 2,2,2-trichloroethoxycarbonyl group, a 2-(p-biphenyl)isopropyloxycarbonyl group, etc.), an amide-based protective group (an acetyl group, a trifluoroacetyl group, etc.), an imide-based protective group (a phthaloyl group, etc.), a sulfonamide-based protective group (a p-toluenesulfonyl group, a 2-nitrobenzenesulfonyl group, etc.), and a benzyl group, etc., and preferably mentioned a 9-fluorenylmethoxycarbonyl group, a t-butoxycarbonyl group and a benzyloxycarbonyl group.

All technical terms and scientific terms used in the present specification have the same meanings as those commonly understood by those skilled in the art to which the present invention belongs. The same or equivalent optional method and material described in the present specification can be used in practice or experiment of the present invention, and preferable methods and materials are described below. All publications and patents referred to in the present specification are incorporated in the present specification by reference, for example, for the purpose of describing and disclosing the constructs and methodologies, which are described in the publications capable of using in connection with the described inventions.

(Specific Explanation of Producing Method of Peptide of the Present Invention)

Hereinafter, each of Steps (1) to (5) of the producing method of the peptide of the present invention will be explained.

As one embodiment, the production of the peptide of the present invention is constituted by the respective unit steps described as the following Steps (1) to (5).

As one embodiment, the production of the peptide of the present invention can be carried out by subjecting to all the unit steps described as the following Steps (1) to (5) or optionally combining these steps.

Incidentally, the specific explanation is explained based on the following.
(a) $R^1$ and $R^2$ in the descriptions of Steps (1) to (5) have the same meanings as defined above.
(b) The specific conditions of the reaction are not particularly limited as long as the production of the peptide of the present invention is accomplished. Preferred conditions in the respective reactions are appropriately described in detail.
(c) The solvent(s) described in the respective reactions may be used alone or may be used in combination of two or more kinds.

Step (1)

The present step is a step of mixing an N-terminal protected amino acid or an N-terminal protected peptide with a carboxylic acid halide or a halogenated alkyl formate. The present step is a step of activating the C-terminal of the N-terminal protected amino acid or the N-terminal protected peptide with a carboxylic acid halide or a halogenated alkyl formate. In one embodiment of the present invention, this is a step of mixing the N-terminal protected amino acid or the N-terminal protected peptide represented by the formula (I): P-$A^1$-OH (wherein P is an N-terminal protective group, and $A^1$ represents a group derived from an amino acid, a group derived from an N—$C_{1-6}$ alkylamino acid (the $C_{1-6}$ alkyl may have a substituent(s)) or a group derived from a peptide.) with a carboxylic acid halide or a halogenated alkyl formate. In addition, in another embodiment of the present invention, this is a step of mixing the N-terminal protected peptide represented by the formula (V): P-$A^3$-OH (wherein P is an N-terminal protective group, and $A^3$ represents a group derived from a peptide.) with a carboxylic acid halide.

The N-terminal protected amino acid or the N-terminal protected peptide is the above-mentioned amino acid or peptide in which the N-terminal is protected, and is specifically an N-terminal protected amino acid, an N-terminal protected N—$C_{1-6}$ alkylamino acid (the $C_{1-6}$ alkyl may have a substituent(s)) or an N-terminal protected peptide. Incidentally, the N-terminal protected peptide of the present step is preferably an N-terminal protected peptide in which the amino acid at the C-terminal is an amino acid other than the N—$C_{1-6}$ alkylamino acid (the $C_{1-6}$ alkyl may have a substituent(s)) or the 4- to 6-membered cyclic secondary amino acid (the 4- to 6-membered ring may be fused with a cyclic compound selected from the group consisting of a $C_{6-14}$ aryl ring, a $C_{6-14}$ haloaryl ring and a $C_{3-8}$ cycloalkyl ring).

The carboxylic acid halide is represented by the following formula (II).

(wherein X represents a halogen atom, and $R^1$ represents a secondary or tertiary aliphatic hydrocarbon group having 5 or more carbon atoms which may have a substituent(s), or a primary aliphatic hydrocarbon group having 4 or more carbon atoms which have a substituent(s) (here, the substituent(s) on the primary aliphatic hydrocarbon group exists on the carbon atom bonded to the carbonyl carbon).)

The carboxylic acid halide represented by the formula (II) is preferably a carboxylic acid halide wherein $R^1$ is a secondary or tertiary $C_{5-40}$ alkyl group which may have a substituent(s), a $C_{5-10}$ bicycloalkyl group which may have a substituent(s), a $C_{5-15}$ tricycloalkyl group which may have a substituent(s), a secondary or tertiary $C_{5-40}$ alkenyl group which may have a substituent(s), or a primary $C_{4-40}$ alkyl group having a substituent(s) or a primary $C_{4-40}$ alkenyl group having a substituent(s) (here, the substituent(s) of the primary $C_{4-40}$ alkyl group or the primary $C_{4-40}$ alkenyl group exists on the carbon atom bonded to the carbonyl carbon), more preferably a carboxylic acid halide wherein $R^1$ is a secondary or tertiary $C_{5-20}$ alkyl group which may have a substituent(s), a $C_{7-10}$ bicycloalkyl group which may have a substituent(s), a $C_{7-15}$ tricycloalkyl group which may have a substituent(s), a secondary or tertiary $C_{5-20}$ alkenyl group which may have a substituent(s), or a primary $C_{4-20}$ alkyl group having a substituent(s) or a primary $C_{4-20}$ alkenyl group having a substituent(s) (here, the substituent(s) of the primary $C_{4-20}$ alkyl group or the primary $C_{4-20}$ alkenyl group exists on the carbon atom bonded to the carbonyl carbon), further preferably a carboxylic acid chloride wherein $R^1$ is a secondary or tertiary $C_{5-20}$ alkyl group which may have a substituent(s), a $C_{7-10}$ bicycloalkyl group which may have a substituent(s), a $C_{7-15}$ tricycloalkyl group which may have a substituent(s), a secondary or tertiary $C_{5-20}$ alkenyl group which may have a substituent(s), or an isobutyl group having a substituent(s), and further preferably selected from the following compounds group.

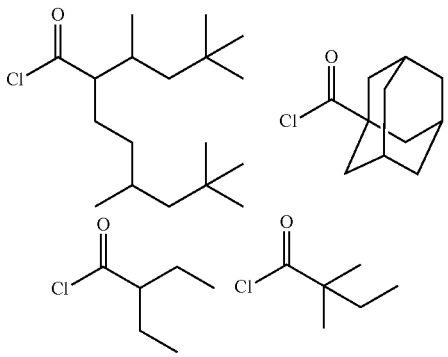

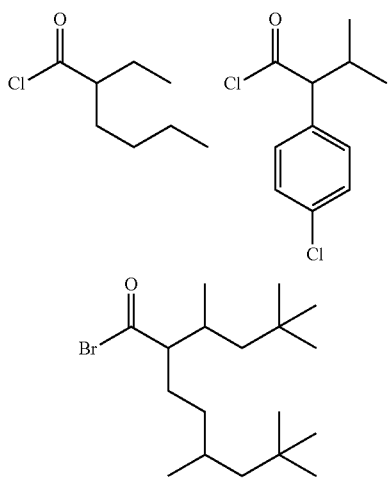

It is particularly preferably selected from the following compounds group.

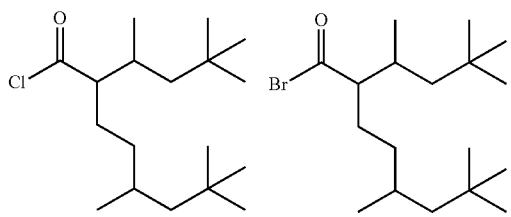

The halogenated alkyl formate is represented by the following formula (III).

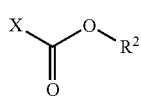
(III)

(wherein X represents a halogen atom, and $R^2$ represents a secondary aliphatic hydrocarbon group having 5 or more carbon atoms which may have a substituent(s).)

The halogenated alkyl formate represented by the formula (III) is preferably a halogenated alkyl formate wherein $R^2$ is a secondary $C_{5-40}$ alkyl group which may have a substituent(s), a $C_{5-8}$ cycloalkyl group which may have a substituent(s) or a secondary $C_{5-40}$ alkenyl group which may have a substituent(s), more preferably a halogenated alkyl formate wherein $R^2$ is a secondary $C_{5-20}$ alkyl group which may have a substituent(s), a $C_{5-6}$ cycloalkyl group which may have a substituent(s) or a secondary $C_{5-20}$ alkenyl group which may have a substituent(s), further preferably a chloroalkyl formate wherein $R^2$ is a secondary $C_{5-20}$ alkyl group which may have a substituent(s), a $C_{5-6}$ cycloalkyl group which may have a substituent(s) or a secondary $C_{5-20}$ alkenyl group which may have a substituent(s), and particularly preferably selected from the following compounds group.

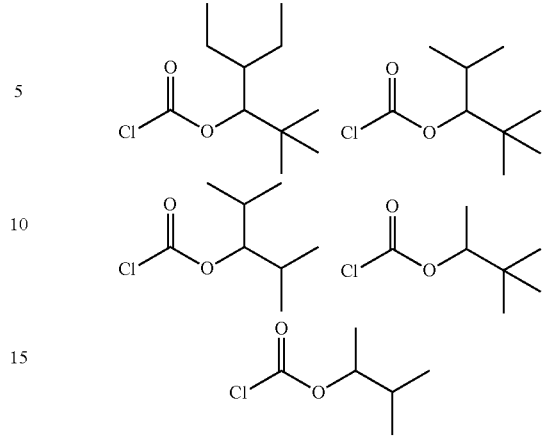

The number of the carbon in $R^1$ or $R^2$ is a sum of the number of the carbon atoms possessed by each of $R^1$ or $R^2$, and when $R^1$ or $R^2$ has a substituent(s), the number of the carbon atoms in the substituent(s) is also included.

Mixing (activation reaction) of the carboxylic acid halide or the halogenated alkyl formate and the N-terminal protected amino acid or the N-terminal protected peptide can be carried out, if necessary, in the presence of a base and/or a solvent.

The base used in the present step is not particularly limited, and an example thereof may be mentioned an aliphatic amine (for example, triethylamine, N,N-diisopropylethylamine, N-methylmorpholine), an aromatic amine (for example, pyridine, imidazole, N,N-dimethyl-4-aminopyridine), an amidine (for example, diazabicycloundecene), an alkali metal salt (for example, sodium hydrogen carbonate, potassium carbonate), etc. It is preferably an aliphatic amine, and more preferably N,N-diisopropylethylamine, triethylamine or N-methylmorpholine.

An amount of the carboxylic acid halide or the halogenated alkyl formate used in the present step is preferably 0.2 equivalent to 50 equivalent, more preferably 0.5 equivalent to 20 equivalent, and further preferably 0.8 equivalent to 5 equivalent based on the N-terminal protected amino acid or the N-terminal protected peptide.

An amount of the base used in the present step is preferably 0.2 equivalent to 50 equivalent, more preferably 0.5 equivalent to 20 equivalent, further preferably 0.8 equivalent to 5 equivalent based on the carboxylic acid halide or the halogenated alkyl formate.

The solvent used in the present step is not particularly limited as long as it does not interfere the activation reaction, and an example thereof may be mentioned a halogen-containing hydrocarbon solvent (for example, dichloromethane, chloroform), an aromatic hydrocarbon solvent (for example, toluene, xylene), an ether solvent (for example, tetrahydrofuran, 1,4-dioxane, cyclopentyl methyl ether, methyl-t-butyl ether), an amide solvent (for example, N,N-dimethylformamide, N,N-dimethylacetamide), a nitrile solvent (for example, acetonitrile), a ketone solvent (for example, acetone, methyl ethyl ketone), aliphatic hydrocarbon solvent (for example, hexane, heptane, cyclohexane), an ester solvent (for example, ethyl acetate), etc. It is preferably a nitrile solvent, an amide solvent or an ether solvent, and more preferably acetonitrile, tetrahydrofuran or N,N-dimethylacetamide.

An amount of the solvent used in the present step is preferably 100-fold by mass or less, more preferably 1-fold by mass to 50-fold by mass, further preferably 3-fold by mass to 20-fold by mass based on the carboxylic acid halide or the halogenated alkyl formate.

According to these procedures, if necessary, in the presence of a solvent and/or a base, the N-terminal protected amino acid or the N-terminal protected peptide is mixed with the carboxylic acid halide or the halogenated alkyl formate. The obtained mixture is, if necessary, controlled its temperature using an oil bath or a cooling bath. The temperature of the mixture is not particularly limited, and is preferably −40° C. to a reflux temperature of the mixture, more preferably −20° C. to 50° C., and further preferably −10° C. to 30° C.

According to the present step, the N-terminal protected amino acid or the N-terminal protected peptide in which the C-terminal has been activated can be formed. Accordingly, the product obtained by the present step means an N-terminal protected amino acid or an N-terminal protected peptide the C-terminal of which has been activated, or a mixture containing either of these. The N-terminal protected amino acid or the N-terminal protected peptide the C-terminal of which has been activated thus obtained may be used in the subsequent Step (3) as a reaction mixture as such without subjecting to a purification step, or by isolating as a (crude) purified product.

Step (2)

The present step is a step of mixing an N-alkylamino acid or a peptide having an N-alkylamino acid at the N-terminal with a silylating agent. Incidentally, in the present step, the terms "N-alkylamino acid" mean an N-alkylamino acid in which the amino group at the N-terminal and the carboxy group at the C-terminal are not protected, and the terms "peptide having an N-alkylamino acid at the N-terminal" mean a peptide having an N-alkylamino acid at the N-terminal, and the amino group at the N-terminal and the carboxy group at the C-terminal of which are not protected. The present step is a step of reacting an N-alkylamino acid or a peptide having an N-alkylamino acid at the N-terminal with a silylating agent to obtain an N-alkylamino acid or a peptide having an N-alkylamino acid at the N-terminal in which the C-terminal, the N-terminal and/or (when it is present) at least a part of the functional group such as a hydroxy group, etc., of the amino acid or the peptide is trialkylsilylated (in the following, it is also referred to as "trialkylsilylated amino acid or peptide"). In one embodiment of the present invention, this is a step of mixing an amino acid in which the amide group at the N-terminal and the carboxy group at the C-terminal are not protected or a peptide in which the amide group at the N-terminal and the carboxy group at the C-terminal are not protected represented by the formula (IV): H-A$^2$-OH [wherein A$^2$ represents a group derived from an N—C$_{1-6}$ alkylamino acid (the C$_{1-6}$ alkyl may have a substituent(s)), or a group derived from a 4- to 6-membered cyclic secondary amino acid (the 4- to 6-membered ring may be fused with a cyclic compound selected from the group consisting of a C$_{6-14}$ aryl ring, a C$_{6-14}$ haloaryl ring and a C$_{3-8}$ cycloalkyl ring), or a group derived from a peptide in which the N-terminal residue is an N—C$_{1-6}$ alkylamino acid (the C$_{1-6}$ alkyl may have a substituent(s)) or a 4- to 6-membered cyclic secondary amino acid (the 4- to 6-membered ring may be fused with a cyclic compound selected from the group consisting of a C$_{6-14}$ aryl ring, a C$_{6-14}$ haloaryl ring and a C$_{3-8}$ cycloalkyl ring)] with a silylating agent. Also, in another embodiment of the present invention, this is a step of mixing an amino acid in which the amino group at the N-terminal and the carboxy group at the C-terminal are not protected represented by the formula (IV'): H-A$^{2'}$-OH [wherein A$^{2'}$ represents a group derived from an N-methylamino acid, a group derived from an N—C$_{1-6}$ alkylglycine (the C$_{1-6}$ alkyl may have a substituent(s)), or a group derived from a 4- to 6-membered cyclic secondary amino acid] with a silylating agent.

Also, an amino acid at the N-terminal in the N-alkylamino acid or the peptide having the N-alkylamino acid at the N-terminal in the present step is preferably an N—C$_{1-6}$ alkylamino acid (the C$_{1-6}$ alkyl may be substituted by cyclohexyl or phenyl), more preferably N-methylamino acid, N-ethylamino acid, N-propylamino acid, N-butylamino acid, N-pentylamino acid, N-cyclohexylmethylamino acid or N-benzylamino acid, further preferably N-methylamino acid or N-ethylamino acid, and particularly preferably N-methylamino acid.

The silylating agent of the present step is not particularly limited, and an example thereof may be mentioned a trimethylsilylating agent such as trimethylsilyl chloride, trimethylsilyl cyanide, 1,1,1,3,3,3-hexamethyldisilazane, N-trimethylsilyl-acetamide, N,N'-bis(trimethylsilyl)urea, N-methyl-N-trimethylsilyltrifluoroacetamide, N,O-bis(trimethylsilyl)acetamide, N,O-bis(trimethylsilyl)trifluoroacetamide, etc., N-(tert-butyldimethylsilyl)-N-methyltrifluoroacetamide, etc. It is preferably trimethylsilyl chloride, N,O-bis(trimethylsilyl)acetamide, N,N'-bis(trimethylsilyl)urea or N,O-bis(trimethylsilyl)trifluoroacetamide, and more preferably N, O-bis(trimethyl-silyl)acetamide.

An amount of the silylating agent to be used is preferably 0.01 equivalent to 50 equivalent, more preferably 0.1 equivalent to 20 equivalent, and further preferably 0.2 equivalent to 5 equivalent based on the N-alkylamino acid or the peptide having the N-alkylamino acid at the N-terminal.

Mixing (silylation reaction) of the N-alkylamino acid or the peptide having the N-alkylamino acid at the N-terminal with the silylating agent can be carried out, if necessary, in the presence of a base and/or a solvent.

The base to be used is not particularly limited, and an example thereof may be mentioned an aliphatic amine (for example, dicyclohexylamine, piperidine, triethylamine, N,N-diisopropylethylamine, N-methylmorpholine), an aromatic amine (for example, pyridine, imidazole, N,N-dimethyl-4-aminopyridine), an alkali metal salt (for example, sodium hydrogen carbonate, potassium carbonate), etc. It is preferably an aliphatic amine, and more preferably triethylamine and N,N-diisopropylethylamine.

An amount of the base to be used is preferably 0.01 equivalent to 50 equivalent, more preferably 0.1 equivalent to 20 equivalent, and further preferably 0.2 equivalent to 5 equivalent based on the N-alkylamino acid or the peptide having the N-alkylamino acid at the N-terminal.

The solvent used in the present step is not specifically limited as long as it does not interfere the silylation reaction, and an example thereof may be mentioned a halogen-containing hydrocarbon solvent (for example, dichloromethane, chloroform), an aromatic hydrocarbon solvent (for example, toluene, xylene), an ether solvent (for example, tetrahydrofuran, 1,4-dioxane, cyclopentyl methyl ether, methyl-t-butyl ether), an amide solvent (for example, N,N-dimethylformamide), a nitrile solvent (for example, acetonitrile), etc. It is preferably a nitrile solvent, an amide solvent or an ether solvent, and more preferably acetonitrile, tetrahydrofuran or N,N-dimethylacetamide.

An amount of the solvent used in the present step is preferably 100-fold by mass or less, more preferably 1-fold by mass to 50-fold by mass, further preferably 3-fold by mass to 20-fold by mass based on the N-alkylamino acid or the peptide having the N-alkylamino acid at the N-terminal.

As mentioned above, if necessary, in the presence of a solvent and/or a base, an N-alkylamino acid or a peptide having an N-alkylamino acid at the N-terminal is mixed with a silylating agent. The temperature of the obtained mixture is controlled, if necessary, using an oil bath or a cooling bath. The temperature of the mixture is not particularly limited, and preferably from 0° C. to the reflux temperature of the mixture, more preferably 10° C. to 100° C., and further preferably 20° C. to 80° C. In addition, the mixture may be applied to microwave irradiation.

According to the present step, a trialkylsilylated N-alkylamino acid or the peptide having the N-alkylamino acid at the N-terminal is formed. Accordingly, the product obtained by the present step means a mixture containing a trialkylsilylated N-alkylamino acid or peptide having the N-alkylamino acid at the N-terminal. The trialkylsilylated amino acid or peptide thus obtained may be used in the subsequent Step (3) as a reaction mixture as such without subjecting to the purification step, or after isolation as a (crude) purified product. In addition, the trialkylsilylated N-alkylamino acid or peptide having the N-alkylamino acid at the N-terminal can be analyzed by an analytical instrument such as NMR, etc.

Step (3)

The present step is a step of mixing the product obtained in Step (1) and the product obtained in Step (2). The present step is a peptide elongation step in which the N-terminal protected amino acid or the N-terminal protected peptide in which the C-terminal is activated obtained in Step (1), and the trialkylsilylated amino acid or peptide obtained in Step (2) are reacted, and it is preferably carried out by mixing and stirring the reaction mixture obtained in Step (1) and the reaction mixture obtained in Step (2). In one embodiment of the present invention, this is a peptide elongation step by reacting the N-terminal protected amino acid in which the C-terminal is activated obtained in Step (1), and the trialkylsilylated amino acid or peptide obtained in Step (2). In another embodiment of the present invention, this is a peptide elongation step by reacting the N-terminal protected peptide in which the C-terminal is activated obtained in Step (1), and the trialkylsilylated amino acid obtained in Step (2).

The temperature of the obtained mixture is controlled, if necessary, using an oil bath or a cooling bath. The temperature of the mixture is not particularly limited, and preferably from −40° C. to the reflux temperature of the reaction mixture, more preferably −20° C. to 50° C., and further preferably −10° C. to 30° C.

Also, in the method for producing a peptide of the present invention, the following Steps (4) to (5) are repeated to the peptide obtained in Step (3) with a desired number of times so that the peptide chain can be further elongated.
(4) A step of removing the protective group at the N-terminal of the peptide obtained in Step (3) or (5).
(5) A step of reacting an N-terminal protected amino acid or an N-terminal protected peptide with an N-terminal of the peptide obtained in Step (4).

Step (5) can be carried out by the same operation as in the above-mentioned Steps (1), (2) and (3), or by a general peptide synthesis reaction.

In the method for producing a peptide of the present invention, it is also possible to appropriately omit the purification step of Steps (1) to (5) within the range which does not exert an effect to the reaction of the next step.

Step (4): Deprotection Step of N-Terminal

The present step is a step of removing the protective group at the N-terminal from the peptide obtained in the above-mentioned Step (3) or (5) to obtain a peptide in which the N-terminal and the C-terminal are unprotected.

The deprotection reagent used in the present step is appropriately selected depending on the protective group to be used. An example thereof may be mentioned an acid (for example, trifluoroacetic acid, hydrochloric acid, Lewis acid), a secondary or tertiary amine (for example, pyrrolidine, piperidine, morpholine, triethylamine), hydrogenation decomposition (for example, a palladium catalyst/hydrogenation), etc.

The deprotection conditions used in the present step are appropriately selected depending on the kind of the N-terminal protective group and, for example, in the case of a 9-fluorenylmethoxycarbonyl group, it is carried out by treating with a base, in the case of a t-butoxycarbonyl group, it is carried out by treating with an acid, and in the case of a benzyloxycarbonyl group or an allyloxycarbonyl group, it is carried out in neutral, for example, by subjecting to hydrogenation in the presence of a metal catalyst.

In each reaction, when the reaction substrate has a hydroxy group, a mercapto group, an amino group, a carboxy group or a carbonyl group (in particular, when a functional group is possessed at the side chain of the amino acid or the peptide), a protective group generally used in the peptide chemistry, etc., may be introduced into these groups, and the objective compound can be obtained by removing the protective group after the reaction, if necessary.

Protection and deprotection can be carried out using a generally known protective group and subjecting to protection and deprotection reaction (for example, see Protective Group in Organic Synthesis, Fourth edition, written by T. W. Greene, John Wiley & Sons Inc. (2006), etc.).

A combination of the N-terminal protected amino acid or the N-terminal amino acid in the N-terminal protected peptide used in Step (1) (in the following, Amino acid A) and the amino acid or the N-terminal amino acid in the peptide used in Step (2) (in the following, Amino acid B) is not particularly limited, and preferably Amino acids A and B are each an α-, β- or γ-amino acid, more preferably either of Amino acid A or Amino acid B is an α-amino acid, further preferably Amino acid A is an α-amino acid and Amino acid B is an α-amino acid, a β-amino acid or a γ-amino acid, or Amino acid A is an α-amino acid, a β-amino acid or a γ-amino acid and Amino acid B is an α-amino acid, and particularly preferably Amino acid A is an α-amino acid and Amino acid B is an α-amino acid, a β-amino acid or a γ-amino acid.

Also, the N-terminal amino acid in the peptide used in Step (2) is preferably an α-amino acid.

EXAMPLES

Hereinafter, the present invention will be explained in more detail by referring to Reference Examples, Comparative Examples and Synthetic Examples as Examples, but the present invention is not limited to these Examples.

In the present specification, when the amino acid, etc., are indicated as an abbreviation, each indication is based on the abbreviation by IUPAC-IUB Commission on Biochemical Nomenclature or the conventional abbreviation in this field of the art.

Incidentally, in Synthetic Example, "(v/v)" means (volume/volume), and "M" means mol/L.

In the following Synthetic Examples, as the microwave reactor, Initiator+(manufactured by Biotage) was used.

The proton nuclear magnetic resonance ($^1$H-NMR) in Synthetic Examples was measured by, unless otherwise specifically mentioned, JNM-ECP300 manufactured by JEOL, Ltd., or JNM-ECX300 manufactured by JEOL, Ltd., or Ascend™ 500 manufactured by Bruker Co., in deuterated chloroform or deuterated dimethyl sulfoxide solvent, and the chemical shift was shown by the δ value (ppm) when tetramethylsilane was used as the internal standard (0.0 ppm).

In the description of the NMR spectrum, "s" means singlet, "d" doublet, "t" triplet, "q" quartet, "dd" doublet of doublet, "dt" doublet of triplet, "sept" septet, "m" multiplet, "br" broad, "J" coupling constant, "Hz" hertz, "CDCl$_3$" deuterated chloroform, and "DMSO-d$_6$" deuterated dimethyl sulfoxide.

High performance liquid chromatography/mass analysis was measured using, unless otherwise specifically mentioned, either of ACQUITY UPLC H-Class/QDa, manufactured by Waters Corporation, ACQUITY UPLC H-Class/SQD2 manufactured by Waters Corporation, or LC-20AD/Triple Tof5600 manufactured by Shimadzu Corporation.

In the description of high performance liquid chromatography/mass analysis, ESI+ means a positive mode of the electrospray ionization method, M+H means a proton adduct and M+Na means a sodium adduct.

In the description of high performance liquid chromatography/mass analysis, ESI– means a negative mode of the electrospray ionization method, and M–H means a proton deficient.

With regard to the ratio of the starting materials and the product, in Synthetic Examples 8 to 50, it was calculated either of the analyses <Analytical condition 1> to <Analytical condition 3> using high performance liquid chromatography.

<Analytical Condition 1>
High performance liquid chromatography: ACQUITY UPLD H-Class/SQD2 manufactured by Waters Corporation
Column: Kinetex EVO C$_{18}$ (1.7 μm, 2.1×50 mm) manufactured by Phenomenex Column oven temperature: 60° C.
Eluent: Acetonitrile:0.025 vol % trifluoroacetic acid aqueous solution
5:95 (0-2.1 min), 95:5 (2.1-2.84 min) (v/v)
Eluent speed: 0.6 mL/min
Detection wavelength: 220 nm
<Analytical Condition 2>
High performance liquid chromatography: ACQUITY UPLD H-Class/SQD2 manufactured by Waters Corporation
Column: ACQUITY BEH C18 (1.7 μm, 2.1×100 mm) manufactured by Waters Corporation
Column oven temperature: 60° C.
Eluent: Acetonitrile:0.025 vol % trifluoroacetic acid aqueous solution 5:95 (0-3.7 min), 95:5 (3.7-4.81 min) (v/v) Eluent speed: 0.6 mL/min
Detection wavelength: 220 nm
<Analytical Condition 3>
High performance liquid chromatography: ACQUITY UPLD H-Class/SQD2 manufactured by Waters Corporation
Column: ACQUITY BEH C18 (1.7 μm, 2.1×100 mm) manufactured by Waters Corporation
Column oven temperature: 40° C.
Eluent: acetonitrile:0.025 vol % trifluoroacetic acid aqueous solution 5:95 (0-5.56 min), 95:5 (5.56-7.22 min) (v/v)
Eluent speed: 0.4 mL/min
Detection wavelength: 220 nm In purification by silica gel column chromatography, unless otherwise specifically mentioned, either of Hi-Flash column manufactured by Yamazen Corporation, SNAP Ultra Silica Cartridge manufactured by Biotage AG, silica gel 60 manufactured by Merck or PSQ60B manufactured by Fuji Silysia Chemical Ltd., was used.

In the following, otherwise specifically mentioned, N,O-bis(trimethylsilyl)-acetamide used was a commercially available product having a purity of 98%.

Incidentally, in the following Examples, the yield or quantitative yield sometimes exceeds 100%. These are all exceeded 100% due to measurement error, the influence of the purity of the starting materials or the product, or other factors based on common general technical knowledge. In the following Examples, the causes when the yield exceeds 100% are not individually referred to, but those skilled in the art can fully understand the scientific validity of these Examples.

Synthetic Example 1: Synthesis of 4-ethyl-2,2-dimethylhexan-3-ol

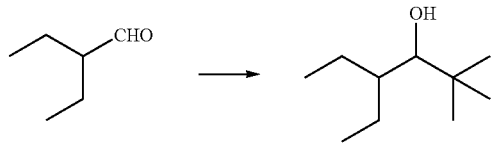

2-Ethylbutyl aldehyde (3.69 g, 36.8 mmol) was mixed with cyclopentyl methyl ether (40 mL), and a tert-butyl lithium pentane solution (1.53M, 26.5 mL, 40.5 mmol) was added to the mixture at −78° C. and the resulting mixture was stirred for 5 minutes. After the temperature of the obtained reaction mixture was raised to 25° C., ethanol (1.0 mL) was added thereto and washed successively with a 20 wt % aqueous ammonium chloride solution (25 mL) and a saturated aqueous sodium chloride solution (25 mL). The obtained organic layer was concentrated and the concentrate was purified by silica gel column chromatography to obtain 4-ethyl-2,2-dimethylhexan-3-ol (5.22 g, yield: 90%) as a colorless transparent liquid.

$^1$H-NMR (CDCl$_3$)
δ ppm: 0.88-0.94 (9H+4H, m), 1.06-1.16 (1H, m), 1.27 (1H, d, J=6.0 Hz), 1.29-1.38 (2H, m), 1.40-1.48 (1H, m), 1.52-1.58 (1H, m), 3.24 (1H, d, J=6.0 Hz).

Synthetic Example 2: Synthesis of 4-ethyl-2,2-dimethylhexan-3-yl carbonochloridate

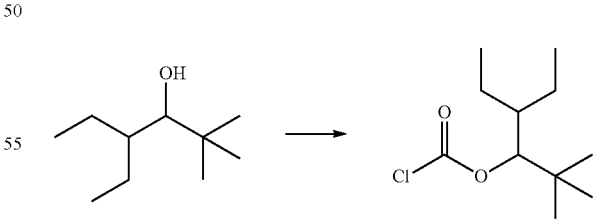

4-Ethyl-2,2-dimethylhexan-3-ol (5.21 g, 32.9 mmol) and pyridine (2.99 g, 37.9 mmol) were mixed with carbon tetrachloride (50 mL), and the mixture was cooled to 0° C. To the solution was added a solution in which triphosgene (4.00 g, 13.5 mmol) and carbon tetrachloride (10 mL) had been mixed separately, and the mixture was further heated to 60° C. and stirred for 8 hours. The obtained reaction mixture was successively washed with water (50 mL) twice and a saturated aqueous sodium chloride solution (50 mL). The obtained organic layer was concentrated to obtain 4-ethyl-2,2-dimethylhexan-3-yl carbonochloridate (6.56 g, yield: 90%) as a colorless transparent liquid. This compound was used for the next step without further purification.

$^1$H-NMR (CDCl$_3$)

δ ppm: 0.90-0.94 (6H, m), 0.97 (9H, s), 1.10-1.20 (1H, m), 1.25-1.35 (1H, m), 1.45-1.53 (2H, m), 1.59-1.67 (1H, m), 4.72 (1H, d, J=2.0 Hz).

Synthetic Example 3: Synthesis of 2,2,4-trimethylpentan-3-ol

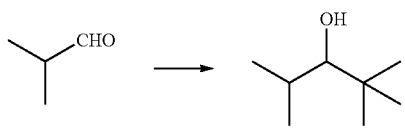

Isobutyl aldehyde (3.61 g, 50.0 mmol) was mixed with cyclopentyl methyl ether (50 mL), and a tert-butyl lithium pentane solution (1.52M, 36.2 mL, 55.0 mmol) was added to the mixture at −78° C. and the resulting mixture was stirred for 5 minutes. After the temperature of the obtained reaction mixture was raised to 25° C., ethanol (1.0 mL) was added thereto and washed successively with 20 wt % aqueous ammonium chloride solution (25 mL) and a saturated aqueous sodium chloride solution (25 mL). The obtained organic layer was concentrated and the concentrate was purified by silica gel column chromatography to obtain 2,2,4-trimethylpentan-3-ol (5.25 g, yield: 81%) as a colorless transparent liquid.

$^1$H-NMR (CDCl$_3$)

δ ppm: 0.91 (3H, d, J=7.0 Hz), 0.94 (9H, s), 1.01 (3H, d, J=7.0 Hz), 1.32 (1H, d, J=6.5 Hz), 1.91-1.99 (1H, m), 3.11 (1H, dd, J=6.5 Hz, 2.0 Hz).

Synthetic Example 4: Synthesis of 2,2,4-trimethylpentan-3-yl carbonochloridate

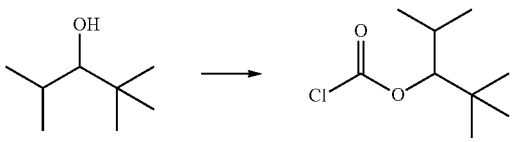

2,2,4-trimethylpentan-3-ol (5.25 g, 40.3 mmol) and pyridine (3.67 g, 46.3 mmol) were mixed with carbon tetrachloride (40 mL), and the mixture was cooled to 0° C. To the solution was added a solution in which triphosgene (4.90 g, 16.5 mmol) and carbon tetrachloride (20 mL) had been mixed separately, and the mixture was further heated to 60° C. and stirred for 8 hours. The obtained reaction mixture was successively washed with water (50 mL) twice and a saturated aqueous sodium chloride solution (50 mL). The obtained organic layer was concentrated to obtain 2,2,4-trimethylpentan-3-yl carbonochloridate (6.06 g, yield: 78%) as a colorless transparent liquid. This compound was used for the next step without further purification.

$^1$H-NMR (CDCl$_3$) δ ppm: 0.97 (3H, d, J=7.0 Hz), 0.99 (9H, s), 1.02 (3H, d, J=7.0 Hz), 2.04-2.13 (1H, m), 4.58 (1H, d, J=3.0 Hz).

Synthetic Example 5: Synthesis of 3,3-dimethylbutan-2-yl carbonochloridate

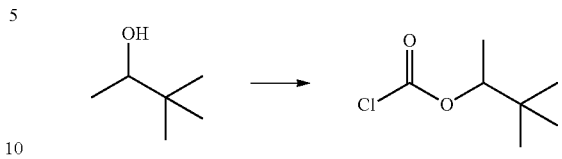

3,3-Dimethylbutan-2-ol (3.36 g, 32.9 mmol) and pyridine (2.99 g, 37.8 mmol) were mixed with carbon tetrachloride (40 mL), and the mixture was cooled to 0° C. To the solution was added a solution in which triphosgene (4.00 g, 13.5 mmol) and carbon tetrachloride (15 mL) had been mixed separately, and the mixture was further heated to 60° C. and stirred for 8 hours. The obtained reaction mixture was successively washed with water (50 mL) twice and a saturated aqueous sodium chloride solution (50 mL). The obtained organic layer was concentrated to obtain 3,3-dimethylbutan-2-yl carbonochloridate (4.50 g, yield: 83%) as a colorless transparent liquid. This compound was used for the next step without further purification.

$^1$H-NMR (CDCl$_3$)

δ ppm: 0.96 (9H, s), 1.29 (3H, d, J=6.5 Hz), 4.74 (1H, q, J=6.5 Hz).

Synthetic Example 6: Synthesis of 2,4-dimethylpentan-3-yl carbonochloridate

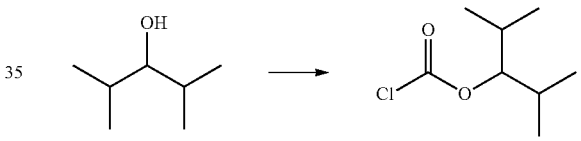

2,4-dimethylpentan-3-ol (3.49 g, 30.0 mmol) and pyridine (2.73 g, 34.5 mmol) were mixed with carbon tetrachloride (40 mL), and the mixture was cooled to 0° C. To the solution was added a solution in which triphosgene (3.65 g, 12.3 mmol) and carbon tetrachloride (15 mL) had been mixed separately, and the mixture was further heated to 60° C. and stirred for 8 hours. The obtained reaction mixture was successively washed with water (50 mL) twice and a saturated aqueous sodium chloride solution (50 mL). The obtained organic layer was concentrated to obtain 2,4-dimethylpentan-3-yl carbonochloridate (5.10 g, yield: 95%) as a colorless transparent liquid. This compound was used for the next step without further purification.

$^1$H-NMR (CDCl$_3$)

δ ppm: 0.94 (6H, d, J=2.5 Hz), 0.95 (6H, d, J=2.5 Hz), 1.94-2.04 (2H, m) 4.60 (1H, t, J=6.0 Hz).

Synthetic Example 7: Synthesis of 3-methylbutan-2-yl carbonochloridate

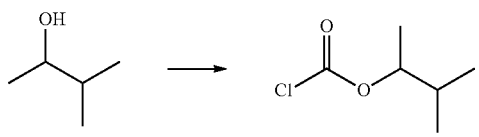

3-Methylbutan-2-ol (3.97 g, 45.0 mmol) and pyridine (4.09 g, 51.8 mmol) were mixed with carbon tetrachloride (40 mL), and the mixture was cooled to 0° C. To the solution was added a solution in which triphosgene (5.47 g, 18.5 mmol) and carbon tetrachloride (20 mL) had been mixed separately, and the mixture was further heated to 60° C. and stirred for 8 hours. The obtained reaction mixture was successively washed with water (50 mL) twice and a saturated aqueous sodium chloride solution (50 mL). The obtained organic layer was concentrated to obtain 3-methylbutan-2-yl carbonochloridate (5.10 g, yield: 95%) as a colorless transparent liquid. This compound was used for the next step without further purification.

$^1$H-NMR (CDCl$_3$)

δ ppm: 0.95 (3H, d, J=4.0 Hz), 0.97 (3H, d, J=4.0 Hz), 1.31 (3H, d, J=6.5 Hz), 1.87-1.94 (1H, m), 4.80 (1H, sept, J=6.5 Hz).

Synthetic Example 8: Synthesis of Boc-Phe-MePhe-OH

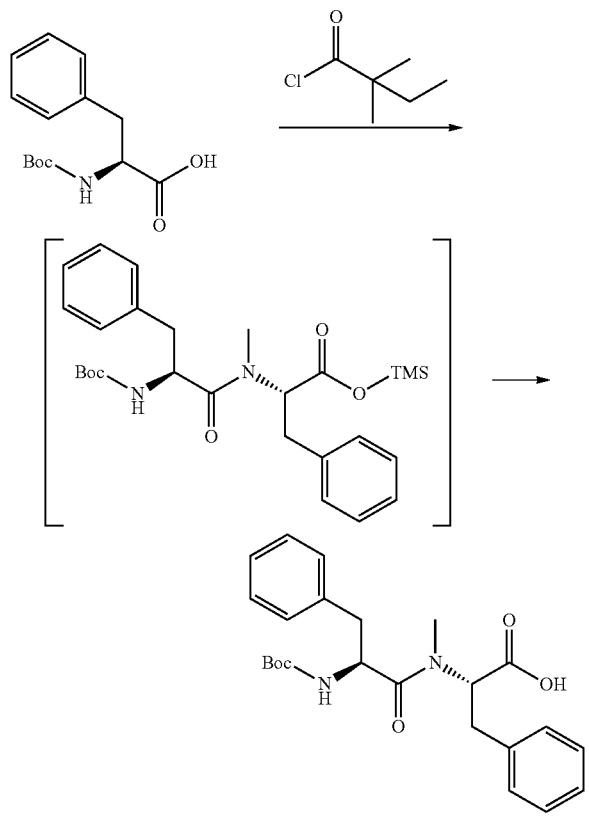

Boc-Phe-OH (0.066 g, 0.25 mmol) and triethylamine (0.033 g, 0.32 mmol) were mixed with tetrahydrofuran (5 mL), and 2,2-dimethylbutanoyl chloride (0.040 g, 0.30 mmol) was added to the mixture at 0° C. and the resulting mixture was stirred for 1 hour. To the solution was added a solution which had been separately prepared by mixing H-MePhe-OH (0.067 g, 0.38 mmol), N,O-bis(trimethylsilyl)acetamide (0.161 g, 0.750 mmol) and acetonitrile (4 mL) and stirring the mixture at 75° C. for 3 minutes under microwave irradiation, and the resulting mixture was stirred at 0° C. for 2 hours and further stirred at 25° C. for 16 hours (starting material:target compound=1:70 (Analytical condition 3)). The obtained reaction mixture was concentrated and then diluted with ethyl acetate (20 mL), and successively washed with a 10 wt % aqueous citric acid solution (10 mL) twice, a 5 wt % aqueous sodium chloride solution (10 mL) and a saturated aqueous sodium chloride solution (10 mL). The obtained organic layer was concentrated to obtain Boc-Phe-MePhe-OH (0.125 g, yield: 117%) as a white solid.

MASS (ESI+) m/z; (M+H)+427.3

Synthetic Example 9: Synthesis of Fmoc-Phe-MePhe-OH

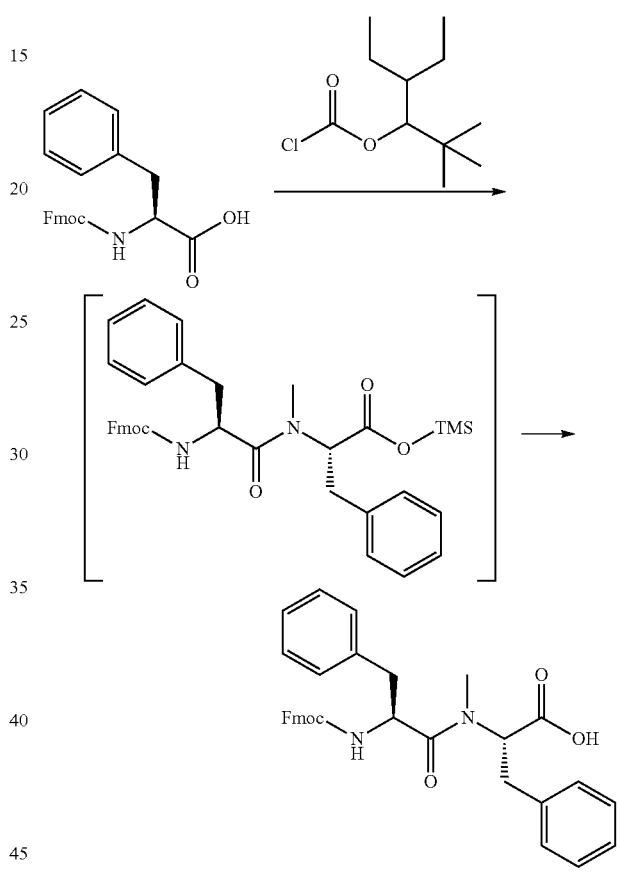

Fmoc-Phe-OH (0.097 g, 0.25 mmol) and N-methylmorpholine (0.033 g, 0.33 mmol) were mixed with tetrahydrofuran (5.0 mL), and 4-ethyl-2,2-dimethylhexan-3-yl carbonochloridate (0.066 g, 0.30 mmol) was added to the mixture at 0° C. and the resulting mixture was stirred for 1 hour. To the solution was added a solution which had been separately prepared by mixing H-MePhe-OH (0.058 g, 0.33 mmol), N,O-bis(trimethylsilyl)acetamide (0.141 g, 0.67 mmol) and acetonitrile (4.0 mL) and stirring the mixture at 75° C. for 20 minutes, and further stirred at 25° C. for 5 hours (starting material:target compound=1:13 (Analytical condition 3)). The obtained reaction mixture was diluted with ethyl acetate (20 mL), and successively washed with a 10 wt % aqueous citric acid solution (20 mL), a 10 wt % aqueous sodium chloride solution (20 mL) and a saturated aqueous sodium chloride solution (20 mL). The obtained organic layer was concentrated and the concentrate was purified by silica gel column chromatography to obtain Fmoc-Phe-MePhe-OH (0.137 g, yield: 100%) as a white solid.

MASS (ESI+) m/z; (M+H)+549.3

Synthetic Example 10: Synthesis of Fmoc-Phe-MePhe-OH

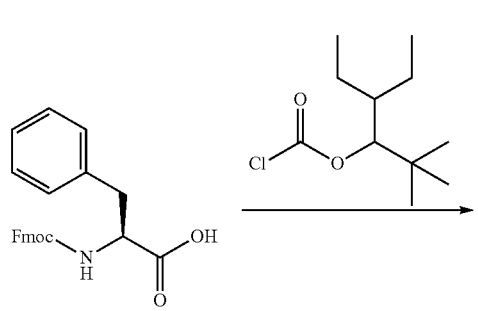

Fmoc-Phe-OH (0.097 g, 0.25 mmol) and N-methylmorpholine (0.033 g, 0.33 mmol) were mixed with N,N-dimethylacetamide (5.0 mL), and 4-ethyl-2,2-dimethyl-hexan-3-yl carbonochloridate (0.066 g, 0.30 mmol) was added to the mixture at 0° C. and the resulting mixture was stirred for 1 hour. To the solution was added a solution which had been separately prepared by mixing H-MePhe-OH (0.058 g, 0.33 mmol), N,O-bis(trimethylsilyl)acetamide (0.141 g, 0.67 mmol) and acetonitrile (4.0 mL) and stirring the mixture at 75° C. for 20 minutes, and further stirred at 25° C. for 5 hours (starting material:target compound=1:31 (Analytical condition 3)). The obtained reaction mixture was diluted with ethyl acetate (30 mL), and successively washed with a 10 wt % aqueous citric acid solution (50 mL), 10 wt % aqueous sodium chloride solution (20 mL) and a saturated aqueous sodium chloride solution (20 mL). The obtained organic layer was concentrated and the concentrate was purified by silica gel column chromatography to obtain Fmoc-Phe-MePhe-OH (0.137 g, yield: 100%) as a white solid.

MASS (ESI+) m/z; (M+H)+549.3

Synthetic Example 11: Synthesis of Fmoc-Phe-MePhe-OH

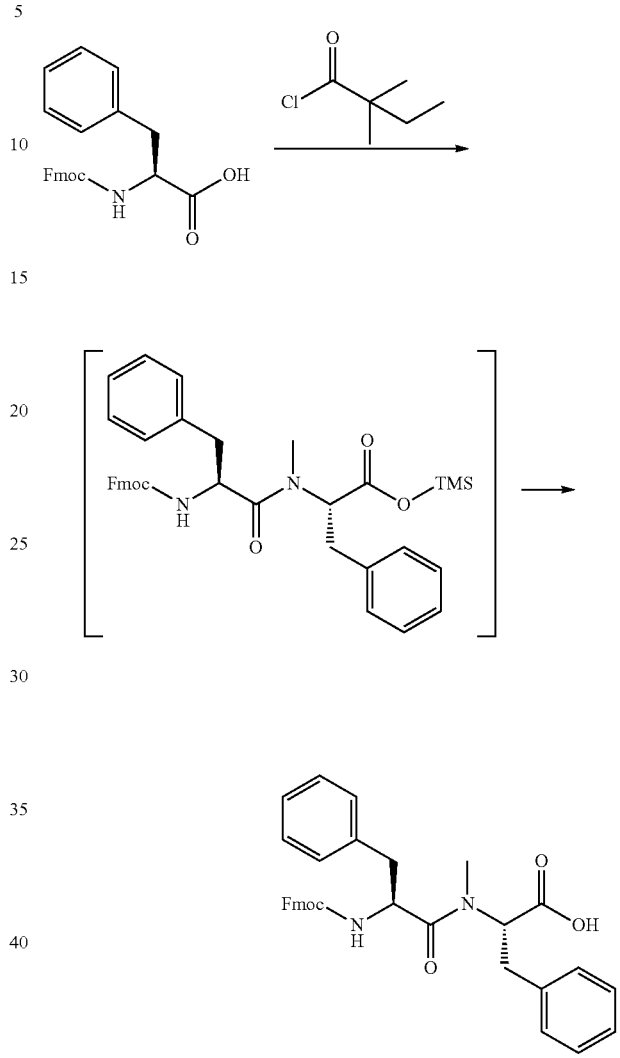

Fmoc-Phe-OH (0.194 g, 0.500 mmol) and triethylamine (0.0607 g, 0.60 mmol) were mixed with tetrahydrofuran (10 mL), and 2,2-dimethylbutanoyl chloride (0.074 g, 0.550 mmol) was added to the mixture at 0° C. and the resulting mixture was stirred for 1 hour. To the solution was added a solution which had been separately prepared by mixing H-MePhe-OH (0.108 g, 0.600 mmol), N,N'-bis(trimethylsilyl)urea (0.250 g, 1.20 mmol) and acetonitrile (4.0 mL) and stirring the mixture at 75° C. for 60 minutes under microwave irradiation, and the resulting mixture was further stirred at 25° C. for 67 hours (starting material:target compound=1:20 (Analytical condition 2)). The obtained reaction mixture was concentrated and then diluted with ethyl acetate (80 mL), and successively washed with a 10 wt % aqueous citric acid solution (50 mL), 5 wt % aqueous sodium chloride solution (50 mL) and a saturated aqueous sodium chloride solution (50 mL). The obtained organic layer was concentrated to obtain Fmoc-Phe-MePhe-OH (0.322 g, yield: 117%) as a white solid.

MASS (ESI+) m/z; (M+H)+549.4

Synthetic Example 12: Synthesis of Fmoc-Phe-MePhe-OH

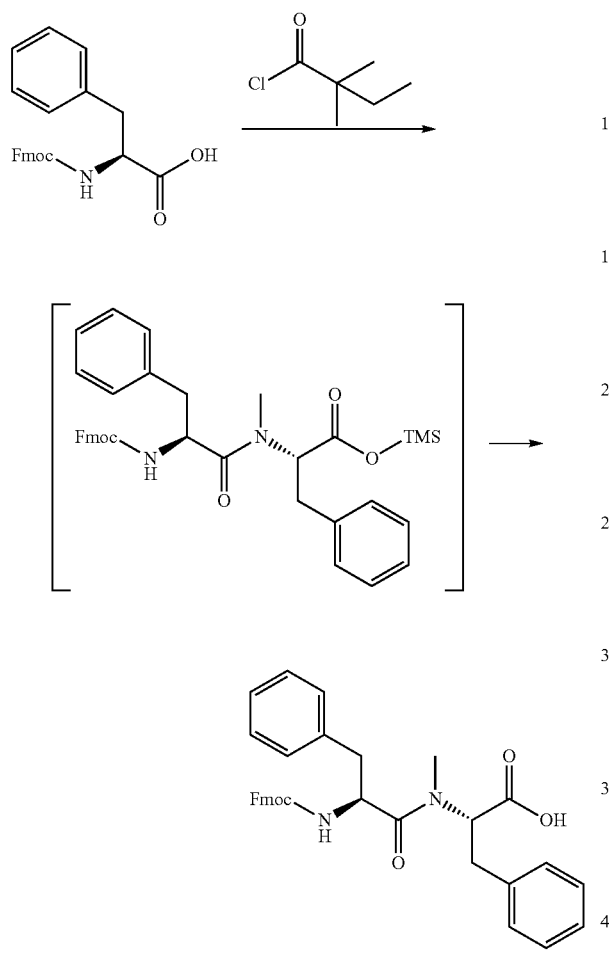

Synthetic Example 13: Synthesis of Boc-MePhe-MePhe-OH

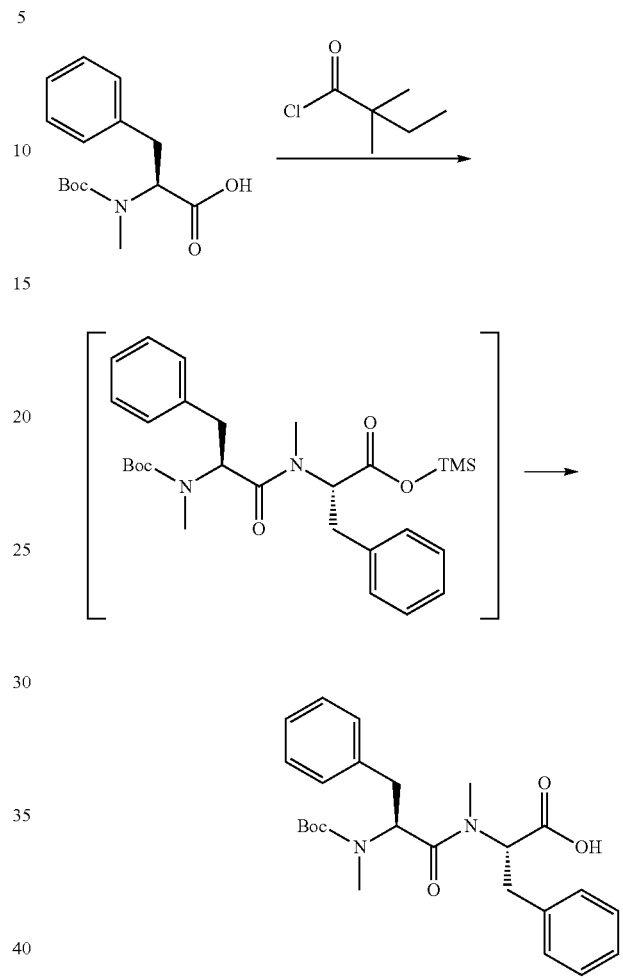

Fmoc-Phe-OH (0.097 g, 0.250 mmol) and triethylamine (0.0304 g, 0.300 mmol) were mixed with tetrahydrofuran (5 mL), and 2,2-dimethylbutanoyl chloride (0.0371 g, 0.275 mmol) was added to the mixture at 0° C. and the resulting mixture was stirred for 1 hour. To the solution was added a solution which had been separately prepared by mixing H-MePhe-OH (0.0538 g, 0.300 mmol), N,O-bis(trimethylsilyl)-trifluoroacetamide (0.155 g, 0.601 mmol) and acetonitrile (4.0 mL) and stirring the mixture at 75° C. for 30 minutes, and the resulting mixture was further stirred at 25° C. for 16 hours (starting material:target compound=4.4:95.6 (Analytical condition 1; provided that at the time of stirring for 4 hours)). The obtained reaction mixture was concentrated and then diluted with ethyl acetate (20 mL), and successively washed with a saturated aqueous sodium hydrogen carbonate solution (20 mL), water (20 mL) and a saturated aqueous sodium chloride solution (10 mL). The obtained organic layer was successively washed with a 10 wt % aqueous citric acid solution (20 mL) and a saturated aqueous sodium chloride solution (20 mL). The obtained organic layer was concentrated to obtain Fmoc-Phe-MePhe-OH (0.135 g, yield: 98%) as a white solid.

MASS (ESI+) m/z; (M+H)+549.4

Boc-MePhe-OH (0.070 g, 0.250 mmol) and triethylamine (0.033 g, 0.32 mmol) were mixed with tetrahydrofuran (5 mL), and 2,2-dimethylbutanoyl chloride (0.040 g, 0.30 mmol) was added to the mixture at 0° C. and the resulting mixture was stirred for 1 hour. To the solution was added a solution which had been separately prepared by mixing H-MePhe-OH (0.067 g, 0.38 mmol), N,O-bis(trimethylsilyl)acetamide (0.161 g, 0.774 mmol) and acetonitrile (4.0 mL) and stirring the mixture at 75° C. for 3 minutes, and the resulting mixture was further stirred at 25° C. for 16 hours (starting material:target compound=7:93 (Analytical condition 1)). The obtained reaction mixture was concentrated and then diluted with ethyl acetate (20 mL), and successively washed with a saturated aqueous sodium hydrogen carbonate solution (20 mL), water (20 mL) and a saturated aqueous sodium chloride solution (10 mL). The obtained organic layer was successively washed with a 10 wt % aqueous citric acid solution (20 mL) and a saturated aqueous sodium chloride solution (20 mL). The obtained organic layer was concentrated and the concentrate was purified by silica gel column chromatography to obtain Boc-MePhe-MePhe-OH (0.127 g, yield: 116%) as colorless oil.

MASS (ESI+) m/z; (M+H)+441.4

Synthetic Example 14: Synthesis of Boc-MePhe-Phe-OH

Synthetic Example 15: Synthesis of Fmoc-MePhe-Phe-OH

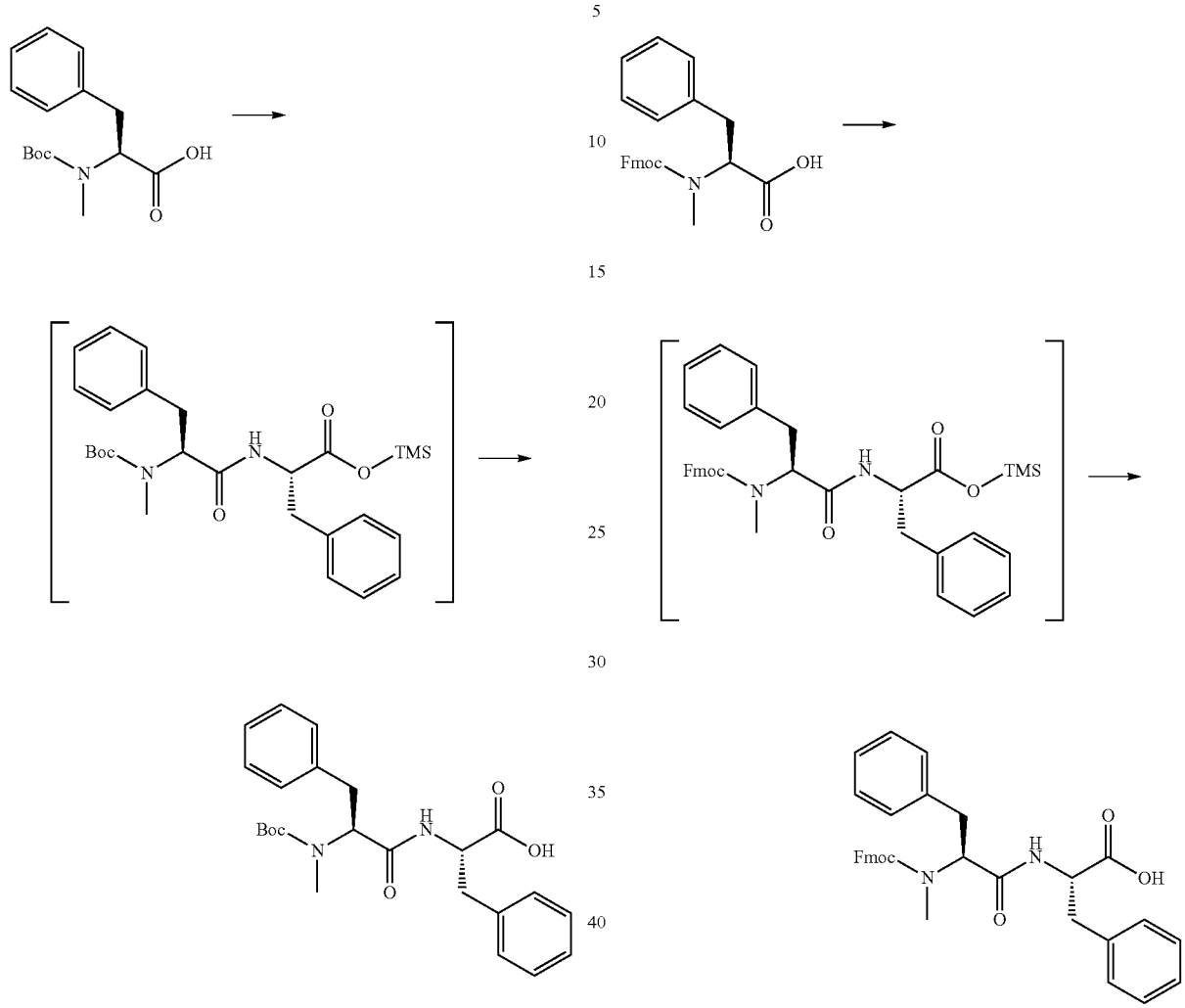

Boc-MePhe-OH (1.40 g, 5.00 mmol) and N-methylmorpholine (0.556 g, 5.50 mmol) were mixed with tetrahydrofuran (50 mL), isopropyl chloroformate (0.643 g, 5.25 mmol) was added to the mixture at 0° C. and the resulting mixture was stirred for 15 minutes. To the solution was added a solution which had been separately prepared by mixing H-Phe-OH (0.991 g, 6.00 mmol), N,O-bis(trimethylsilyl)acetamide (2.57 g, 12.4 mmol) and acetonitrile (15 mL) and stirring the mixture at 75° C. for 60 minutes under microwave irradiation, the mixture was stirred for 30 minutes while maintaining to 0° C., and the resulting mixture was further stirred at 25° C. for 1.5 hours (starting material:target compound=0:100 (Analytical condition 1)). The obtained reaction mixture was diluted with ethyl acetate (200 mL), and successively washed with a 10 wt % aqueous citric acid solution (75 mL), a 5 wt % aqueous sodium chloride solution (75 mL) and a saturated aqueous sodium chloride solution (75 mL). The obtained organic layer was concentrated and the concentrate was purified by silica gel column chromatography to obtain Boc-MePhe-Phe-OH (2.20 g, yield: 103%) as a white solid.

MASS (ESI+) m/z; (M+H)+427.3

Fmoc-MePhe-OH (2.00 g, 5.00 mmol) and N-methylmorpholine (0.556 g, 5.50 mmol) were mixed with tetrahydrofuran (30 mL), isopropyl chloroformate (0.663 g, 5.25 mmol) was added to the mixture at 0° C. and the resulting mixture was stirred for 30 minutes. To the solution was added a solution which had been separately prepared by mixing H-Phe-OH (0.991 g, 6.00 mmol), N,O-bis(trimethylsilyl)acetamide (2.68 g, 12.9 mmol) and acetonitrile (15 mL) and stirring the mixture at 75° C. for 30 minutes, the mixture was stirred for 50 minutes while maintaining to 0° C., and the resulting mixture was further stirred at 25° C. for 1 hour (starting material:target compound=3:97 (Analytical condition 1)). The obtained reaction mixture was diluted with ethyl acetate (75 mL), and successively washed with a 10 wt % aqueous citric acid solution (50 mL), a 5 wt % aqueous sodium chloride solution (50 mL) and a saturated aqueous sodium chloride solution (50 mL). The obtained organic layer was concentrated and the concentrate was purified by silica gel column chromatography to obtain Fmoc-MePhe-Phe-OH (2.85 g, yield: 98%) as a white solid.

MASS (ESI+) m/z; (M+H)+549.4

Synthetic Example 16: Synthesis of H-MePhe-Phe-OH

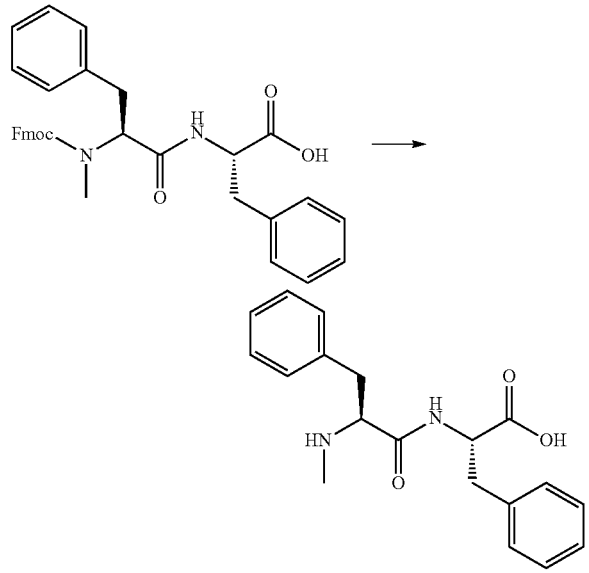

Fmoc-MePhe-Phe-OH (0.137 g, 0.250 mmol) and triethylamine (0.505 g, 4.99 mmol) were mixed with acetonitrile (4.4 mL), and the resulting mixture was stirred at 80° C. for 60 minutes. The obtained reaction mixture was concentrated, tetrahydrofuran (1.0 mL) and diisopropyl ether (3.0 mL) were added to the concentrate to suspend the same, and the generated solid was collected by Kiriyama funnel. The solid was washed with diisopropyl ether (5 mL) and dried to obtain H-MePhe-Phe-OH (0.071 g, yield: 87%) as a white solid.

MASS (ESI+) m/z; (M+H)+327.3

Synthetic Example 17: Synthesis of H-MePhe-Phe-OH·HCl

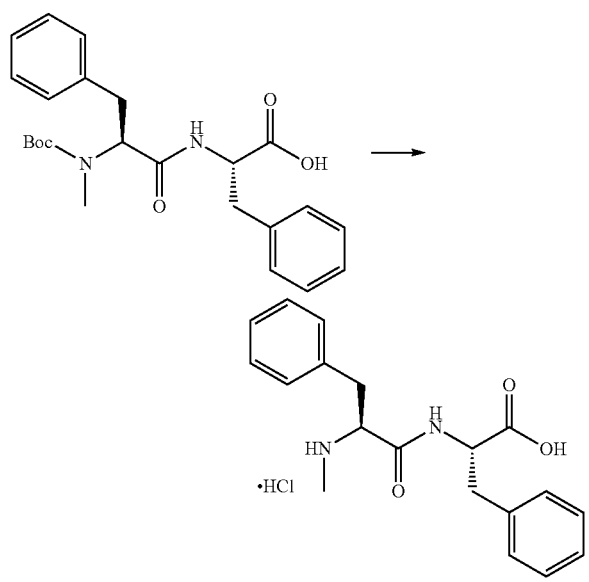

Boc-MePhe-Phe-OH (0.213 g, 0.500 mmol) was mixed with 4M-HCl/ethyl acetate (10 mL), and the resulting mixture was stirred at 25° C. for 1 hour. The obtained reaction mixture was concentrated, diisopropyl ether was added to the concentrate to suspend the same, and the generated solid was collected by Kiriyama funnel and dried to obtain H-MePhe-Phe-OH·HCl (0.164 g, yield: 91%) as a white solid.

MASS (ESI+) m/z; (M+H)+327.3

Synthetic Example 18: Synthesis of Boc-MePhe-MePhe-Phe-OH

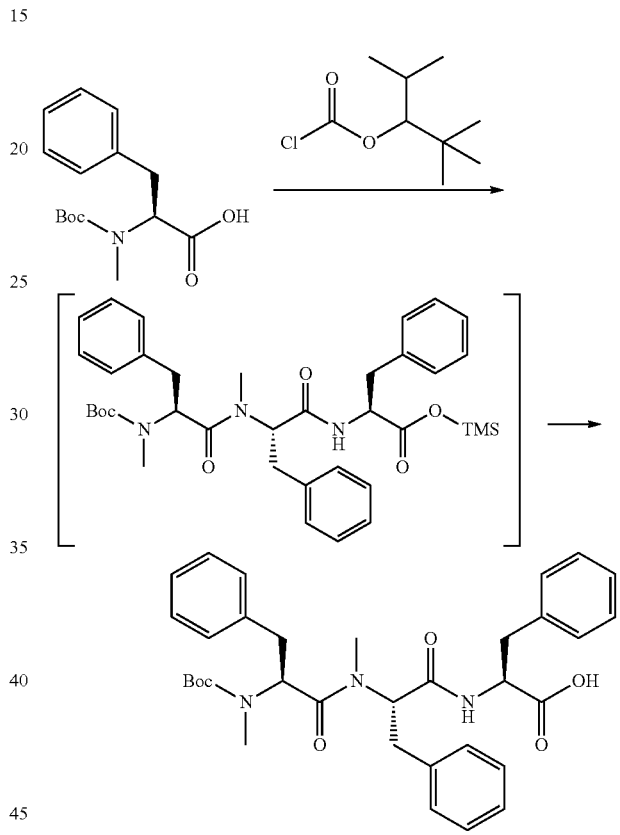

Solution A

Boc-MePhe-OH (0.280 g, 1.00 mmol) and N-methylmorpholine (0.112 g, 1.10 mmol) were mixed with tetrahydrofuran (10 mL), and 2,2,4-trimethylpentan-3-yl carbonochloridate (0.203 g, 1.05 mmol) was added to the mixture at 0° C. and the resulting mixture was stirred for 1 hour.

Solution B

Boc-MePhe-Phe-OH (0.449 g, 1.05 mmol) was mixed with 4M-HCl/cyclopentyl methyl ether (5 mL), and the resulting mixture was stirred at 25° C. for 30 minutes. The obtained reaction mixture was concentrated, ethyl acetate (20 mL) was added to the concentrate and the mixture was concentrated, and N,N-diisopropyl-ethylamine (1.30 g, 10.0 mmol) and acetonitrile (8 mL) were added to the concentrate and the mixture was concentrated. The obtained residue was mixed with acetonitrile (10 mL) and N,O-bis(trimethylsilyl) acetamide (0.644 g, 3.11 mmol), and the resulting mixture was stirred at 25° C. for 20 minutes to obtain a colorless transparent solution.

Condensation Step

While maintaining Solution A to 0° C., Solution B was mixed therewith, and the resulting mixture was further stirred for at 18 hours while maintaining to 25° C. (starting material:target compound=1:21 (Analytical condition 3)). The obtained reaction mixture was diluted with ethyl acetate (40 mL), and successively washed with a 10 wt % aqueous citric acid solution and a saturated aqueous sodium chloride solution. The obtained organic layer was concentrated and the concentrate was purified by silica gel column chromatography to obtain Boc-Phe-MePhe-MePhe-MePhe-OH (0.532 g, yield: 90%) as a white solid. MASS (ESI+) m/z; (M+H)+588.4

Synthetic Example 19: Synthesis of Boc-Phe-MePhe-MePhe-Phe-OH

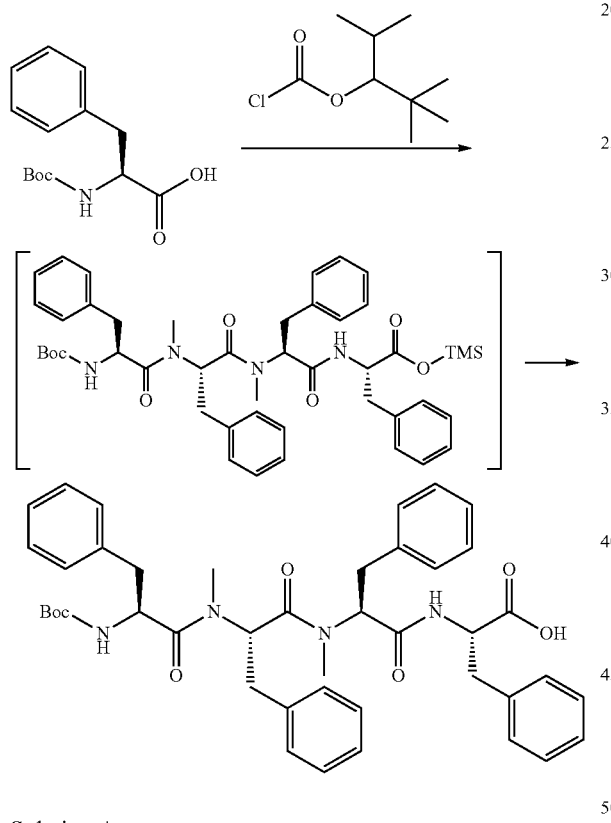

Solution A

Boc-Phe-OH (0.177 g, 0.669 mmol) and N-methylmorpholine (0.744 g, 0.736 mmol) were mixed with tetrahydrofuran (10 mL), 2,2,4-trimethylpentan-3-yl carbonochloridate (0.135 g, 0.702 mmol) was added to the mixture at 0° C. and the resulting mixture was stirred for 1 hour.

Solution B

Boc-MePhe-MePhe-Phe-OH (0.413 g, 0.702 mmol) was mixed with 4M-HCl/cyclopentyl methyl ether (10 mL), and the resulting mixture was stirred at 25° C. for 1 hour. The obtained reaction mixture was concentrated, ethyl acetate (20 mL) was added to the concentrate and the mixture was concentrated, and N,N-diisopropyl-ethylamine (0.865 g, 6.69 mmol) and acetonitrile (8 mL) were added to the concentrate and the mixture was concentrated. The obtained residue was mixed with acetonitrile (10 mL) and N,O-bis(trimethylsilyl)acetamide (0.430 g, 2.07 mmol), and the resulting mixture was stirred at 25° C. for 20 minutes to obtain a colorless transparent solution.

Condensation Step

While maintaining Solution A to 0° C., Solution B was mixed therewith, and the resulting mixture was further stirred for 18 hours while maintaining to 25° C. (starting material:target compound=0:100 (Analytical condition 3)). The obtained reaction mixture was diluted with ethyl acetate (20 mL), and successively washed with a 10 wt % aqueous citric acid solution (20 mL), a 10 wt % aqueous sodium chloride solution (20 mL) and a saturated aqueous sodium chloride solution (20 mL). The obtained organic layer was concentrated and the concentrate was purified by silica gel column chromatography to obtain Boc-Phe-MePhe-MePhe-Phe-OH (0.453 g, yield: 92%) as a white solid.

MASS (ESI+) m/z; (M+H)+735.5

Synthetic Example 20: Synthesis of Boc-MePhe-MePhe-Phe-OH

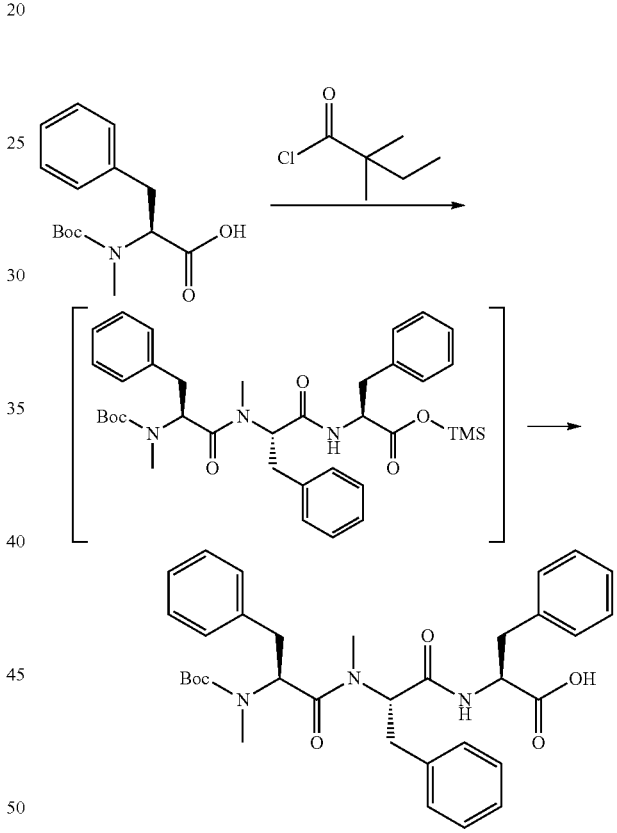

Solution A

Boc-MePhe-OH (0.324 g, 1.16 mmol) and triethylamine (0.141 g, 1.39 mmol) were mixed with tetrahydrofuran (10 mL), 2,2-dimethylbutanoyl chloride (0.172 g, 1.28 mmol) was added to the mixture at 0° C. and the resulting mixture was stirred for 1 hour.

Solution B

Boc-MePhe-Phe-OH (0.544 g, 1.28 mmol) was mixed with 4M-HCl/cyclo-pentyl methyl ether (20 mL), and the resulting mixture was stirred at 25° C. for 1 hour. The obtained reaction mixture was concentrated, cyclopentyl methyl ether (20 mL) was added to the concentrate and the mixture was concentrated, and N,N-diisopropylethyl-amine (1.50 g, 11.6 mmol) and acetonitrile (8 mL) were added to the concentrate and the mixture was concentrated. The obtained residue was mixed with acetonitrile (10 mL) and N,O-bis(trimethylsilyl)acetamide (0.621 g, 2.99 mmol), the mixture was stirred at 25° C. for 20 minutes to obtain a colorless transparent solution.

Condensation Step

While maintaining Solution A to 0° C., Solution B was mixed therewith, and the resulting mixture was further stirred for at 48 hours while maintaining to 25° C. (starting material:target compound=1:37 (Analytical condition 3)). The obtained reaction mixture was diluted with ethyl acetate (40 mL), and successively washed with a 10 wt % aqueous citric acid solution and a saturated aqueous sodium chloride solution. The obtained organic layer was concentrated and the concentrate was purified by silica gel column chromatography to obtain Boc-MePhe-MePhe-Phe-OH (0.701 g, yield: 103%) as a brown solid.

MASS (ESI+) m/z; (M+H)+588.4

Synthetic Example 21: Synthesis of Boc-MePhe-Pro-OH

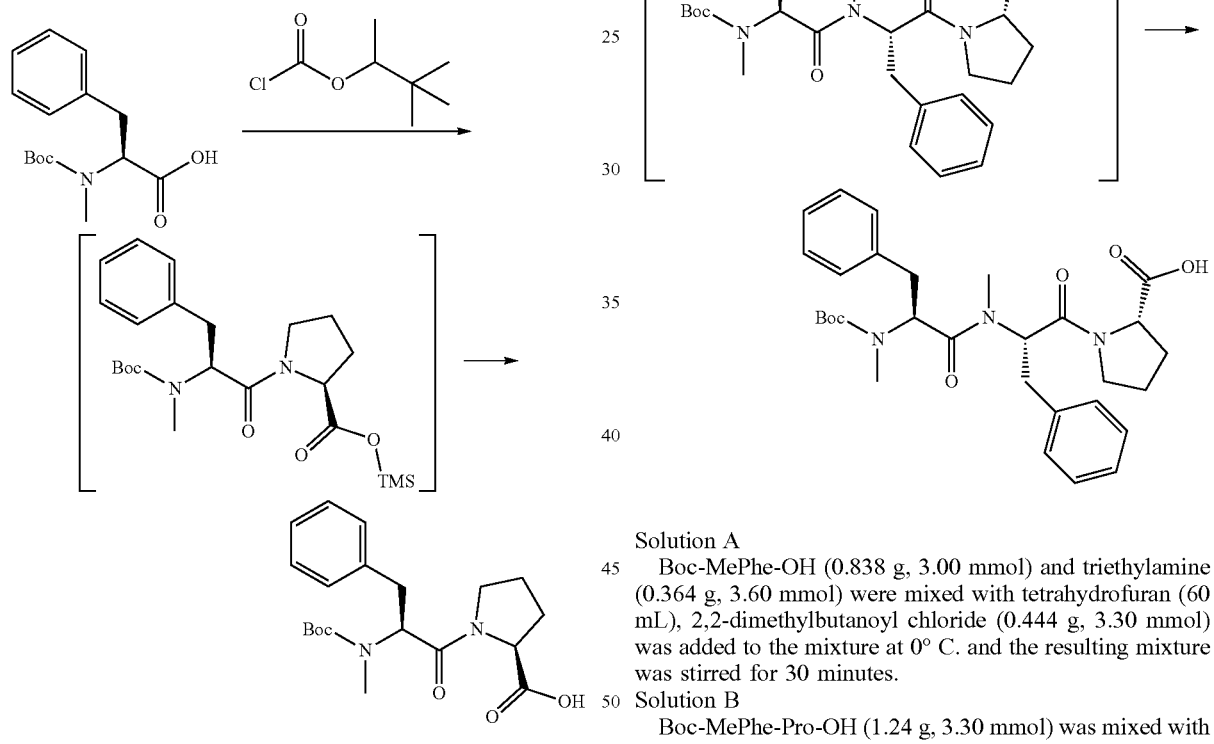

Boc-MePhe-OH (1.40 g, 5.00 mmol) and N-methylmorpholine (0.556 g, 5.50 mmol) were mixed with tetrahydrofuran (30 mL), 3,3-dimethylbutan-2-yl carbono-chloridate (0.864 g, 5.25 mmol) was added to the mixture at 0° C. and the resulting mixture was stirred for 1 hour. To the solution was added a solution which had been separately prepared by mixing H-Pro-OH (0.691 g, 6.00 mmol), N,O-bis(trimethylsilyl)acetamide (3.85 g, 18.6 mmol) and acetonitrile (12 mL) and stirring the mixture at 70° C. for 10 minutes, and the resulting mixture was further stirred at 0° C. for 15 minutes (starting material:target compound=0:100 (Analytical condition 3)). The obtained reaction mixture was diluted with ethyl acetate (40 mL), and successively washed with a 10 wt % aqueous citric acid solution and a saturated aqueous sodium chloride solution. The obtained organic layer was concentrated and the concentrate was purified by silica gel column chromatography to obtain Boc-MePhe-Pro-OH (1.94 g, yield: 94%) as a white solid.

MASS (ESI+) m/z; (M+H)+377.3

Synthetic Example 22: Synthesis of Boc-MePhe-MePhe-Pro-OH

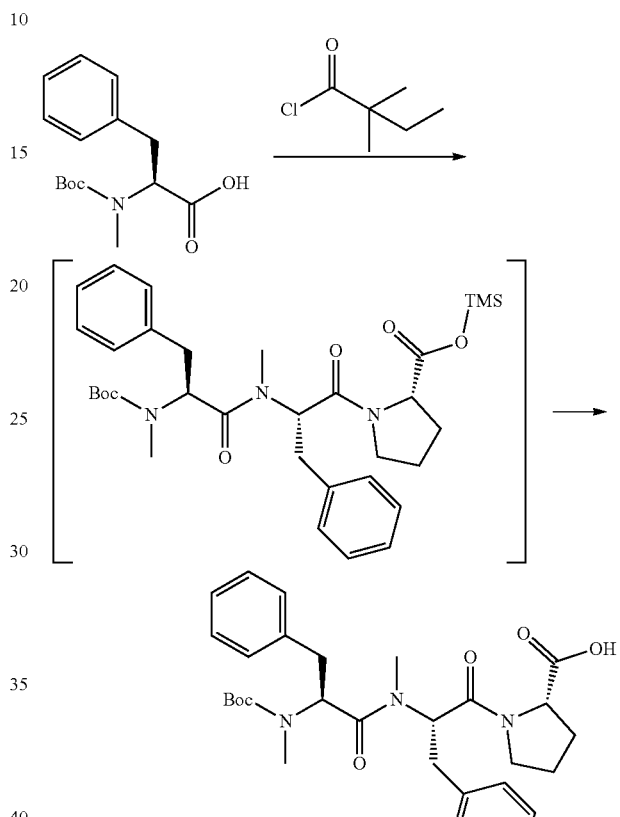

Solution A

Boc-MePhe-OH (0.838 g, 3.00 mmol) and triethylamine (0.364 g, 3.60 mmol) were mixed with tetrahydrofuran (60 mL), 2,2-dimethylbutanoyl chloride (0.444 g, 3.30 mmol) was added to the mixture at 0° C. and the resulting mixture was stirred for 30 minutes.

Solution B

Boc-MePhe-Pro-OH (1.24 g, 3.30 mmol) was mixed with 4M-HCl/cyclopentyl methyl ether (20 mL), and the resulting mixture was stirred at 25° C. for 1 hour. The obtained reaction mixture was concentrated, acetonitrile (20 mL) was added to the concentrate and the mixture was concentrated, and N,N-diisopropylethylamine (0.865 g, 6.69 mmol) and acetonitrile (20 mL) were added to the concentrate and the mixture was concentrated. The obtained residue was mixed with acetonitrile (20 mL) and N,O-bis(trimethylsilyl)acetamide (2.31 g, 11.1 mmol), and the resulting mixture was stirred at 25° C. for 20 minutes to obtain a colorless transparent solution.

Condensation Step

While maintaining Solution A to 0° C., Solution B was mixed therewith, and the resulting mixture was further stirred for 48 hours while maintaining to 25° C. (starting material:target compound=1:24 (Analytical condition 3)).

The obtained reaction mixture was diluted with ethyl acetate (40 mL), and successively washed with a 10 wt % aqueous citric acid solution and a saturated aqueous sodium chloride solution. The obtained organic layer was concentrated and the concentrate was purified by silica gel column chromatography to obtain Boc-MePhe-MePhe-Pro-OH (1.71 g, yield: 90%) as a white solid.

MASS (ESI+) m/z; (M+H)+538.5

Synthetic Example 23: Synthesis of H-MePhe-MePhe-Pro-OH·HCl

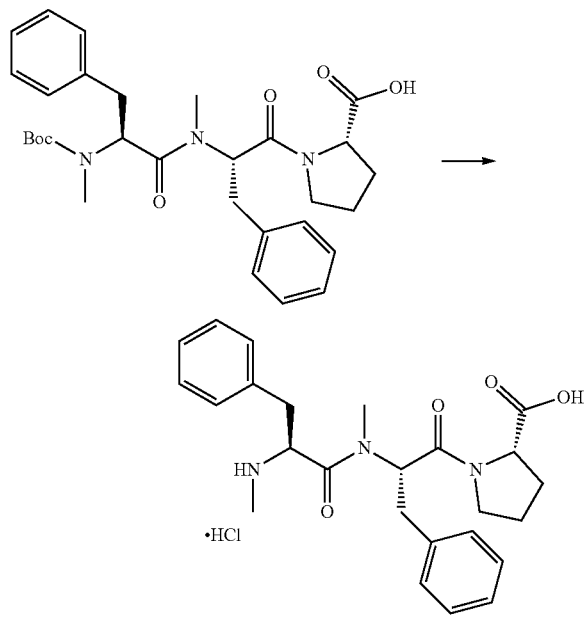

Boc-MePhe-MePhe-Pro-OH (1.61 g, 3.00 mmol) was mixed with 4M-HCl/ethyl acetate (15 mL), and the resulting mixture was stirred at 25° C. for 90 minutes. The obtained reaction mixture was concentrated, ethyl acetate (5 mL), diisopropyl ether (20 mL) were added to the concentrate to suspend the same, and the generated solid was collected by Kiriyama funnel. The solid was washed with diisopropyl ether (10 mL) and dried to obtain H-MePhe-MePhe-Pro-OH·HCl (1.30 g, yield: 91%) as a white solid. The obtained solid was used in the next step.

Synthetic Example 24: Synthesis of Boc-Tyr-MePhe-MePhe-Pro-OH

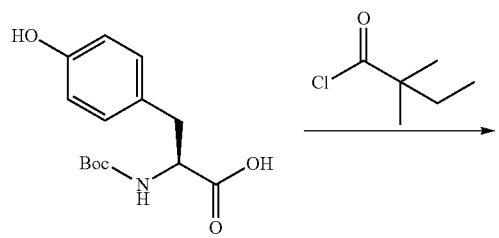

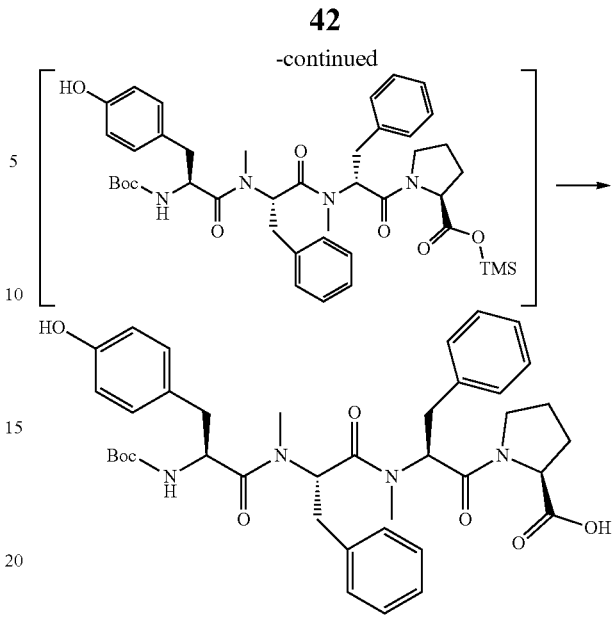

Solution A

Boc-Tyr-OH (0.282 g, 1.00 mmol) and triethylamine (0.122 g, 1.20 mmol) were mixed with tetrahydrofuran (10 mL), 2,2-dimethylbutanoyl chloride (0.148 g, 1.10 mmol) was added to the mixture at 0° C. and the resulting mixture was stirred for 1 hour.

Solution B

H-MePhe-MePhe-Pro-OH·HCl (0.482 g, 1.02 mmol) was mixed with N,N-diisopropylethylamine (2 mL), and the resulting mixture was stirred at 25° C. for 2 minutes. The obtained reaction mixture was concentrated. The obtained residue was mixed with acetonitrile (6 mL) and N,O-bis(trimethylsilyl)acetamide (0.773 g, 3.74 mmol), and the resulting mixture was stirred at 25° C. for 20 minutes to obtain a colorless transparent solution.

Condensation Step

While maintaining Solution A to 0° C., Solution B was mixed therewith, and the resulting mixture was further stirred for 1 hour while maintaining to 25° C. The obtained reaction mixture was diluted with ethyl acetate (40 mL), and successively washed with a 10 wt % aqueous citric acid solution and a saturated aqueous sodium chloride solution. The obtained organic layer was concentrated and the concentrate was purified by silica gel column chromatography to obtain Boc-Tyr-MePhe-MePhe-Pro-OH (0.698 g, yield: 99%) as a white solid.

MASS (ESI+) m/z; (M+H)+701.5

Synthetic Example 25: Synthesis of Boc-MePhe-MeAla-Tyr-OH

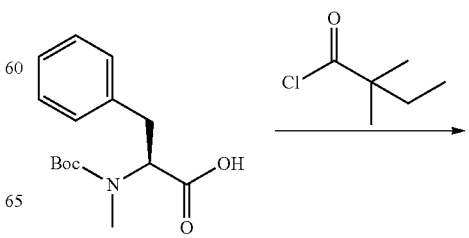

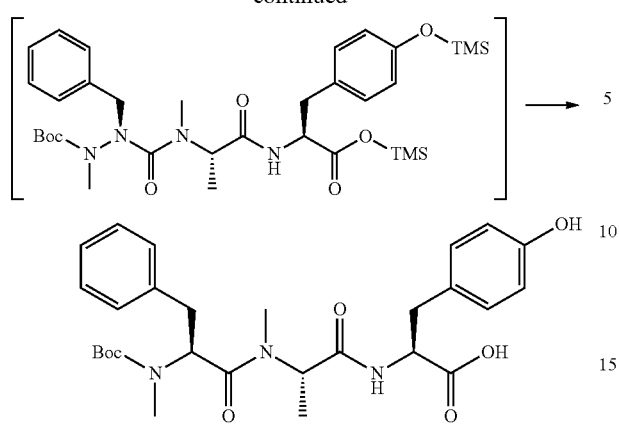

Solution A

Boc-MePhe-OH (0.894 g, 3.20 mmol) and triethylamine (0.389 g, 3.84 mmol) were mixed with tetrahydrofuran (25 mL), 2,2-dimethylbutanoyl chloride (0.474 g, 3.52 mmol) was added to the mixture at 0° C. and the resulting mixture was stirred for 45 minutes.

Solution B

H-MeAla-Tyr-OH (0.937 g, 3.52 mmol) was mixed with acetonitrile (10 mL) and N,O-bis(trimethylsilyl)acetamide (2.28 g, 10.9 mmol), and the resulting mixture was stirred at 25° C. for 15 minutes to obtain a colorless transparent solution.

Condensation Step

While maintaining Solution A to 0° C., Solution B was mixed therewith, and the resulting mixture was further stirred for 2 hours while maintaining to 25° C. (starting material:target compound=0:100 (Analytical condition 1)). The obtained reaction mixture was concentrated and then diluted with ethyl acetate (30 mL), and successively washed with a saturated aqueous sodium hydrogen carbonate solution (20 mL), water (20 mL) and a saturated aqueous sodium chloride solution (10 mL). The obtained organic layer was successively washed with a 10 wt % aqueous citric acid solution (20 mL) and a saturated aqueous sodium chloride solution. The obtained organic layer was concentrated and the concentrate was purified by silica gel column chromatography to obtain Boc-MePhe-MeAla-Tyr-OH (1.67 g, yield: 94%) as a white solid.

MASS (ESI+) m/z; (M+H)+528.3

Synthetic Example 26: Synthesis of H-MePhe-MeAla-Tyr-OH

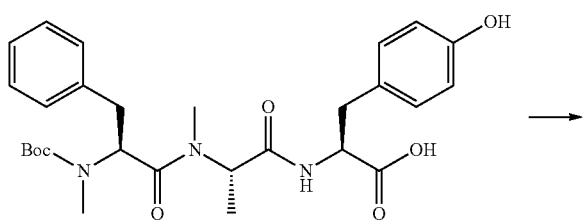

Boc-MePhe-MeAla-Tyr-OH (0.474 g, 0.898 mmol) was mixed with 4M-HCl/ethyl acetate (5 mL), and the resulting mixture was stirred at 25° C. for 60 minutes. The obtained reaction mixture was concentrated, acetonitrile (5 mL) and N,N-diiso-propylethylamine (1.74 g, 13.5 mmol) were added to the concentrate to suspend the same, and the generated solid was collected by Kiriyama funnel. The solid was washed with a solution of N,N-diisopropylethylamine (1.74 g, 13.5 mmol) and diisopropyl ether (5 mL) and dried to obtain H-MePhe-MeAla-Tyr-OH (0.370 g, yield: 96%) as a white solid.

MASS (ESI+) m/z; (M+H)+428.8

Synthetic Example 27: Synthesis of Boc-Phe-MePhe-MeAla-Tyr-OH

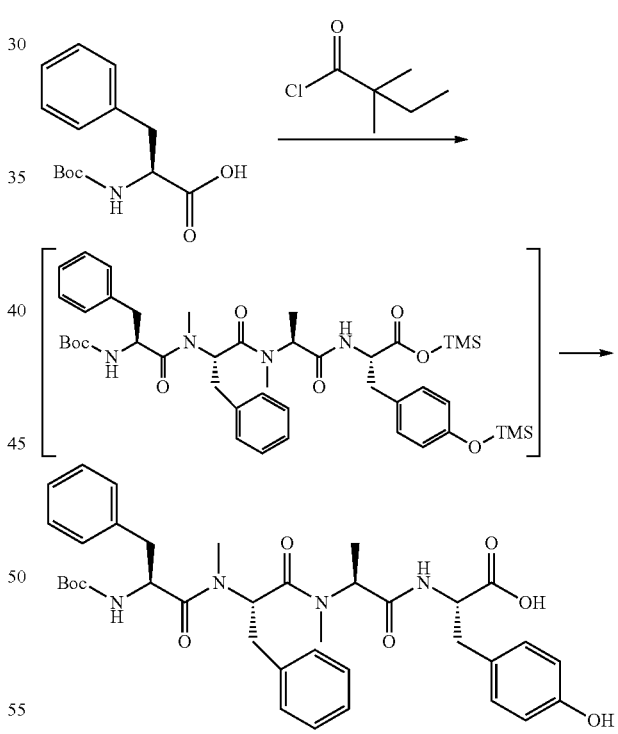

Boc-Phe-OH (0.125 g, 0.470 mmol) and triethylamine (0.057 g, 0.564 mmol) were mixed with tetrahydrofuran (5.0 mL), 2,2-dimethylbutanoyl chloride (0.070 g, 0.52 mmol) was added to the mixture at 0° C. and the resulting mixture was stirred for 45 minutes. To the solution was added a solution which had been separately prepared by mixing H-MePhe-MeAla-Tyr-OH (0.221 g, 0.517 mmol), N,O-bis(trimethylsilyl)-acetamide (0.332 g, 1.60 mmol) and acetonitrile (5.0 mL) and stirring the mixture at 25° C. for 15 minutes, and the resulting mixture was further stirred for 2 hours while maintaining to 25° C. (starting material:target compound=1:80 (Analytical condition 2)). The obtained reaction mixture was concentrated and then diluted with ethyl acetate (40 mL), and successively washed with a 10 wt % aqueous citric acid solution and a saturated aqueous sodium chloride solution. The obtained organic layer was concentrated and the concentrate was purified by silica gel column chromatography to obtain Boc-Phe-MePhe-MeAla-Tyr-OH (0.295 g, yield: 93%) as a white solid. MASS (ESI+) m/z; (M+H)+675.5

Synthetic Example 28: Synthesis of H-Phe-MePhe-MeAla-Tyr-OH

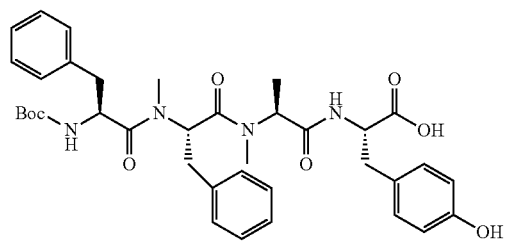

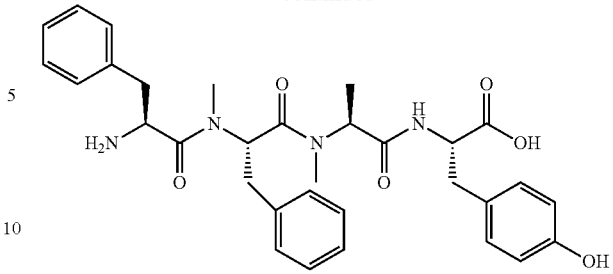

Boc-Phe-MePhe-MeAla-Tyr-OH (0.317 g, 0.470 mmol) was mixed with trifluoroacetic acid (1.45 mL), and the resulting mixture was stirred at 25° C. for 15 minutes. The obtained reaction mixture was concentrated, acetonitrile (7 mL) and triethylamine (0.476 g, 4.70 mmol) were added to the concentrate to suspend the same, and the generated solid was collected by Kiriyama funnel. The solid was washed with ethyl acetate (2 mL) and diisopropyl ether (8 mL) and dried to obtain H-Phe-MePhe-MeAla-Tyr-OH (0.268 g, yield: 99%) as a white solid.

MASS (ESI+) m/z; (M+H)+575.4

Synthetic Example 29: Synthesis of Boc-MePhe-Phe-MePhe-MeAla-Tyr-OH

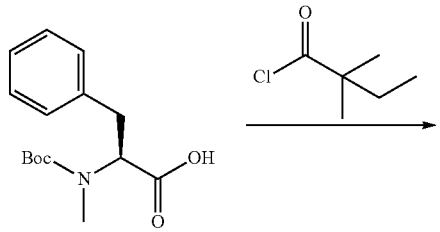

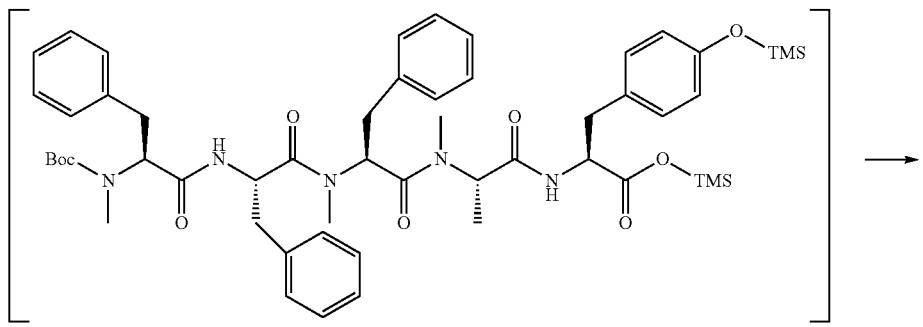

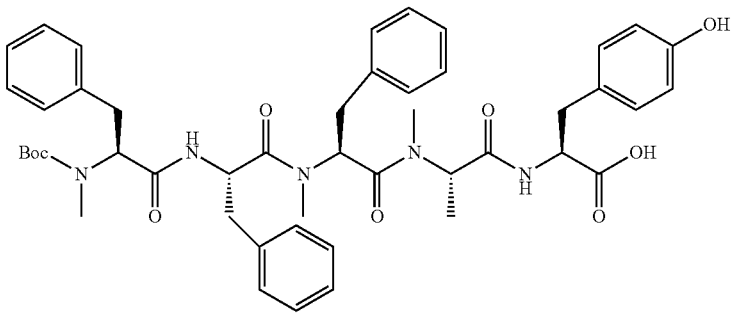

Boc-MePhe-OH (0.092 g, 0.33 mmol) and triethylamine (0.040 g, 0.396 mmol) were mixed with tetrahydrofuran (5.0 mL), 2,2-dimethylbutanoyl chloride (0.0489 g, 0.363 mmol) was added to the mixture at 0° C. and the resulting mixture was stirred for 45 minutes. To the solution was added a solution which had been separately prepared by mixing H-Phe-MePhe-MeAla-Tyr-OH (0.209 g, 0.363 mmol), N,O-bis(trimethyl-silyl)acetamide (0.233 g, 1.12 mmol) and acetonitrile (5.0 mL) and stirring the mixture at 25° C. for 15 minutes, and the resulting mixture was further stirred for 1 hour while maintaining to 25° C. (starting material:target compound=0:100 (Analytical condition 2)). The obtained reaction mixture was concentrated and then diluted with ethyl acetate (40 mL), and successively washed with a 10 wt % aqueous citric acid solution and a saturated aqueous sodium chloride solution. The obtained organic layer was concentrated and the concentrate was purified by silica gel column chromatography to obtain Boc-MePhe-Phe-MePhe-MeAla-Tyr-OH (0.282 g, yield: 87%) as a white solid. MASS (ESI+) m/z; (M+H)+836.5

Synthetic Example 30: Synthesis of Cbz-MeAla-Phe-OH

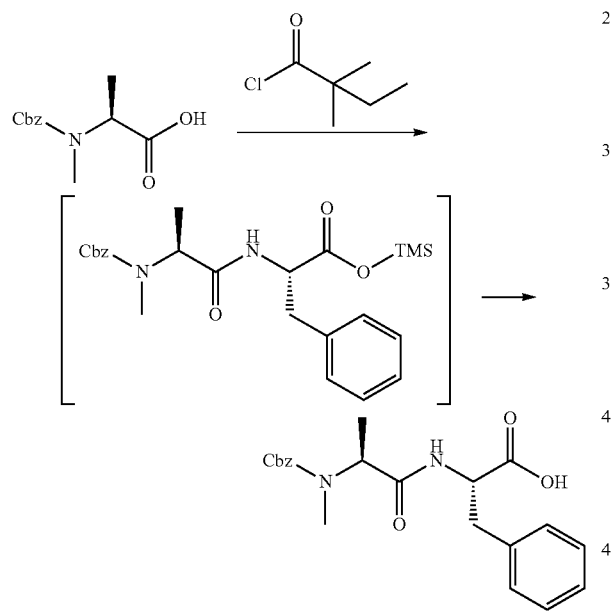

Cbz-MeAla-OH (1.19 g, 5.00 mmol) and triethylamine (0.607 g, 6.00 mmol) were mixed with tetrahydrofuran (50 mL), 2,2-dimethylbutanoyl chloride (0.740 g, 5.50 mmol) was added to the mixture at 0° C. and the resulting mixture was stirred for 45 minutes. To the solution was added a solution which had been separately prepared by mixing H-Phe-OH (0.991 g, 6.00 mmol), N,O-bis(trimethylsilyl) acetamide (2.57 g, 12.4 mmol) and acetonitrile (17 mL) and stirring the mixture at 75° C. for 60 minutes under microwave irradiation, and the resulting mixture was further stirred for 1 hour while maintaining to 0° C. (starting material:target compound=1:62 (Analytical condition 1)). The obtained reaction mixture was concentrated and then diluted with ethyl acetate (40 mL), and successively washed with a saturated aqueous sodium hydrogen carbonate solution (60 mL), water (60 mL) and a saturated aqueous sodium chloride solution (30 mL). The obtained organic layer was successively washed with a 10 wt % aqueous citric acid solution (30 mL) and a saturated aqueous sodium chloride solution (30 mL). The obtained organic layer was concentrated to obtain Cbz-MeAla-Phe-OH (1.76 g, yield: 91%) as colorless transparent syrup.

MASS (ESI+) m/z; (M+H)+385.3

Synthetic Example 31: Synthesis of H-MeAla-Phe-OH

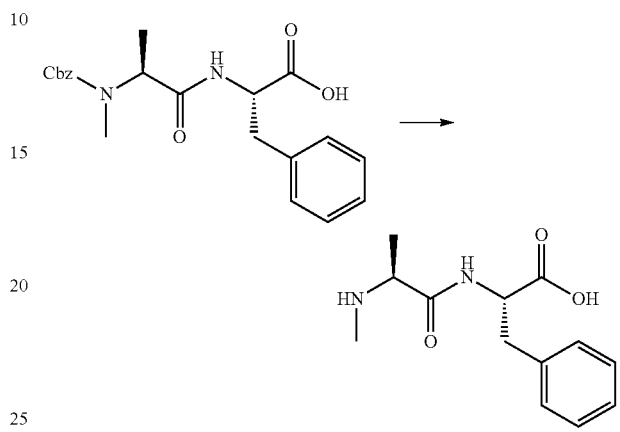

Cbz-MeAla-Phe-OH (1.76 g, 4.57 mmol), triethylamine (0.023 g, 0.229 mmol), ammonium formate (1.44 g, 22.9 mmol) and 10 wt % palladium-carbon (0.486 g) were mixed with methanol (50 mL), and the resulting mixture was stirred at 60° C. for 1 hour. The reaction solution was filtered through Celite, and washed with methanol (20 mL) three times. The obtained filtrate was concentrated to obtain H-MeAla-Phe-OH (1.03 g, 90%) as a white solid.

MASS (ESI+) m/z; (M+H)+251.2

Synthetic Example 32: Synthesis of Boc-MePhe-MeAla-Phe-OH

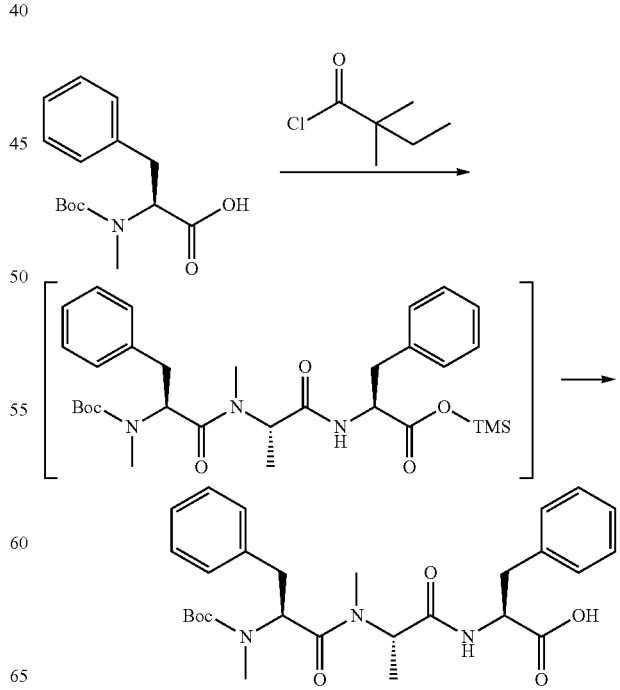

Boc-MePhe-OH (0.559 g, 2.00 mmol) and triethylamine (0.243 g, 2.40 mmol) were mixed with tetrahydrofuran (30 mL), 2,2-dimethylbutanoyl chloride (0.296 g, 2.20 mmol) was added to the mixture at 0° C. and the resulting mixture was stirred for 45 minutes. To the solution was added a solution which had been separately prepared by mixing H-MeAla-Phe-OH (0.601 g, 2.40 mmol), N,O-bis(trimethylsilyl)acetamide (1.03 g, 4.95 mmol) and acetonitrile (20 mL) and stirring the mixture at 25° C. for 40 minutes, and the resulting mixture was further stirred for 2 hours while maintaining to 0° C. (starting material:target compound=1: 55 (Analytical condition 1)). The obtained reaction mixture was concentrated and then diluted with ethyl acetate (20 mL), and successively washed with a saturated aqueous sodium hydrogen carbonate solution (30 mL), water (30 mL) and a saturated aqueous sodium chloride solution (15 mL) each twice. The obtained organic layer was successively washed with a 10 wt % aqueous citric acid solution (20 mL) and a saturated aqueous sodium chloride solution (20 mL). The obtained organic layer was concentrated to obtain Boc-MePhe-MeAla-Phe-OH (1.08 g, yield: 105%) as a white solid.

MASS (ESI+) m/z; (M+H)+512.3

Synthetic Example 33: Synthesis of H-MePhe-MeAla-Phe-OH·HCl

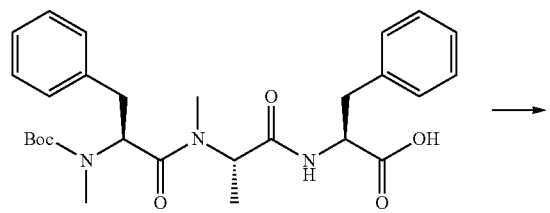

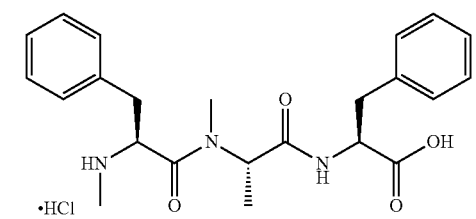

Boc-MePhe-MeAla-Phe-OH (1.06 g, 2.08 mmol) was mixed with 4M-HCl/ethyl acetate (20 mL), and the resulting mixture was stirred at 25° C. for 60 minutes. The obtained reaction mixture was concentrated, diisopropyl ether (20 mL) was added to the concentrate to suspend the same, and the generated solid was collected by Kiriyama funnel. The solid was washed with diisopropyl ether (10 mL) and dried to obtain H-MePhe-MeAla-Phe-OH·HCl (0.886 g, yield: 95%) as a white solid.

MASS (ESI+) m/z; (M+H)+411.5

Synthetic Example 34: Synthesis of Fmoc-Trp(Boc)-MePhe-MeAla-Phe-OH

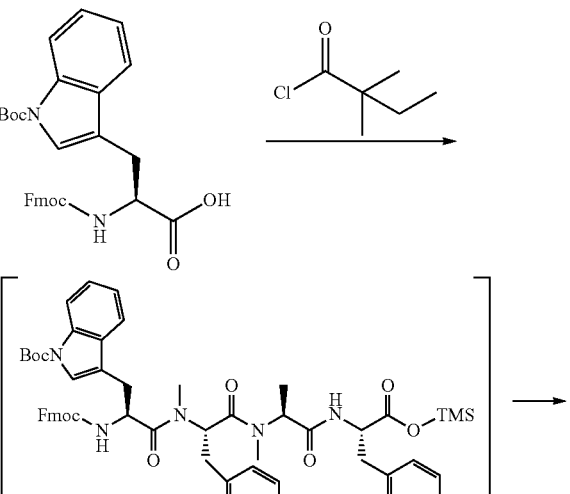

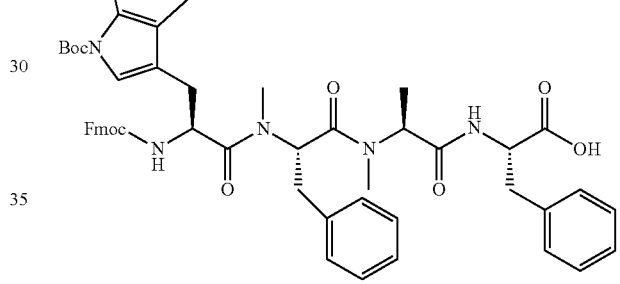

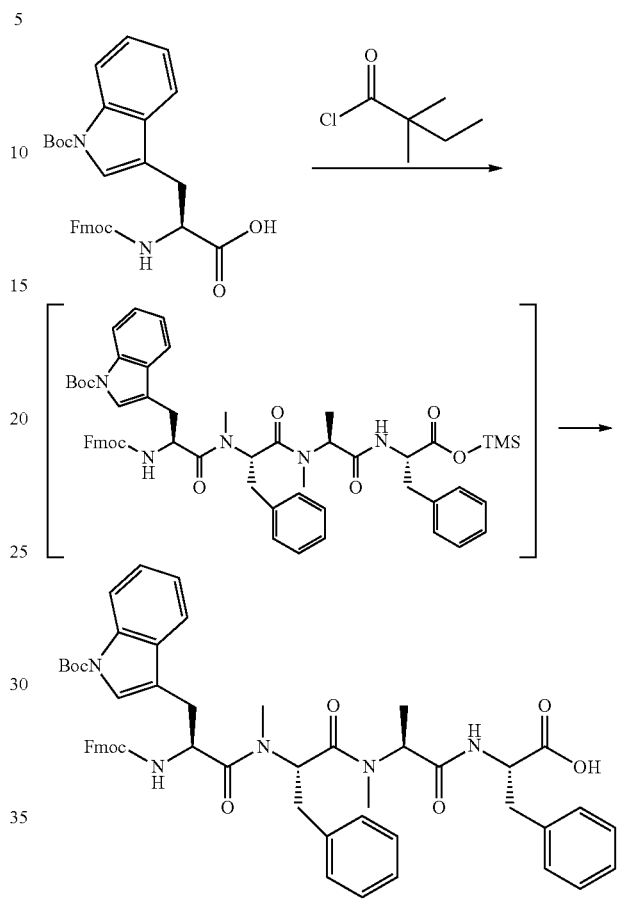

Fmoc-Trp(Boc)-OH (0.439 g, 0.833 mmol) and triethylamine (0.101 g, 1.00 mmol) were mixed with tetrahydrofuran (30 mL), 2,2-dimethylbutanoyl chloride (0.123 g, 0.917 mmol) was added to the mixture at 0° C. and the resulting mixture was stirred for 45 minutes. To the solution was added a solution which had been separately prepared by mixing H-MePhe-MeAla-Phe-OH·HCl (0.448 g, 1.00 mmol), N,O-bis(trimethylsilyl)acetamide (0.428 g, 2.06 mmol), N,N-diisopropylethylamine (1.08 g, 8.33 mmol) and acetonitrile (20 mL) and stirring the mixture at 25° C. for 40 minutes, and the resulting mixture was further stirred for 3 hours while maintaining to 25° C. (starting material:target compound=1:12 (Analytical condition 1)). The obtained reaction mixture was concentrated and then diluted with ethyl acetate (20 mL), and successively washed with a saturated aqueous sodium hydrogen carbonate solution (30 mL), water (30 mL) and a saturated aqueous sodium chloride solution (12 mL) each twice. The obtained organic layer was successively washed with a 10 wt % aqueous citric acid solution (20 mL) and a saturated aqueous sodium chloride solution (20 mL). The obtained organic layer was concentrated and the residue was dissolved in ethyl acetate (5.0 mL) and poured into hexane (95 mL). The precipitated solid was collected by filtration to obtain Fmoc-Trp(Boc)-MePhe-MeAla-Phe-OH (0.657 g, yield: 86%) as a white solid.

MASS (ESI+) m/z; (M+H)+920.5

Synthetic Example 35: Synthesis of
Fmoc-Gln(Trt)-MePhe-MeAla-Tyr-OH

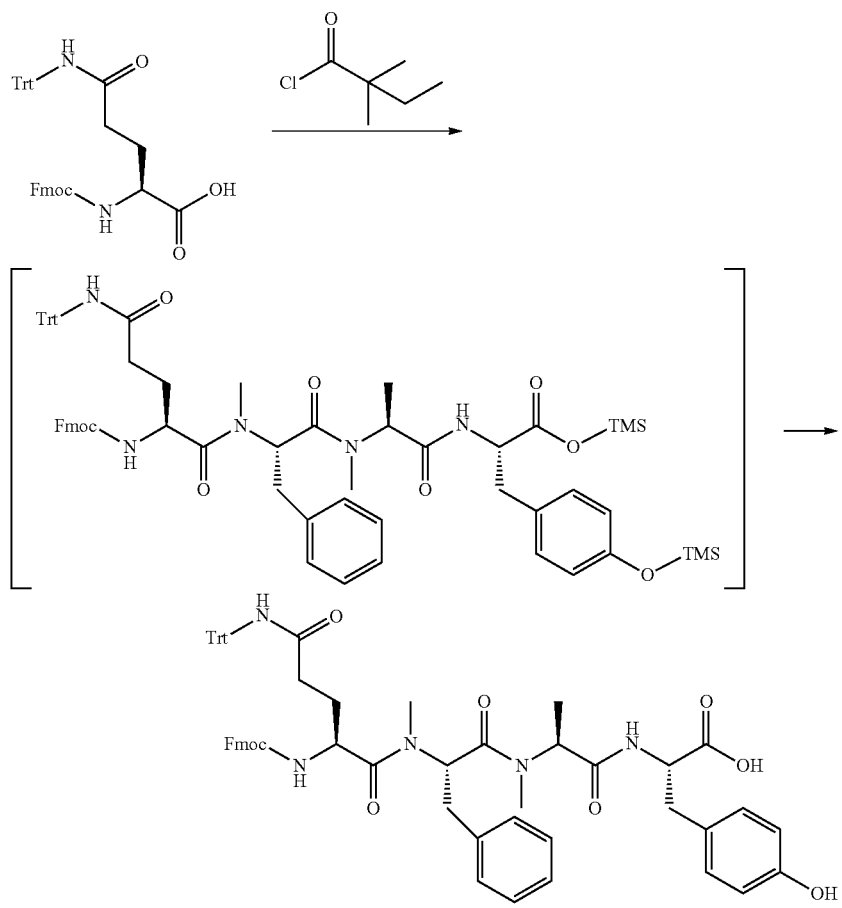

Solution A

Fmoc-Gln(Trt)-OH (0.204 g, 0.333 mmol) and triethylamine (0.040 g, 0.40 mmol) were mixed with tetrahydrofuran (20 mL), 2,2-dimethylbutanoyl chloride (0.049 g, 0.37 mmol) was added to the mixture at 0° C. and the resulting mixture was stirred for 45 minutes.

Solution B

H-MePhe-MeAla-Tyr-OH (0.171 g, 0.400 mmol), N,N-diisopropylethylamine (0.431 g, 3.33 mmol) and acetonitrile (20 mL) were mixed, and the solution was concentrated to remove the solvent. The obtained residue was mixed with acetonitrile (10 mL) and N,O-bis(trimethylsilyl)acetamide (0.343 g, 1.65 mmol), and the resulting mixture was stirred at 25° C. for 40 minutes to obtain a colorless transparent solution.

Condensation Step

While maintaining Solution A to 0° C., Solution B was mixed therewith, and the resulting mixture was further stirred for 23 hours while maintaining to 25° C. (starting material:target compound=1:5 (Analytical condition 1)). The obtained reaction mixture was concentrated and then diluted with ethyl acetate (20 mL), and successively washed with a saturated aqueous sodium hydrogen carbonate solution (15 mL), water (15 mL) and a saturated aqueous sodium chloride solution (7.5 mL) each twice. The obtained organic layer was successively washed with a 10 wt % aqueous citric acid solution (20 mL) and a saturated aqueous sodium chloride solution (20 mL). The obtained organic layer was concentrated to obtain Fmoc-Gln(Trt)-MePhe-MeAla-Tyr-OH (0.209 g, yield: 62%) as a white solid.

MASS (ESI+) m/z; (M+H)+1020.6

Synthetic Example 36: Synthesis of
Fmoc-BnGly-Phe-OH

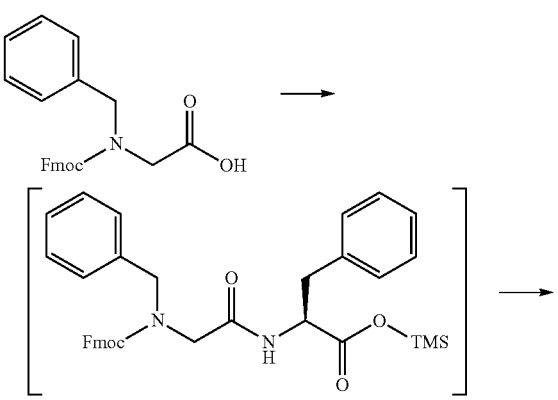

-continued

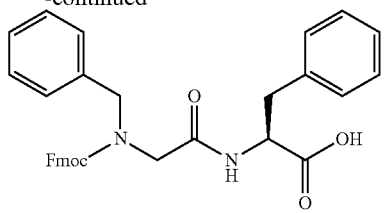

Fmoc-BnGly-OH (0.387 g, 1.00 mmol) and N-methylmorpholine (0.111 g, 1.10 mmol) were mixed with tetrahydrofuran (20 mL), isopropyl chloroformate (0.129 g, 1.05 mmol) was added to the mixture at 0° C. and the resulting mixture was stirred for 5 minutes. To the solution was added a solution which had been separately prepared by mixing H-Phe-OH (0.198 g, 1.20 mmol), N,O-bis(trimethylsilyl)acetamide (0.519 g, 2.48 mmol) and acetonitrile (5 mL) and stirring the mixture at 75° C. for 60 minutes under microwave irradiation, the mixture was stirred for 15 minutes while maintaining to 0° C., and the resulting mixture was further stirred at 25° C. for 20 hours (starting material:target compound=1:55 (Analytical condition 1)). The obtained reaction mixture was concentrated and then diluted with ethyl acetate (80 mL), and successively washed with a 10 wt % aqueous citric acid solution (50 mL), a 10 wt % aqueous sodium chloride solution (50 mL) and a saturated aqueous sodium chloride solution (50 mL). The obtained organic layer was concentrated and the concentrate was purified by silica gel column chromatography to obtain Fmoc-BnGly-Phe-OH (0.570 g, yield: 107%) as a white solid.

MASS (ESI+) m/z; (M+H)+535.3

Synthetic Example 37: Synthesis of H-BnGly-Phe-OH

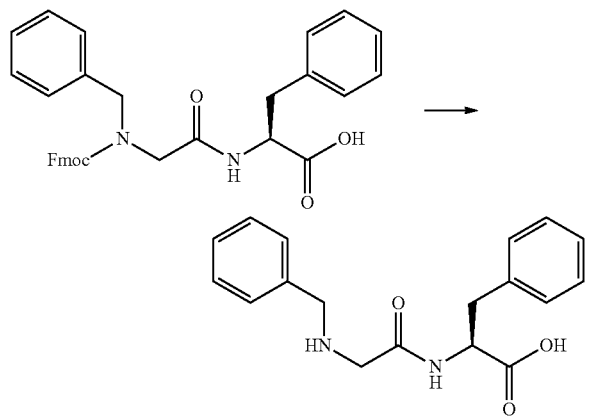

Fmoc-BnGly-Phe-OH (0.535 g, 1.00 mmol) and triethylamine (2.02 g, 20.0 mmol) were mixed with acetonitrile (20 mL), and the resulting mixture was stirred at 60° C. for 60 minutes. The obtained reaction mixture was concentrated, diisopropyl ether (50 mL) was added to the concentrate to suspend the same, and the generated solid was collected by Kiriyama funnel. The solid was washed with diisopropyl ether and dried to obtain H-BnGly-Phe-OH (0.293 g, yield: 94%) as a white solid.

MASS (ESI+) m/z; (M+H)+313.2

Synthetic Example 38: Synthesis of Boc-Phe-BnGly-Phe-OH

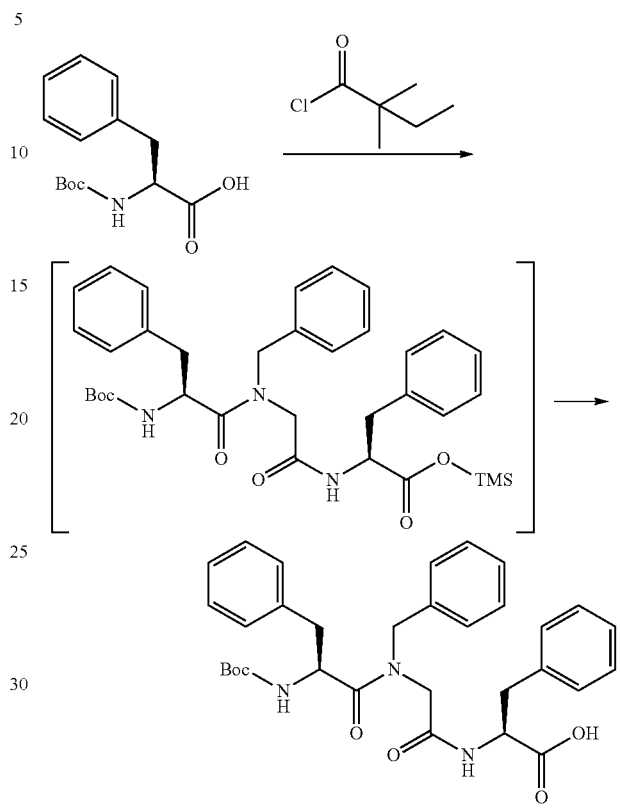

Boc-Phe-OH (0.066 g, 0.25 mmol) and triethylamine (0.030 g, 0.30 mmol) were mixed with tetrahydrofuran (5 mL), 2,2-dimethylbutanoyl chloride (0.037 g, 0.28 mmol) was added to the mixture at 0° C. and the resulting mixture was stirred for 45 minutes. To the solution was added a solution which had been separately prepared by mixing H-BnGly-Phe-OH (0.093 g, 0.30 mmol), N,O-bis(trimethylsilyl)acetamide (0.129 g, 0.616 mmol) and acetonitrile (4 mL) and stirring the mixture at 25° C. for 20 minutes, and the resulting mixture was further stirred for 14 hours while maintaining to 25° C. (starting material:target compound=1:93 (Analytical condition 3)). The obtained reaction mixture was concentrated and then diluted with ethyl acetate (40 mL), and successively washed with a saturated aqueous sodium hydrogen carbonate solution (20 mL), water (20 mL) and a saturated aqueous sodium chloride solution (10 mL). The obtained organic layer was successively washed with a 10 wt % aqueous citric acid solution and a saturated aqueous sodium chloride solution (20 mL). The obtained organic layer was concentrated and the concentrate was purified by silica gel column chromatography to obtain Boc-Phe-BnGly-Phe-OH (0.139 g, yield: 100%) as a white solid.

MASS (ESI+) m/z; (M+H)+560.4

Synthetic Example 39: Synthesis of Fmoc-n-PrGly-Phe-OH

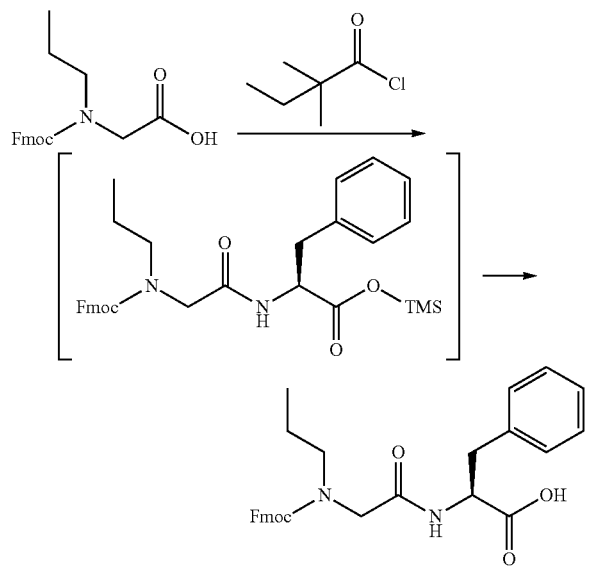

Fmoc-n-PrGly-OH (0.339 g, 1.00 mmol) and triethylamine (0.121 g, 1.20 mmol) were mixed with tetrahydrofuran (15 mL), 2,2-dimethylbutanoyl chloride (0.148 g, 1.10 mmol) was added to the mixture at 0° C. and the resulting mixture was stirred for 45 minutes. To the solution was added a solution which had been separately prepared by mixing H-Phe-OH (0.198 g, 1.20 mmol), N,O-bis(trimethylsilyl)acetamide (0.519 g, 2.48 mmol) and acetonitrile (4.5 mL) and stirring the mixture at 75° C. for 60 minutes under microwave irradiation, and the resulting mixture was further stirred for 1 hour while maintaining to 0° C. (starting material:target compound=1:32 (Analytical condition 1)). The obtained reaction mixture was concentrated and then diluted with ethyl acetate (20 mL), and successively washed with a saturated aqueous sodium hydrogen carbonate solution (20 mL), water (20 mL) and a saturated aqueous sodium chloride solution (10 mL). The obtained organic layer was successively washed with a 10 wt % aqueous citric acid solution (20 mL) and a saturated aqueous sodium chloride solution (20 mL) each twice. The obtained organic layer was concentrated and the concentrate was purified by silica gel column chromatography to obtain Fmoc-n-PrGly-Phe-OH (0.538 g, yield: 111%) as a white solid.

MASS (ESI+) m/z; (M+H)+487.3

Synthetic Example 40: Synthesis of H-n-PrGly-Phe-OH

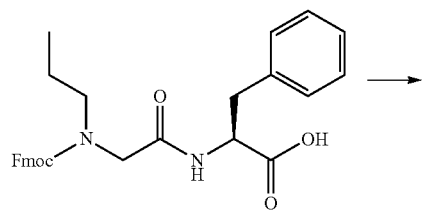

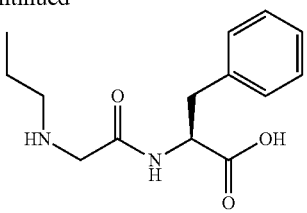

Fmoc-n-PrGly-Phe-OH (0.487 g, 1.00 mmol) and triethylamine (2.02 g, 20.0 mmol) were mixed with acetonitrile (20 mL), and the resulting mixture was stirred at 60° C. for 60 minutes. The obtained reaction mixture was concentrated, diisopropyl ether (50 mL) was added to the concentrate to suspend the same, and the generated solid was collected by Kiriyama funnel. The solid was washed with diisopropyl ether and dried to obtain H-n-PrGly-Phe-OH (0.245 g, yield: 93%) as a white solid.

MASS (ESI+) m/z; (M+H)+265.2

Synthetic Example 41: Synthesis of Boc-Phe-n-PrGly-Phe-OH

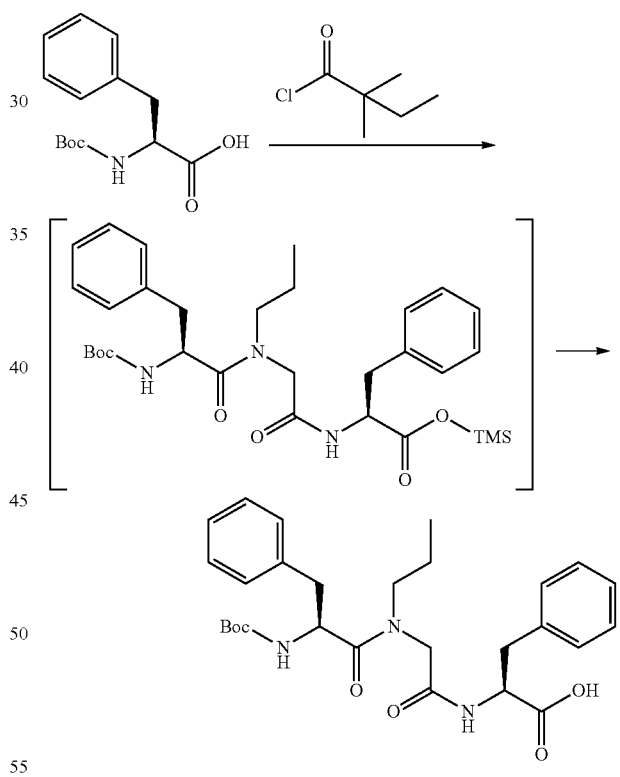

Boc-Phe-OH (0.066 g, 0.25 mmol) and triethylamine (0.030 g, 0.300 mmol) were mixed with tetrahydrofuran (5.0 mL), 2,2-dimethylbutanoyl chloride (0.037 g, 0.27 mmol) was added to the mixture at 0° C. and the resulting mixture was stirred for 45 minutes. To the solution was added a solution which had been separately prepared by mixing H-n-PrGly-Phe-OH (0.066 g, 0.25 mmol), N,O-bis(trimethylsilyl)acetamide (0.118 g, 0.564 mmol) and acetonitrile (4.0 mL) and stirring the mixture at 25° C. for 30 minutes, and the resulting mixture was further stirred for 1 hour or longer while maintaining to 25° C. (starting material:target compound=1:85 (Analytical condition 3)). The obtained reaction mixture was concentrated and then diluted with ethyl acetate (40 mL), and successively washed with a saturated aqueous sodium hydrogen carbonate solution (20 mL), water (20 mL) and a saturated aqueous sodium chloride solution (10 mL). The obtained organic layer was successively washed with a 10 wt % aqueous citric acid solution and a saturated aqueous sodium chloride solution. The obtained organic layer was concentrated and the concentrate was purified by silica gel column chromatography to obtain Boc-Phe-n-PrGly-Phe-OH (0.125 g, yield: 98%) as a white solid.

MASS (ESI+) m/z; (M+H)+512.4

Synthetic Example 42: Synthesis of Fmoc-MePhe-n-PrGly-Phe-OH

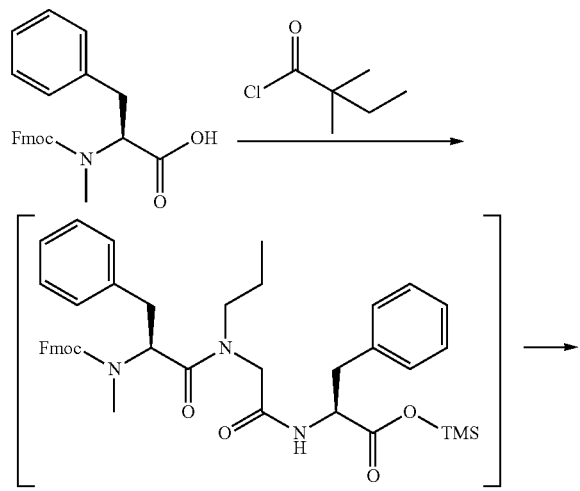

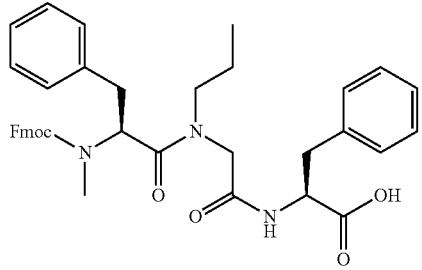

Fmoc-MePhe-OH (0.080 g, 0.20 mmol) and triethylamine (0.024 g, 0.24 mmol) were mixed with tetrahydrofuran (5 mL), 2,2-dimethylbutanoyl chloride (0.030 g, 0.22 mmol) was added to the mixture at 0° C. and the resulting mixture was stirred for 45 minutes. To the solution was added a solution which had been separately prepared by mixing H-n-PrGly-Phe-OH (0.063 g, 0.24 mmol), N,O-bis(trimethylsilyl)acetamide (0.104 g, 0.50 mmol) and acetonitrile (2 mL) and stirring the mixture at 0° C. for 30 minutes, and the resulting mixture was further stirred for 2 hours while maintaining to 25° C. (starting material:target compound=1: 18 (Analytical condition 1)). The obtained reaction mixture was concentrated and then diluted with ethyl acetate (40 mL), and successively washed with a 10 wt % aqueous citric acid solution (30 mL), 5 wt % aqueous sodium chloride solution (30 mL) and a saturated aqueous sodium chloride solution (30 mL). The obtained organic layer was concentrated to obtain Fmoc-MePhe-n-PrGly-Phe-OH (0.153 g, yield: 118%) as a white solid.

MASS (ESI+) m/z; (M+H)+648.4

Synthetic Example 43: Synthesis of Boc-MePhe-MePhe-MeAla-Tyr-OH

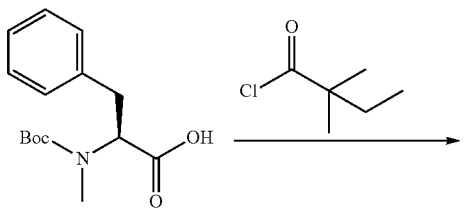

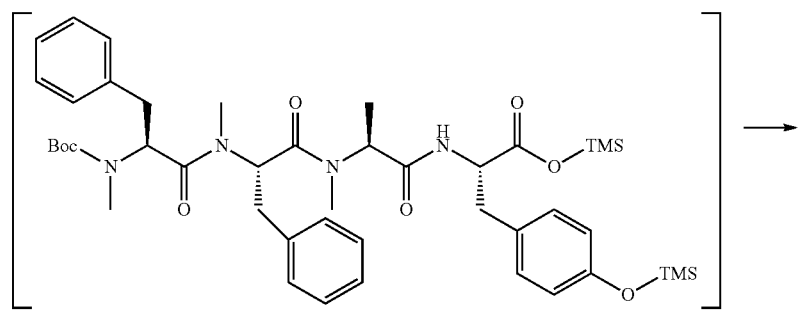

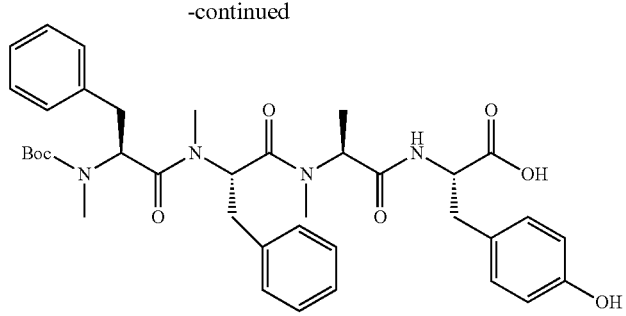

Boc-MePhe-OH (0.084 g, 0.30 mmol) and triethylamine (0.036 g, 0.36 mmol) were mixed with tetrahydrofuran (6.0 mL), 2,2-dimethylbutanoyl chloride (0.044 g, 0.331 mmol) was added to the mixture at 0° C. and the resulting mixture was stirred for 1 hour. To the solution was added a solution which had been separately prepared by mixing H-MePhe-MeAla-Tyr-OH (0.141 g, 0.305 mmol), N,O-bis(trimethylsilyl)acetamide (0.215 g, 1.023 mmol), N,N-diisopropylethylamine (0.086 g, 0.662 mmol) and acetonitrile (5.0 mL) and stirring the mixture at 0° C. for 60 minutes, and the resulting mixture was further stirred at 25° C. for 16 hours (starting material:target compound=1:59 (Analytical condition 3)). The obtained reaction mixture was concentrated and then diluted with ethyl acetate (40 mL), and successively washed with a saturated aqueous sodium hydrogen carbonate solution (20 mL), water (20 mL) and a saturated aqueous sodium chloride solution (10 mL). The obtained organic layer was successively washed with a 10 wt % aqueous citric acid solution and a saturated aqueous sodium chloride solution. The obtained organic layer was concentrated and the concentrate was purified by silica gel column chromatography to obtain Boc-MePhe-MePhe-MeAla-Tyr-OH (0.177 g, yield: 85%) as a white solid.

MASS (ESI+) m/z; (M+H)+689.5

Synthetic Example 44: Synthesis of Fmoc-Glu(tBu)-MePhe-MePhe-MeAla-Tyr-OH

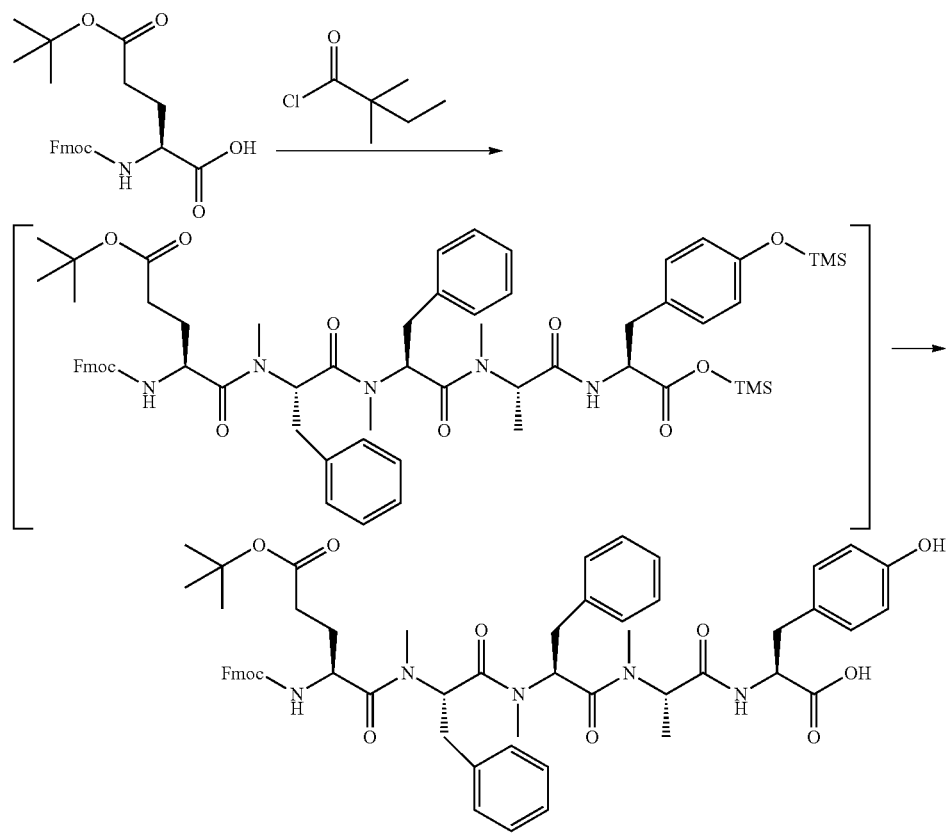

Solution A

Fmoc-Glu(tBu)-OH (0.091 g, 0.21 mmol) and triethylamine (0.026 g, 0.257 mmol) were mixed with tetrahydrofuran (5.0 mL), 2,2-dimethylbutanoyl chloride (0.032 g, 0.24 mmol) was added to the mixture at 0° C. and the resulting mixture was stirred for 1 hour.

Solution B

Boc-MePhe-MePhe-MeAla-Tyr-OH (0.177 g, 0.257 mmol) and trifluoroacetic acid (3.0 mL) were mixed, and the resulting mixture was further stirred for 30 minutes while maintaining to 25° C. The solution was concentrated to remove trifluoroacetic acid, and acetonitrile (20 mL) was mixed and the mixture was concentrated. To the obtained residue were added acetonitrile (8.0 mL) and triethylamine (0.026 g, 0.257 mmol), and the solution was concentrated to remove the solvent and triethylamine. The obtained residue was mixed with acetonitrile (5.0 mL) and N,O-bis(trimethylsilyl)-acetamide (0.167 g, 0.80 mmol), and the resulting mixture was stirred at 25° C. for 5 minutes to obtain a colorless transparent solution.

Condensation Step

While maintaining Solution A to 0° C., Solution B was mixed therewith, and the resulting mixture was further stirred for 17 hours while maintaining to 25° C. (starting material:target compound=1:5 (Analytical condition 3)). The obtained reaction mixture was concentrated and then diluted with ethyl acetate (30 mL), and successively washed with a saturated aqueous sodium hydrogen carbonate solution (20 mL), water (20 mL) and a saturated aqueous sodium chloride solution (10 mL). The obtained organic layer was concentrated to obtain Fmoc-Glu(tBu)-MePhe-MePhe-MeAla-Tyr-OH (0.192 g, yield: 90%) as a white solid.

MASS (ESI+) m/z; (M+H)+730.4, +996.5

Synthetic Example 45: Synthesis of Fmoc-Cys(Trt)-MePhe-OH

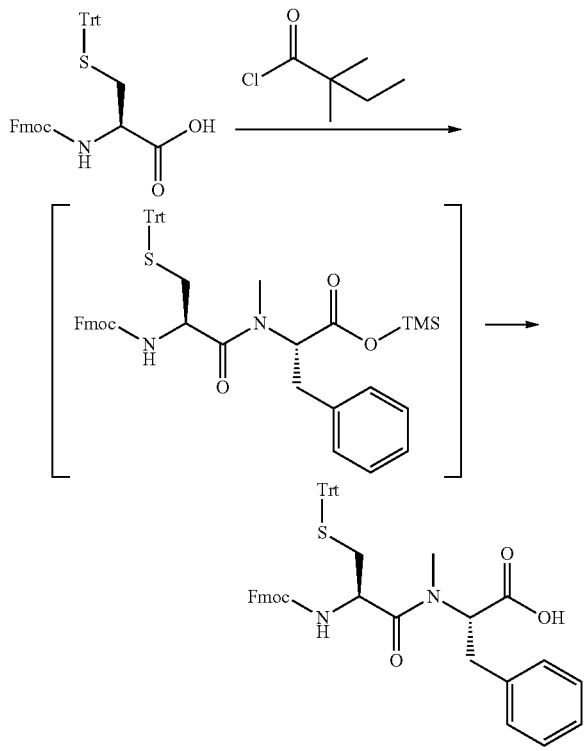

Fmoc-Cys(Trt)-OH (0.147 g, 0.251 mmol) and triethylamine (0.031 g, 0.30 mmol) were mixed with tetrahydrofuran (5.0 mL), 2,2-dimethylbutanoyl chloride (0.037 g, 0.28 mmol) was added to the mixture at 0° C. and the resulting mixture was stirred for 1 hour. To the solution was added a solution which had been separately prepared by mixing H-MePhe-OH (0.054 g, 0.30 mmol), N,O-bis(trimethylsilyl)acetamide (0.130 g, 0.62 mmol) and acetonitrile (4.0 mL) and stirring the mixture at 75° C. for 20 minutes, and the resulting mixture was further stirred for 1 hour while maintaining to 0° C. (starting material:target compound=1:28 (Analytical condition 3)). The obtained reaction mixture was concentrated and then diluted with ethyl acetate (40 mL), and successively washed with a 10 wt % aqueous citric acid solution, a saturated aqueous sodium hydrogen carbonate solution, water and a saturated aqueous sodium chloride solution. The obtained organic layer was concentrated and the concentrate was purified by silica gel column chromatography to obtain Fmoc-Cys(Trt)-MePhe-OH (0.187 g, yield: 100%) as a white solid.

MASS (ESI+) m/z; (M+H)+243.2 (trityl cation), +747.2

Synthetic Example 46: Synthesis of Boc-Arg(Cbz)$_2$-MePhe-OH

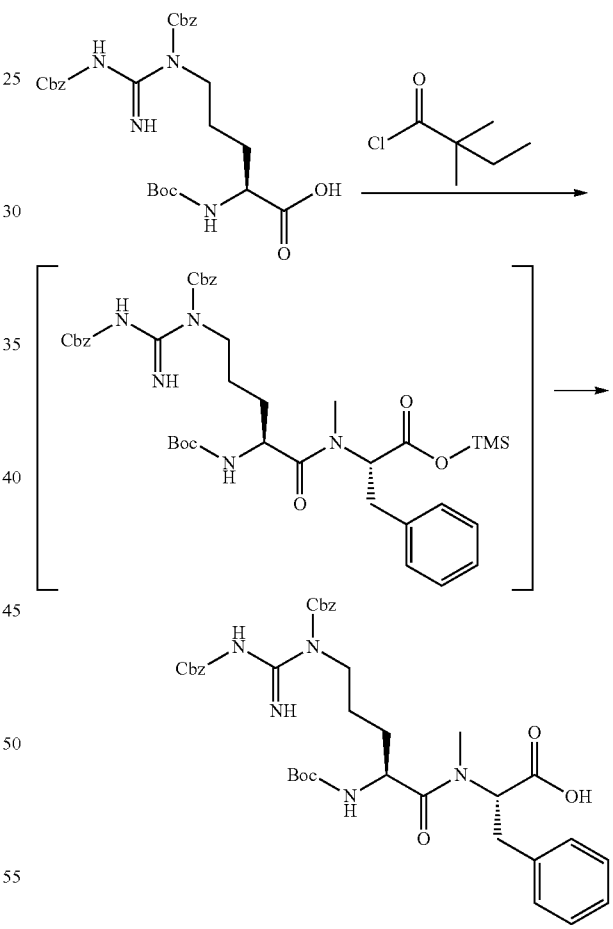

Boc-Arg(Cbz)$_2$-OH (0.136 g, 0.250 mmol) and triethylamine (0.030 g, 0.30 mmol) were mixed with tetrahydrofuran (5.0 mL), 2,2-dimethylbutanoyl chloride (0.037 g, 0.28 mmol) was added to the mixture at 0° C. and the resulting mixture was stirred for 45 minutes. To the solution was added a solution which had been separately prepared by mixing H-MePhe-OH (0.054 g, 0.30 mmol), N,O-bis(trimethylsilyl)acetamide (0.128 g, 0.62 mmol) and acetonitrile (4.0 mL) and stirring the mixture at 75° C. for 10 minutes, and the resulting mixture was further stirred for 1 hour or longer while maintaining to 25° C. (starting material:target compound=1:25 (Analytical condition 2)). The obtained reaction mixture was concentrated and then diluted with ethyl acetate (40 mL), and successively washed with a saturated aqueous sodium hydrogen carbonate solution (20 mL), water (20 mL) and a saturated aqueous sodium chloride solution (10 mL). The obtained organic layer was successively washed with a 10 wt % aqueous citric acid solution and a saturated aqueous sodium chloride solution. The obtained organic layer was concentrated and the concentrate was purified by silica gel column chromatography to obtain Boc-Arg (Cbz)$_2$-MePhe-OH (0.175 g, yield: 99%) as a white solid. MASS (ESI+) m/z; (M+H)+704.5

Synthetic Example 47: Synthesis of Boc-Arg (Cbz)$_2$-MeAla-Phe-OH

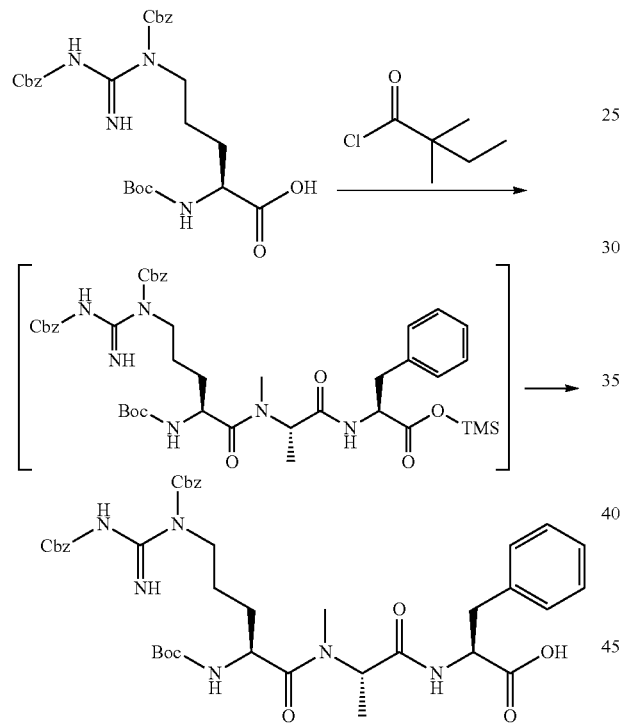

Boc-Arg (Cbz)$_2$-OH (0.136 g, 0.251 mmol) and triethylamine (0.030 g, 0.30 mmol) were mixed with tetrahydrofuran (5.0 mL), 2,2-dimethylbutanoyl chloride (0.037 g, 0.28 mmol) was added to the mixture at 0° C. and the resulting mixture was stirred for 1 hour. To the solution was added a solution which had been separately prepared by mixing H-MeAla-Phe-OH (0.075 g, 0.30 mmol), N,O-bis(trimethylsilyl)acetamide (0.130 g, 0.621 mmol) and acetonitrile (4.0 mL) and stirring the mixture at 25° C. for 20 minutes, and the resulting mixture was further stirred for 14 hours while maintaining to 25° C. (starting material:target compound=1:13 (Analytical condition 2)). The obtained reaction mixture was concentrated and then diluted with ethyl acetate (40 mL), and successively washed with a saturated aqueous sodium hydrogen carbonate solution (20 mL), water (20 mL) and a saturated aqueous sodium chloride solution (10 mL). The obtained organic layer was successively washed with a 10 wt % aqueous citric acid solution and a saturated aqueous sodium chloride solution. The obtained organic layer was concentrated and the concentrate was purified by silica gel column chromatography to obtain Boc-Arg (Cbz)$_2$-MeAla-Phe-OH (0.192 g, yield: 99%) as a white solid. MASS (ESI+) m/z; (M+H)+775.5

Synthetic Example 48: Synthesis of Fmoc-His(Boc)-MePhe-OH

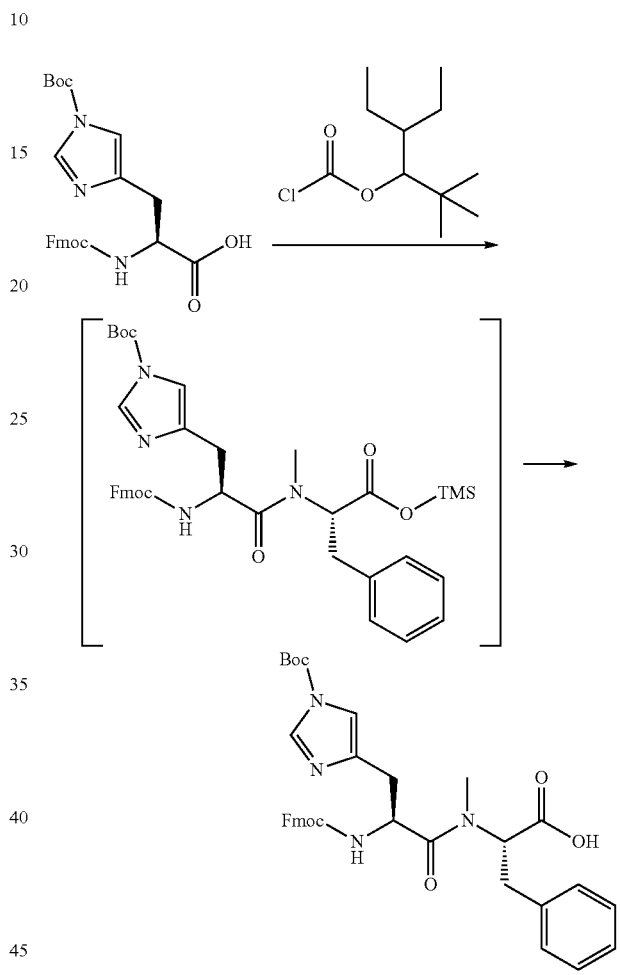

Fmoc-His(Boc)-OH (0.120 g, 0.251 mmol) and N-methylmorpholine (0.033 g, 0.33 mmol) were mixed with tetrahydrofuran (5.0 mL), 4-ethyl-2,2-dimethylhexan-3-yl carbonochloridate (0.067 g, 0.30 mmol) was added to the mixture at 0° C. and the resulting mixture was stirred for 2 hours. To the solution was added a solution which had been separately prepared by mixing H-MePhe-OH (0.058 g, 0.33 mmol), N,O-bis(trimethylsilyl)acetamide (0.141 g, 0.679 mmol) and acetonitrile (4 mL) and stirring the mixture at 75° C. for 20 minutes, and the resulting mixture was further stirred at 25° C. for 13 hours (starting material:target compound=1:6 (Analytical condition 2)). The obtained reaction mixture was diluted with ethyl acetate (40 mL), and successively washed with a 10 wt % aqueous citric acid solution and a saturated aqueous sodium chloride solution. The obtained organic layer was concentrated and the concentrate was purified by silica gel column chromatography to obtain Fmoc-His(Boc)-MePhe-OH (0.131 g, yield: 82%) as a white solid.

MASS (ESI+) m/z; (M+H)+539.6, +639.4

Synthetic Example 49: Synthesis of Fmoc-MeHis(Trt)-Leu-OH

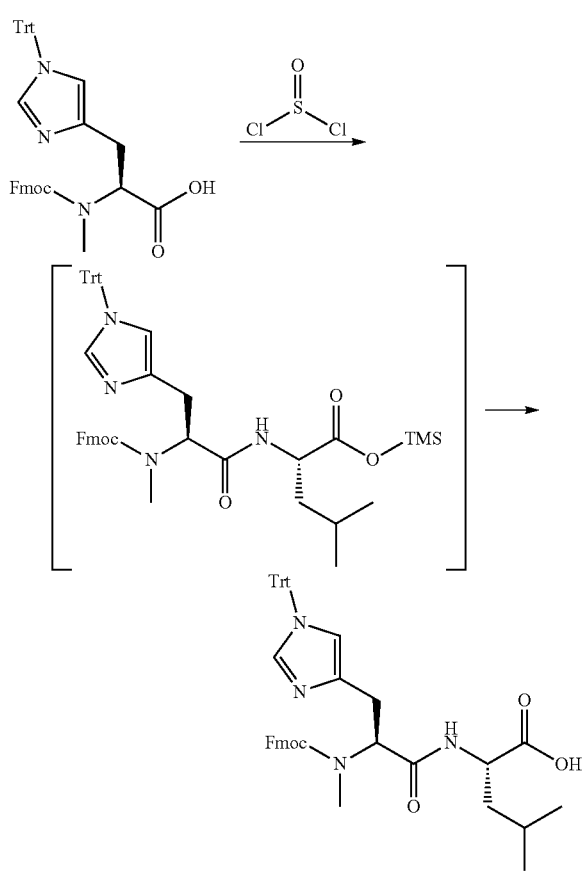

Solution A

Fmoc-MeHis(Trt)-OH (1.27 g, 2.00 mmol) and N,N-dimethylformamide (0.015 g, 0.20 mmol) were mixed with tetrahydrofuran (30 mL), thionyl chloride (1.19 g, 10.0 mmol) was added to the mixture at 0° C. and the resulting mixture was stirred at 25° C. for 1 hour. The solution was concentrated to remove thionyl chloride and the solvent, and tetrahydrofuran (10 mL) was mixed and the mixture was concentrated. To the obtained residue were added tetrahydrofuran (10 mL) to obtain a pale yellowish transparent acid chloride solution.

Solution B

Leu-OH (0.315 g, 2.40 mmol), N,O-bis(trimethylsilyl)acetamide (1.30 g, 6.26 mmol) and acetonitrile (5 mL) were mixed, and the resulting mixture was stirred at 80° C. for 1 hour to obtain a colorless transparent solution.

Condensation Step

While maintaining Solution A to 0° C., Solution B was mixed therewith, and the resulting mixture was further stirred for 1 hour while maintaining to 0° C. (starting material:target compound=1:25 (Analytical condition 3)). The obtained reaction mixture was concentrated and then diluted with ethyl acetate (40 mL), and successively washed with a 10 wt % aqueous citric acid solution and a saturated aqueous sodium chloride solution. The obtained organic layer was concentrated and the concentrate was purified by silica gel column chromatography to obtain Fmoc-MeHis(Trt)-Leu-OH (1.37 g, yield: 92%) as a pale yellowish solid.

MASS (ESI+) m/z; (M+H)+747.4

Synthetic Example 50: Synthesis of H-MeHis(Trt)-Leu-OH

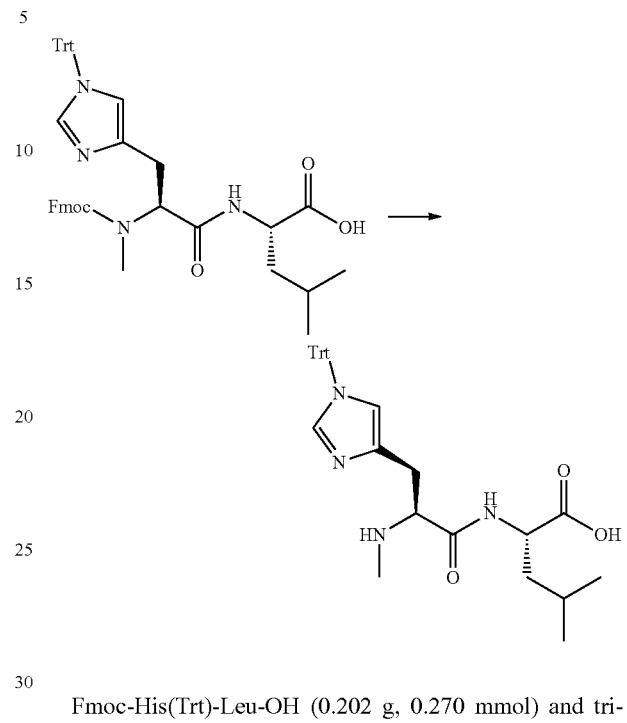

Fmoc-His(Trt)-Leu-OH (0.202 g, 0.270 mmol) and triethylamine (0.564 g, 5.40 mmol) were mixed with acetonitrile (4.0 mL) and tetrahydrofuran (4.0 mL), and the resulting mixture was stirred at 80° C. for 60 minutes. The obtained reaction mixture was concentrated, tetrahydrofuran (3.0 mL) and diisopropyl ether (9.0 mL) were added to the concentrate to suspend the same, and the generated solid was collected by Kiriyama funnel. The solid was washed with diisopropyl ether (10 mL) and dried to obtain H-MeHis(Trt)-Leu-OH (0.130 g, yield: 92%) as a white solid. MASS (ESI+) m/z; (M+H)+525.8

Synthetic Example 51: Synthesis of Fmoc-Phe-MeHis(Trt)-Leu-OH

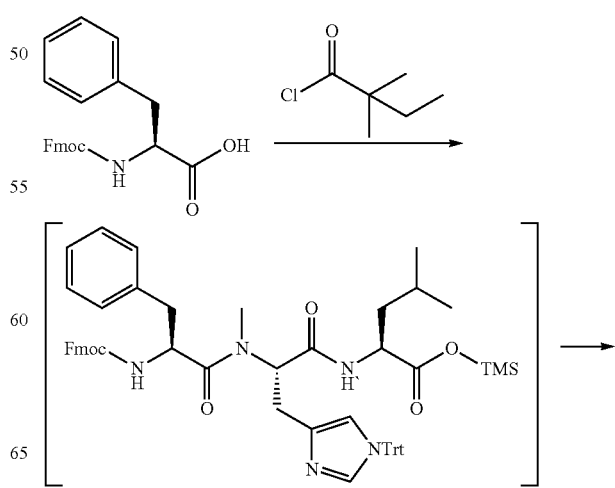

-continued

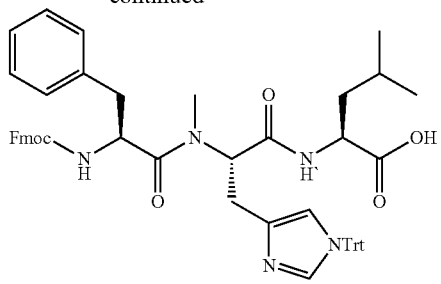

Fmoc-Phe-OH (0.078 g, 0.20 mmol) and triethylamine (0.024 g, 0.24 mmol) were mixed with tetrahydrofuran (5.0 mL), 2,2-dimethylbutanoyl chloride (0.030 g, 0.22 mmol) was added to the mixture at 0° C. and the resulting mixture was stirred for 1 hour. To the solution was added a solution which had been separately prepared by mixing H-MeHis(Trt)-Leu-OH (0.116 g, 0.221 mmol), N,O-bis(trimethylsilyl)-acetamide (0.096 g, 0.46 mmol) and acetonitrile (4.0 mL) and stirring the mixture at 25° C. for 30 minutes, and the resulting mixture was further stirred for 5 hours while maintaining to 25° C. (starting material:target compound=1:5 (Analytical condition 2)). The obtained reaction mixture was concentrated and then diluted with ethyl acetate (40 mL), and successively washed with a 10 wt % aqueous citric acid solution, a saturated aqueous sodium hydrogen carbonate solution, water and a saturated aqueous sodium chloride solution. The obtained organic layer was concentrated to obtain Fmoc-Phe-MeHis(Trt)-Leu-OH (0.154 g, yield: 86%) as a white solid.

MASS (ESI+) m/z; (M+H)+894.5

Synthetic Example 52: Synthesis of Fmoc-Val-MePhe-OH

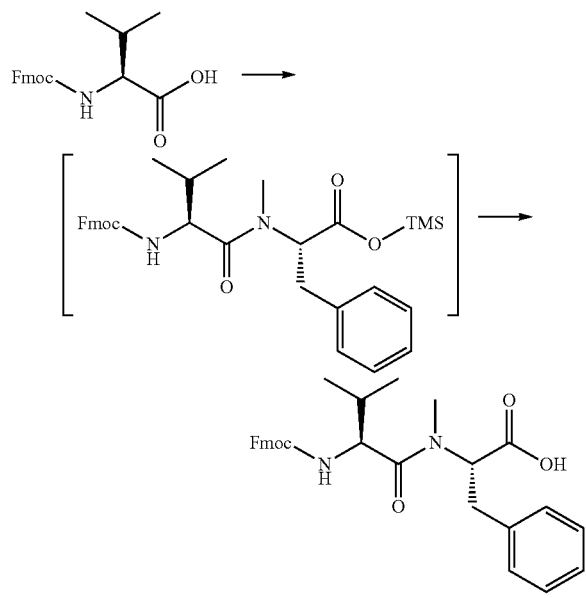

Fmoc-Val-OH (0.101 g, 0.298 mmol) and triethylamine (0.053 mL, 0.383 mmol) were mixed with tetrahydrofuran (1.0 g), pivaloyl chloride (0.043 mL, 0.354 mmol) was added to the mixture at 0° C. and the resulting mixture was stirred for 1 hour. To the solution was added a solution which had been separately prepared by mixing H-MePhe-OH (0.080 g, 0.446 mmol), trimethylsilyl chloride (0.070 mL, 0.554 mmol), triethylamine (0.082 mL, 0.592 mmol) and acetonitrile (0.80 g) and stirring the mixture at 50° C. for 1.5 hours, and the resulting mixture was further stirred for 70 hours while maintaining to 0° C. (starting material:target compound=3.5:1). The obtained reaction mixture was diluted with ethyl acetate (5.0 g), and successively washed with a 10 wt % aqueous citric acid solution (3.0 g) and a saturated brine solution (2.0 g) twice. As a result of HPLC analysis using the obtained organic layer, the quantitative yield was 11%.

In the following, otherwise specifically mentioned, a ratio of the starting material Fmoc-Val-OH and the product Fmoc-Val-MePhe-OH was calculated by the analysis <Analytical condition 4> using high performance liquid chromatography.

<Analytical Condition 4>
High performance liquid chromatography: HPLC LC-20A manufactured by Shimadzu Corporation
Column: Poroshell 120EC-C18 (2.7 μm, 3.0×100 mm) manufactured by Agilent
Column oven temperature: 40° C.
Eluent: acetonitrile:0.05 vol % phosphoric acid aqueous solution
50:50 (0-15 min), 50:50-95:5 (15-18 min), 95:5 (18-22 min) (v/v)
Eluent speed: 0.7 mL/min
Detection wavelength: 210 nm In the following, otherwise specifically mentioned, the quantitative yield of Fmoc-Val-MePhe-OH was calculated by the quantitative analysis method by <Analytical Condition 4>.

Standard substance: Fmoc-Val-MePhe-OH obtained by the method described in Synthetic Example 57 was purified by silica gel chromatography and made the standard substance.

MASS (ESI+) m/z; (M+H)+501.22
Quantitative method; Absolute calibration method

Synthetic Example 53: Synthesis of Fmoc-Val-MePhe-OH

Fmoc-Val-OH (0.100 g, 0.295 mmol) and triethylamine (0.053 mL, 0.38 mmol) were mixed with tetrahydrofuran (1.0 g), pivaloyl chloride (0.043 mL, 0.35 mmol) was added to the mixture at 0° C. and the resulting mixture was stirred for 1 hour. To the solution was added a solution which had been separately prepared by mixing H-MePhe-OH (0.079 g, 0.44 mmol), N,O-bis(trimethylsilyl)acetamide (0.135 mL, 0.552 mmol) and acetonitrile (0.81 g) and stirring the mixture at 50° C. for 1.5 hours, and the resulting mixture was further stirred for 70 hours while maintaining to 0° C. (starting material:target compound=1:7). The obtained reaction mixture was diluted with ethyl acetate (5.0 g), and washed with a 10 wt % aqueous citric acid solution (2.0 g) and a saturated brine solution (1.0 g) twice. The quantitative yield of Fmoc-Val-MePhe-OH of the collected organic layer was 79%.

Synthetic Example 54: Synthesis of Fmoc-Val-MePhe-OH

Fmoc-Val-OH (0.100 g, 0.295 mmol) and N-methylmorpholine (0.042 mL, 0.383 mmol) were mixed with tetrahydrofuran (1.0 g), isobutyl carbonochloridate (0.046 mL, 0.35 mmol) was added to the mixture at 0° C. and the resulting mixture was stirred for 5 minutes. To the solution was added a solution which had been separately prepared by mixing H-MePhe-OH (0.079 g, 0.44 mmol), N,O-bis(trimethylsilyl)acetamide (0.135 mL, 0.552 mmol) and acetonitrile (0.79 g) and stirring the mixture at 50° C. for 1 hour, and the resulting mixture was further stirred for 21 hours while maintaining to 0° C. (starting material:target compound=3.5:1). The obtained reaction mixture was diluted with ethyl acetate (5.0 g), and washed with a 10 wt % aqueous citric acid solution (2.0 g) and a saturated brine solution (1.0 g) twice. The quantitative yield of Fmoc-Val-MePhe-OH of the collected organic layer was 18%.

Synthetic Example 55: Synthesis of Fmoc-Val-MePhe-OH

Fmoc-Val-OH (0.100 g, 0.295 mmol) and triethylamine (0.053 mL, 0.38 mmol) were mixed with tetrahydrofuran (1.0 g), 2-ethylbutanoyl chloride (0.048 mL, 0.35 mmol) was added to the mixture at 0° C. and the resulting mixture was stirred for 1 hour. To the solution was added a solution which had been separately prepared by mixing H-MePhe-OH (0.079 g, 0.44 mmol), N,O-bis(trimethylsilyl)acetamide (0.135 mL, 0.552 mmol) and acetonitrile (0.79 g) and stirring the mixture at 50° C. for 1 hour, and the resulting mixture was further stirred for 110 hours while maintaining to 0° C. (starting material:target compound=1:13). The obtained reaction mixture was diluted with ethyl acetate (5.0 g), and washed with a 10 wt % aqueous citric acid solution (2.0 g) and a saturated brine solution (1.0 g) twice. The quantitative yield of Fmoc-Val-MePhe-OH of the collected organic layer was 87%.

Synthetic Example 56: Synthesis of Fmoc-Val-MePhe-OH

Fmoc-Val-OH (0.100 g, 0.295 mmol) and triethylamine (0.053 mL, 0.38 mmol) were mixed with tetrahydrofuran (1.0 g), 2,2-dimethylbutanoyl chloride (0.049 mL, 0.35 mmol) was added to the mixture at 0° C. and the resulting mixture was stirred for 1 hour. To the solution was added a solution which had been separately prepared by mixing H-MePhe-OH (0.079 g, 0.44 mmol), N,O-bis(trimethylsilyl)acetamide (0.135 mL, 0.552 mmol) and acetonitrile (0.79 g) and stirring the mixture at 50° C. for 1 hour, and the resulting mixture was further stirred for 95 hours while maintaining to 0° C. (starting material:target compound=1:18). The obtained reaction mixture was diluted with ethyl acetate (5.0 g), and washed with a 10 wt % aqueous citric acid solution (2.0 g) and a saturated brine solution (1.0 g) twice. The quantitative yield of Fmoc-Val-MePhe-OH of the collected organic layer was 89%.

Synthetic Example 57: Synthesis of Fmoc-Val-MePhe-OH

Fmoc-Val-OH (0.100 g, 0.295 mmol) and N,N-diisopropylethylamine (0.058 mL, 0.32 mmol) were mixed with acetonitrile (1.0 g), a 50 wt % toluene solution of 2-(4,4-dimethylpentan-2-yl)-5,7,7-trimethyloctanoyl chloride (0.107 g, 0.354 mmol) was added to the mixture at 0° C. and the resulting mixture was stirred for 2 hours. To the solution was added a solution which had been separately prepared by mixing H-MePhe-OH (0.079 g, 0.442 mmol), N,O-bis(trimethylsilyl)acetamide (0.135 mL, 0.552 mmol) and acetonitrile (0.79 g) and stirring the mixture at 50° C. for 1 hour, and the resulting mixture was further stirred for 67 hours while maintaining to 0° C. and at 20° C. for 7 hours (starting material:target compound=1:35). The obtained reaction mixture was quenched with methanol (0.5 mL) and N,N-diisopropylethylamine (0.05 mL), then, diluted with ethyl acetate (5.0 g), and washed with a 10 wt % aqueous citric acid solution (2.0 g) and a saturated brine solution (1.0 g) twice. The quantitative yield of Fmoc-Val-MePhe-OH of the collected organic layer was 96%.

2-(4,4-Dimethylpentan-2-yl)-5,7,7-trimethyloctanoyl chloride was synthesized with reference to JP Patent No. 3,406,093C.

Synthetic Example 58: Synthesis of Fmoc-Val-MePhe-OH

Fmoc-Val-OH (0.100 g, 0.295 mmol) and N-methylmorpholine (0.071 mL, 0.648 mmol) were mixed with N,N-dimethylacetamide (5.9 mL), 2,4-dimethylpentan-3-yl carbonochloridate (0.105 g, 0.589 mmol) was added to the mixture at 0° C. and the resulting mixture was stirred for 2 hours. To the solution was added a solution which had been separately prepared by mixing H-MePhe-OH (0.106 g, 0.589 mmol), N,O-bis(trimethylsilyl)acetamide (0.288 mL, 1.179 mmol) and acetonitrile (7.9 mL) and stirring the mixture at 75° C. for 15 minutes, and the resulting mixture was further stirred for 114 hours while maintaining to 0° C. and at 20° C. for 4 hours (starting material:target compound=1:11). The obtained reaction mixture was quenched with methanol (5.0 mL) and N,N-diisopropylethylamine (0.50 mL), then, diluted with ethyl acetate (30.0 g), and washed with a 10 wt % aqueous citric acid solution (18.0 g) and a saturated brine solution (6.0 g) twice. The quantitative yield of Fmoc-Val-MePhe-OH of the collected organic layer was 85%.

Synthetic Example 59: Synthesis of Fmoc-Val-MePhe-OH

Fmoc-Val-OH (0.100 g, 0.295 mmol) and N-methylmorpholine (0.071 mL, 0.648 mmol) were mixed with N,N-dimethylacetamide (5.9 mL), 2,2,4-trityl pentan-3-yl carbonochloridate (0.114 g, 0.589 mmol) was added to the mixture at 0° C. and the resulting mixture was stirred for 2 hours. To the solution was added a solution which had been separately prepared by mixing H-MePhe-OH (0.106 g, 0.589 mmol), N,O-bis(trimethylsilyl)acetamide (0.288 mL, 1.179 mmol) and acetonitrile (7.9 mL) and stirring the mixture at 75° C. for 15 minutes, and the resulting mixture was further stirred for 91 hours while maintaining to 0° C. and at 20° C. for 7 hours (starting material:target compound=1:10). The obtained reaction mixture was quenched with methanol (5.0 mL) and N,N-diisopropylethylamine (0.50 mL), then, diluted with ethyl acetate (30.0 g), and washed with a 10 wt % aqueous citric acid solution (18.0 g) and a saturated brine solution (6.0 g) twice. The quantitative yield of Fmoc-Val-MePhe-OH of the collected organic layer was 88%.

Synthetic Example 60: Synthesis of Fmoc-Val-MePhe-OH

Fmoc-Val-OH (0.100 g, 0.295 mmol) and N,N-diisopropylethylamine (0.065 mL, 0.38 mmol) were mixed with tetrahydrofuran (1.0 g), 1-adamantanecarbonyl chloride (0.070 g, 0.35 mmol) was added to the mixture at 0° C. and the resulting mixture was stirred for 1 hour. To the solution was added a solution which had been separately prepared by mixing H-MePhe-OH (0.079 g, 0.44 mmol), N,O-bis(trimethylsilyl)-acetamide (0.135 mL, 0.552 mmol) and acetonitrile (0.79 g) and stirring the mixture at 50° C. for 1 hour, and the resulting mixture was further stirred for 96 hours while maintaining to 0° C. (starting material:target compound=1:10). The obtained reaction mixture was diluted with ethyl acetate (5.0 g), and washed with a 10 wt % aqueous citric acid solution (2.0 g) and a saturated brine solution (1.0 g) twice. The quantitative yield of Fmoc-Val-MePhe-OH of the collected organic layer was 90%.

Synthetic Example 61: Synthesis of Fmoc-Val-MePhe-OH

Fmoc-Val-OH (0.10 g, 0.30 mmol) and N-methylmorpholine (0.071 mL, 0.65 mmol) were mixed with N,N-dimethylacetamide (5.9 mL), 4-ethyl-2,2-dimethylhexan-3-yl carbonochloridate (0.13 g, 0.59 mmol) was added to the mixture at 0° C. and the resulting mixture was stirred for 2 hours. To the solution was added a solution which had been separately prepared by mixing H-MePhe-OH (0.106 g, 0.59 mmol), N,O-bis(trimethylsilyl)acetamide (0.29 mL, 1.18 mmol) and acetonitrile (7.9 mL) and stirring the mixture at 75° C. for 15 minutes, and the resulting mixture was further stirred for 164 hours while maintaining to 0° C. (starting material:target compound=1:9). The obtained reaction mixture was quenched with methanol (5.0 mL) and N,N-diisopropylethylamine (0.50 mL), then, diluted with ethyl acetate (30.0 g), and washed with a 10 wt % aqueous citric acid solution (18.0 g), a saturated brine solution (10.0 g) and a saturated brine solution (6.0 g) twice. The quantitative yield of Fmoc-Val-MePhe-OH of the collected organic layer was 83%.

Synthetic Example 62: Synthesis of Fmoc-Val-MePhe-OH

Fmoc-Val-OH (0.100 g, 0.295 mmol) and triethylamine (0.053 mL, 0.383 mmol) were mixed with tetrahydrofuran (1.0 g), 2-ethylhexanoyl chloride (0.061 mL, 0.354 mmol) was added to the mixture at 0° C. and the resulting mixture was stirred for 1 hour. To the solution was added a solution which had been separately prepared by mixing H-MePhe-OH (0.079 g, 0.442 mmol), N,O-bis(trimethylsilyl)acetamide (0.135 mL, 0.552 mmol) and acetonitrile (0.79 g) and stirring the mixture at 50° C. for 1 hour, and the resulting mixture was further stirred for 111 hours while maintaining to 0° C. (starting material:target compound=1:11). The obtained reaction mixture was diluted with ethyl acetate (5.0 g), and washed with a 10 wt % aqueous citric acid solution (2.0 g) and a saturated brine solution (1.0 g) twice. The quantitative yield of Fmoc-Val-MePhe-OH of the collected organic layer was 90%.

Synthetic Example 63: Synthesis of Fmoc-Val-MePhe-OH

Fmoc-Val-OH (0.100 g, 0.295 mmol) and triethylamine (0.053 mL, 0.383 mmol) were mixed with tetrahydrofuran (1.0 g), 2-(4-chlorophenyl)-3-methylbutanoyl chloride (0.070 mL, 0.354 mmol) was added to the mixture at 0° C. and the resulting mixture was stirred for 1 hour. To the solution was added a solution which had been separately prepared by mixing H-MePhe-OH (0.079 g, 0.442 mmol), N,O-bis(trimethylsilyl)acetamide (0.135 mL, 0.552 mmol) and acetonitrile (0.79 g) and stirring the mixture at 50° C. for 1 hour, and the resulting mixture was further stirred for 66 hours while maintaining to 0° C. (starting material:target compound=1:10). The obtained reaction mixture was diluted with ethyl acetate (5.0 g), and washed with a 10 wt % aqueous citric acid solution (2.0 g) and a saturated brine solution (1.0 g) twice.

The quantitative yield of Fmoc-Val-MePhe-OH of the collected organic layer was 84%.

Synthetic Example 64: Synthesis of Fmoc-Val-MePhe-OH

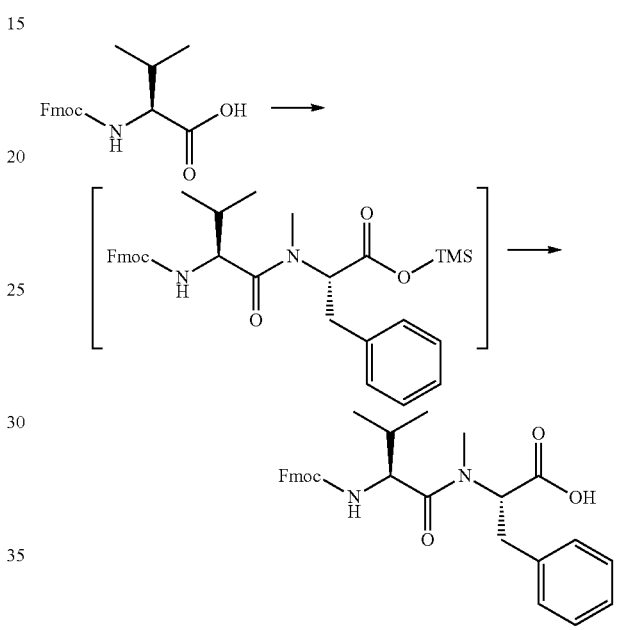

Fmoc-Val-OH (0.100 g, 0.295 mmol) and triethylamine (0.053 mL, 0.383 mmol) were mixed with tetrahydrofuran (1.0 g), 3,5,5-trimethylhexanoyl chloride (0.067 mL, 0.354 mmol) was added to the mixture at 0° C. and the resulting mixture was stirred for 1 hour. To the solution was added a solution which had been separately prepared by mixing H-MePhe-OH (0.079 g, 0.442 mmol), N,O-bis(trimethylsilyl)-acetamide (0.135 mL, 0.552 mmol) and acetonitrile (0.79 g) and stirring the mixture at 50° C. for 1 hour, and the resulting mixture was further stirred for 68 hours while maintaining to 0° C. (starting material:target compound=16:1).

Synthetic Example 65: Synthesis of Cbz-Phe-MePhe-Phe-OH

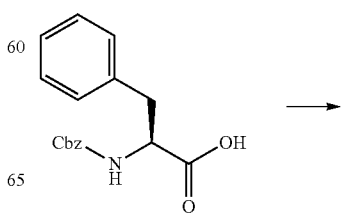

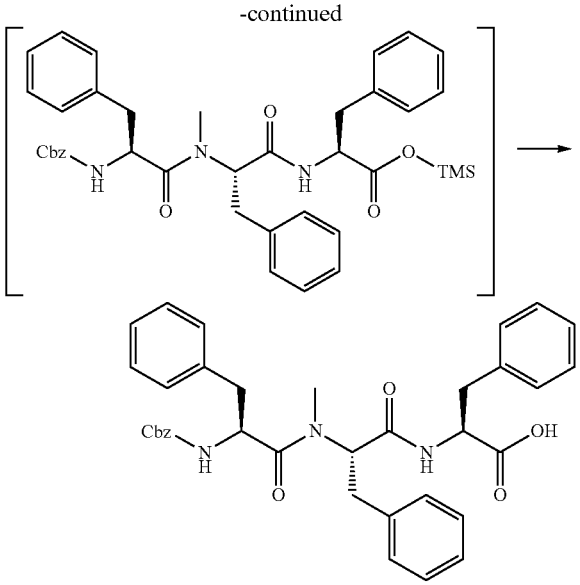

Cbz-Phe-OH (50 mg, 0.17 mmol), tetrahydrofuran (0.5 g) and triethylamine (20 mg, 0.20 mmol) were mixed, pivaloyl chloride (24 mg, 0.20 mmol) was added to the mixture at 0° C. and the resulting mixture was stirred for 2 hours. To the solution was added a solution which had been separately prepared by mixing H-MePhe-Phe-OH (82 mg, 0.25 mmol), N,O-bis(trimethylsilyl)acetamide (97 mg, 0.48 mmol) and acetonitrile (0.82 g) and stirring the mixture at 50° C. for 1 hour, and a temperature of the mixture was raised to 25° C. and the resulting mixture was stirred for 3 hours (starting material:target compound=1:10 (Analytical condition 5)). The obtained reaction mixture was diluted with ethyl acetate (2.5 g), and after separating the liquids with a 10 wt % aqueous citric acid solution (1.0 g), the liquid was washed with a 10 wt % aqueous sodium chloride solution (1.0 g) twice. The quantitative yield of Cbz-Phe-MePhe-Phe-OH of the obtained organic layer was 77% (Analytical condition 5).

MASS (ESI+) m/z; (M+H)+608.44

In the following, otherwise specifically mentioned, the ratio of the starting material Cbz-Phe-OH and the product Cbz-Phe-MePhe-Phe-OH was calculated by the analysis <Analytical condition 5> using high performance liquid chromatography.
<Analytical Condition 5>
High performance liquid chromatography: HPLC-20A manufactured by SHIMADZU Corporation
Column: Poroshell 120EC-C18 (2.7 μm, 3.0×100 mm) manufactured by Agilent Column oven temperature: 50° C.
Eluent: 0.2 vol % phosphoric acid acetonitrile solution: 0.2 vol % phosphoric acid aqueous solution
12:88-95:5 (0-15 min), 95:5 (15-19 min), (v/v)
Eluent speed: 0.7 mL/min
Detection wavelength: 214 nm In the following, otherwise specifically mentioned, the quantitative yield of Cbz-Phe-MePhe-Phe-OH was calculated by the quantitative analysis method by <Analytical condition 5>.
Standard substance: Cbz-Phe-MePhe-Phe-OH synthesized by the method described in Synthetic Example 71 was purified by silica gel chromatography and made the standard substance.
NMR and MASS of the standard substance are shown.
$^1$H NMR (300 MHz, DMSO-$d_6$):
δ ppm: 2.64 (3H, s), 2.67-3.33 (6H, m), 4.27-4.45 (3H, m), 4.89 (2H, s), 5.21 (1H, m), 7.04-7.33 (20H, m)
MASS (ESI+) m/z; (M+H)+608.44
Quantitative method; Absolute calibration method Synthetic Example 66: Synthesis of H-MePhe-Phe-OH

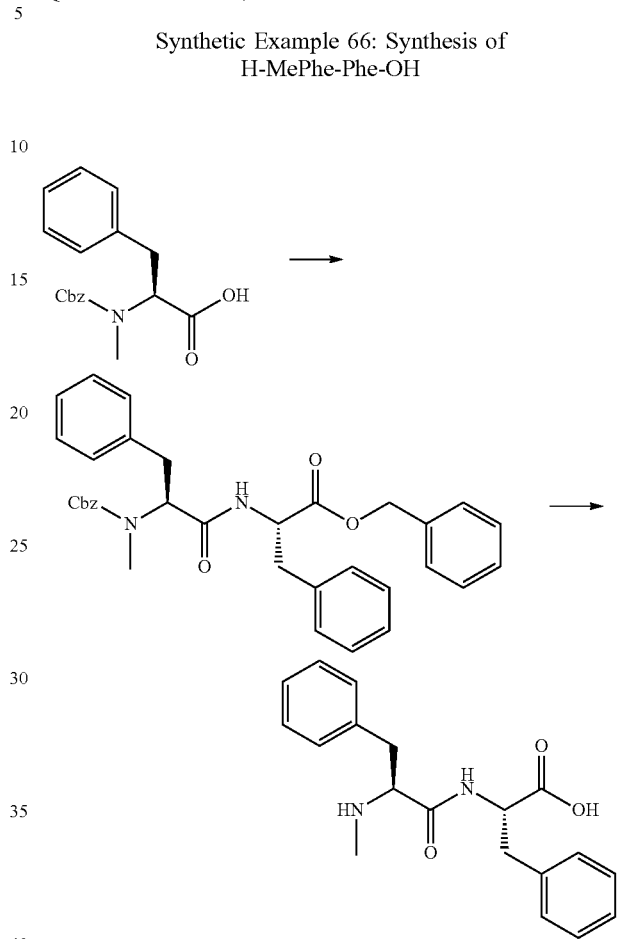

Cbz-MePhe-OH (2.0 g, 6.38 mmol), methylene chloride (20.0 g), N,N-diisopropylethylamine (2.9 g, 22.3 mmol) and H-Phe-OBn (2.2 g, 7.66 mmol) were mixed, N-[1-(cyano-2-ethoxy-2-oxoethylideneaminoxy)dimethylamino(morpholino)]-uronium hexafluorophosphate (3.28 g, 7.66 mmol) was added to the mixture at 22° C. and the resulting mixture was stirred for 1 hour and a half. To the obtained reaction mixture were added 10 wt % hydrochloric acid (16 g) and water (16 g), and after separating the liquids, the organic layer was washed with water twice. Thereafter, a 10 wt % aqueous potassium hydrogen carbonate solution (16 g) and water (16 g) were added thereto, and after the liquids twice, the organic layer was washed with water. The obtained organic layer was concentrated under reduced pressure, the residue was purified by silica gel column chromatography and diluted with trifluoroethanol (40 g). After a 10 wt % Pd—C (0.4 g) was added to the obtained solution, the mixture was stirred under a hydrogen gas atmosphere at room temperature for 14 hours and a half. The operation in which the reaction mixture was concentrated under reduced pressure, the concentrate was diluted with methanol (300 g), the mixture was filtered and the obtained filtrate was diluted again with methanol (300 g), and the mixture was filtered, was repeated three times, and the obtained filtrates were all concentrated and the concentrate was diluted with acetonitrile (100 g), and the mixture was concentrated again to obtain H-MePhe-Phe-OH (1.35 g, yield: 65%) as a white solid.

MASS (ESI+) m/z; (M+H)+327.2

Synthetic Example 67: Synthesis of Cbz-Phe-MePhe-Phe-OH

Cbz-Phe-OH (50 mg, 0.17 mmol), tetrahydrofuran (0.5 g) and N-methyl-morpholine (20 mg, 0.20 mmol) were mixed, isobutyl carbonochloridate (27 mg, 0.20 mmol) was added to the mixture at 0° C. and the resulting mixture was stirred for 3 hours. To the solution was added a solution which had been separately prepared by mixing H-MePhe-Phe-OH (82 mg, 0.25 mmol), N,O-bis(trimethylsilyl)acetamide (97 mg, 0.48 mmol), acetonitrile (0.82 g) and stirring the mixture at 50° C. for 1 hour, and the temperature of the mixture was raised to 25° C. and the resulting mixture was stirred for 3 hours (starting material:target compound=1:1.6). The obtained reaction mixture was diluted with ethyl acetate (2.5 g), and after separating the liquids with a 10 wt % aqueous citric acid solution (1.0 g), the liquid was washed with a 10 wt % aqueous sodium chloride solution (1.0 g) twice. The quantitative yield of Cbz-Phe-MePhe-Phe-OH of the obtained organic layer was 43%.

Synthetic Example 68: Synthesis of Cbz-Phe-MePhe-Phe-OH

Cbz-Phe-OH (50 mg, 0.17 mmol), tetrahydrofuran (0.5 g) and triethylamine (20 mg, 0.20 mmol) were mixed, 2,2-dimethylbutanoyl chloride (27 mg, 0.20 mmol) was added to the mixture at 0° C. and the resulting mixture was stirred for 2 hours. To the solution was added a solution which had been separately prepared by mixing H-MePhe-Phe-OH (82 mg, 0.25 mmol), N,O-bis(trimethylsilyl)acetamide (97 mg, 0.48 mmol) and acetonitrile (0.82 g) and stirring the mixture at 50° C. for 1 hour, and the temperature of the mixture was raised to 25° C. and the resulting mixture was stirred for 21 hours (starting material:target compound=1:24). The obtained reaction mixture was diluted with ethyl acetate (2.5 g), and after separating the liquids with a 10 wt % aqueous citric acid solution (1.0 g), the liquid was washed with a 10 wt % aqueous sodium chloride solution (1.0 g) twice. The quantitative yield of Cbz-Phe-MePhe-Phe-OH of the obtained organic layer was 95%.

Synthetic Example 69: Synthesis of Cbz-Phe-MePhe-Phe-OH

Cbz-Phe-OH (50 mg, 0.17 mmol), tetrahydrofuran (0.5 g) and triethylamine (20 mg, 0.20 mmol) were mixed, 2-ethylbutanoyl chloride (27 mg, 0.20 mmol) was added to the mixture at 0° C. and the resulting mixture was stirred for 2 hours. To the solution was added a solution which had been separately prepared by mixing H-MePhe-Phe-OH (82 mg, 0.25 mmol), N,O-bis(trimethylsilyl)acetamide (97 mg, 0.48 mmol) and acetonitrile (0.82 g) and stirring the mixture at 50° C. for 1 hour, and the temperature of the mixture was raised to 25° C. and the resulting mixture was stirred for 27 hours (starting material:target compound=1:30). The obtained reaction mixture was diluted with ethyl acetate (2.5 g), and after separating the liquids with a 10 wt % aqueous citric acid solution (1.0 g), the liquid was washed with a 10 wt % aqueous sodium chloride solution (1.0 g) twice. The quantitative yield of Cbz-Phe-MePhe-Phe-OH of the obtained organic layer was 102%.

Synthetic Example 70: Synthesis of Cbz-Phe-MePhe-Phe-OH

Cbz-Phe-OH (50 mg, 0.17 mmol), tetrahydrofuran (0.5 g) and triethylamine (20 mg, 0.20 mmol) were mixed and a 50 wt % toluene solution of 2-(4,4-dimethylpentan-2-yl)-5,7,7-trimethyloctanoyl chloride (124 mg, 0.20 mmol) was added to the mixture at 25° C. and the resulting mixture was stirred for 9 hours. To the solution was added a solution which had been separately prepared by mixing H-MePhe-Phe-OH (82 mg, 0.25 mmol), N,O-bis(trimethylsilyl)acetamide (97 mg, 0.48 mmol) and acetonitrile (0.82 g) and stirring the mixture at 50° C. for 1 hour, and the temperature of the mixture was raised to 25° C. and the resulting mixture was stirred for 14 hours (starting material:target compound=1:80). The obtained reaction mixture was diluted with ethyl acetate (2.5 g), and after separating the liquids with a 10 wt % aqueous citric acid solution (1.0 g), the liquid was washed with a 10 wt % aqueous sodium chloride solution (1.0 g) twice. The quantitative yield of Cbz-Phe-MePhe-Phe-OH of the obtained organic layer was 100%.

Synthetic Example 71: Synthesis of Cbz-Phe-MePhe-Phe-OH

Cbz-Phe-OH (99 mg, 0.33 mmol), acetonitrile (1.0 g) and N,N-diisopropyl-ethylamine (52 mg, 0.40 mmol) were mixed, a 50 wt % toluene solution of 2-(4,4-dimethylpentan-2-yl)-5,7,7-trimethyloctanoyl chloride (250 mg, 0.41 mmol) was added to the mixture at room temperature and the resulting mixture was stirred for 2 hours. To the solution was added a solution which had been separately prepared by mixing H-MePhe-Phe-OH (164 mg, 0.50 mmol), N,O-bis(trimethylsilyl)acetamide (195 mg, 0.96 mmol) and acetonitrile (1.6 g) and stirring the mixture at 50° C. for 1 hour, and the temperature of the mixture was raised to 25° C. and the resulting mixture was stirred for 21 hours (starting material:target compound=1:335). The obtained reaction mixture was diluted with ethyl acetate (5.0 g), and after separating the liquids with a 10 wt % aqueous citric acid solution (3.0 g), the liquid was washed with a saturated aqueous sodium chloride solution (2.0 g) twice. The quantitative yield of Cbz-Phe-MePhe-Phe-OH of the obtained organic layer was 100%.

Synthetic Example 72: Synthesis of Cbz-Phe-MePhe-Phe-OH

Cbz-Phe-OH (50 mg, 0.17 mmol), N,N-dimethylacetamide (0.5 g) and N-methylmorpholine (22 mg, 0.22 mmol) were mixed, 2,2,4-trimethylpentan-3-yl carbonochloridate (39 mg, 0.20 mmol) was added to the mixture at 0° C. and the resulting mixture was stirred for 2 hours. To the solution was added a solution which had been separately prepared by mixing H-MePhe-Phe-OH (82 mg, 0.25 mmol), N,O-bis(trimethylsilyl)acetamide (97 mg, 0.48 mmol) and acetonitrile (0.82 g) and stirring the mixture at 50° C. for 1 hour, and the temperature of the mixture was raised to 25° C. and the resulting mixture was stirred for 3 hours (starting material:target compound=1:32). The obtained reaction mixture was diluted with ethyl acetate (2.5 g), and after separating the liquids with a 10 wt % aqueous citric acid solution (1.0 g), the liquid was washed with a 10 wt % aqueous sodium chloride solution (1.0 g) twice. The quantitative yield of Cbz-Phe-MePhe-Phe-OH of the obtained organic layer was 99%.

Synthetic Example 73: Synthesis of Cbz-Phe-MePhe-Phe-OH

Cbz-Phe-OH (50 mg, 0.17 mmol), N,N-dimethylacetamide (0.5 g) and N-methylmorpholine (22 mg, 0.22 mmol) were mixed, 2,4-dimethylpentan-3-yl carbonochloridate (39 mg, 0.20 mmol) was added to the mixture at 0° C. and the resulting mixture was stirred for 1.5 hours. To the solution was added a solution which had been separately prepared by mixing H-MePhe-Phe-OH (82 mg, 0.25 mmol), N,O-bis(trimethylsilyl)acetamide (97 mg, 0.48 mmol) and acetonitrile (0.82 g) and stirring the mixture at 50° C. for 1 hour, and the temperature of the mixture was raised to 25° C. and the resulting mixture was stirred for 29 hours (starting material: target compound=1:15). The obtained reaction mixture was diluted with ethyl acetate (2.5 g), and after separating the liquids with a 10 wt % aqueous citric acid solution (1.0 g), the liquid was washed with a 10 wt % aqueous sodium chloride solution (1.0 g) twice. The quantitative yield of Cbz-Phe-MePhe-Phe-OH of the obtained organic layer was 83%.

Synthetic Example 74: Synthesis of Cbz-Phe-MePhe-Phe-OH

Cbz-Phe-OH (50 mg, 0.17 mmol), tetrahydrofuran (0.5 g) and N,N-diiso-propylethylamine (30 mg, 0.23 mmol) were mixed, 1-adamantanecarbonyl chloride (51 mg, 0.26 mmol) was added to the mixture at 0° C. and the resulting mixture was stirred for 1 hour. To the solution was added a solution which had been separately prepared by mixing H-MePhe-Phe-OH (110 mg, 1.0 mmol), N,O-bis(trimethylsilyl)acetamide (129 mg, 0.63 mmol) and acetonitrile (1.1 g) and stirring the mixture at 50° C. for 1 hour, and the resulting mixture was stirred at 0° C. for 28 hours (starting material: target compound=1:58). The obtained reaction mixture was diluted with ethyl acetate (3.0 g), and after separating the liquids with a 10 wt % aqueous citric acid solution (3.0 g), the liquid was washed with a saturated aqueous sodium chloride solution (1.0 g) twice. The obtained organic layer was quantitated, and Cbz-Phe-MePhe-Phe-OH was obtained with the quantitative yield of 98%.

Synthetic Example 75: Synthesis of Cbz-Phe-MePhe-Phe-OH

Cbz-Phe-OH (0.050 g, 0.17 mmol), N,N-dimethylacetamide (3.0 mL) and N-methylmorpholine (0.040 mL, 0.37 mmol) were mixed, 4-ethyl-2,2-dimethylhexan-3-yl carbonochloridate (0.074 g, 0.33 mmol) was added to the mixture at 0° C. and the resulting mixture was stirred for 1 hour and a half. To the solution was added a solution which had been separately prepared by mixing H-MePhe-Phe-OH (0.109 g, 0.334 mmol), N,O-bis(trimethylsilyl)acetamide (0.16 mL, 0.67 mmol) and acetonitrile (4.0 mL) and stirring the mixture at 50° C. for 1 hour, and the temperature of the mixture was raised to room temperature and the resulting mixture was stirred for 21 hours (starting material:target compound=1:43). The obtained reaction mixture was diluted with ethyl acetate (15 g), and after separating the liquids with a 10 wt % aqueous citric acid solution (9.0 g) and a saturated brine solution (5.0 g), the liquid was washed with a saturated brine solution (3.0 g) twice. The quantitative yield of Cbz-Phe-MePhe-Phe-OH of the obtained organic layer was 92%.

Synthetic Example 76: Synthesis of Cbz-Phe-MePhe-Phe-OH

Cbz-Phe-OH (50 mg, 0.17 mmol), N,N-dimethylacetamide (0.5 g) and N-methylmorpholine (22 mg, 0.22 mmol) were mixed, 3,3-dimethylbutan-2-yl carbonochloridate (39 mg, 0.20 mmol) was added to the mixture at 0° C. and the resulting mixture was stirred for 1.5 hours. To the solution was added a solution which had been separately prepared by mixing H-MePhe-Phe-OH (82 mg, 0.25 mmol), N,O-bis(trimethylsilyl)acetamide (97 mg, 0.48 mmol) and acetonitrile (0.82 g) and stirring the mixture at 50° C. for 1 hour, and the temperature of the mixture was raised to 25° C. and the resulting mixture was stirred for 16 hours (starting material: target compound=1:1.2).

Synthetic Example 77: Synthesis of Boc-Val-Pro-OH

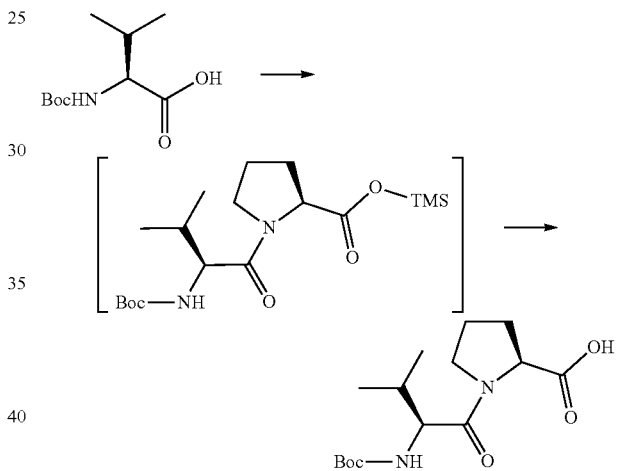

Boc-Val-OH (128 mg, 0.59 mmol), tetrahydrofuran (1.3 g) and N-methyl-morpholine (60 mg, 0.59 mmol) were mixed, isobutyl carbonochloridate (72 mg, 0.59 mol) was added to the mixture at 0° C. and the resulting mixture was stirred for 2.5 hours. To the solution was added a solution which had been separately prepared by mixing H-Pro-OH (71 mg, 0.62 mmol), N,N-diisopropylethylamine (0.16 g, 1.2 mmol), trimethylsilyl chloride (0.13 g, 1.2 mmol) and dichloromethane (3 mL) and stirring the mixture at 40° C. for 2 hours, and the resulting mixture was stirred for 15 hours while maintaining to 0° C. to obtain Boc-Val-Pro-OH (starting material:target compound=1:15).

MASS (ESI+) m/z; (M+H)+315.20

In the following, otherwise specifically mentioned, the ratio of the starting material Boc-Val-OH and the product Boc-Val-Pro-OH was calculated by the analysis <Analytical condition 5> using high performance liquid chromatography.

Synthetic Example 78: Synthesis of Boc-Val-Pro-OH

Boc-Val-OH (128 mg, 0.59 mmol), acetonitrile (1.3 g) and N,N-diisopropyl-ethylamine (91 mg, 0.71 mmol) were mixed, a 50 wt % toluene solution of 2-(4,4-dimethylpentan-2-yl)-5,7,7-trimethyloctanoyl chloride (0.43 g, 0.71 mol) was added to the mixture at 25° C. and the resulting mixture was stirred for 4 hours. To the solution was added a solution which had been separately prepared by mixing H-Pro-OH (71 mg, 0.62 mmol), N,O-bis(trimethylsilyl)acetamide (0.22 g, 1.1 mmol) and acetonitrile (1.3 g) and stirring the mixture at 50° C. for 1 hour, and the resulting mixture was stirred for 15 hours while maintaining to 25° C. (starting material: target compound=1:731). The obtained reaction mixture was diluted with ethyl acetate (10 mL), and after separating the liquids with water (2 mL) and a 10 wt % aqueous citric acid solution (2 mL), the liquid was successively washed with a 5 wt % aqueous sodium chloride solution (5 mL) and water (5 mL). The quantitative yield of Boc-Val-Pro-OH of the obtained organic layer was 94%.

In the following, otherwise specifically mentioned, the quantitative yield of Boc-Val-Pro-OH was calculated by the quantitative analysis method by <Analytical condition 5>.

Standard substance: Boc-Val-Pro-OH separately isolated and purified with reference to Indian Journal of Chemistry, 2004, vol. 43B, p. 1282 was made the standard substance. MASS of the standard substance is shown.

MASS (ESI+) m/z; (M+H)+315.20

Quantitative method; Absolute calibration method

Synthetic Example 79: Synthesis of Boc-Val-Pro-OH

Boc-Val-OH (50 mg, 0.23 mmol), N,N-dimethylacetamide (1.0 g) and N-methylmorpholine (30 mg, 0.30 mmol) were mixed, 2,2,4-trimethylpentan-3-yl carbonochloridate (53 mg, 0.28 mmol) was added to the mixture at 0° C. and the resulting mixture was stirred for 2.5 hours. To the solution was added a solution which had been separately prepared by mixing H-Pro-OH (34 mg, 0.77 mmol), N,O-bis(trimethylsilyl)acetamide (0.80 g, 1.0 mmol) and acetonitrile (0.50 g) and stirring the mixture at 50° C. for 1 hour, and the resulting mixture was stirred for 15 hours while maintaining to 0° C. (starting material:target compound=1:99). The obtained reaction mixture was diluted with ethyl acetate (5 mL), and after separating the liquids with a 10 wt % aqueous citric acid solution (2 mL), the liquid was washed with a 10 wt % aqueous sodium chloride solution (1.0 g) twice. The quantitative yield of Boc-Val-Pro-OH of the obtained organic layer and the aqueous layer was 90%.

Synthetic Example 80: Synthesis of Boc-Val-Pro-OH

Boc-Val-OH (100 mg, 0.46 mmol), tetrahydrofuran (1.0 g) and N,N-diisopropylethylamine (77 mg, 0.60 mmol) were mixed, 2,2-dimethylbutanoyl chloride (74 mg, 0.55 mmol) was added to the mixture at 0° C. and the resulting mixture was stirred for 2 hours. To the solution was added a solution which had been separately prepared by mixing H-Pro-OH (64 mg, 0.55 mmol), N,O-bis(trimethylsilyl)acetamide (0.18 g, 0.87 mmol) and acetonitrile (1.0 g) and stirring the mixture at 50° C. for 1 hour, and the resulting mixture was stirred for 21 hours while maintaining to 0° C. (starting material: target compound=1:520). The obtained reaction mixture was diluted with ethyl acetate (10 mL), and after separating the liquids with water (2 mL) and a 10 wt % aqueous citric acid solution (2 mL), the liquid was washed with a 10 wt % aqueous sodium chloride solution (2 mL) twice. The quantitative yield of Boc-Val-Pro-OH of the obtained organic layer was 99%.

Synthetic Example 81: Synthesis of Boc-Val-Pro-OH

Boc-Val-OH (100 mg, 0.46 mmol), tetrahydrofuran (1.0 g), N,N-diisopropylethylamine (77 mg, 0.60 mmol) were mixed, 2-ethylbutanoyl chloride (74 mg, 0.55 mmol) was added to the mixture at 0° C. and the resulting mixture was stirred for 2 hours. To the solution was added a solution which had been separately prepared by mixing H-Pro-OH (64 mg, 0.55 mmol), N,O-bis(trimethylsilyl)acetamide (0.18 g, 0.87 mmol) and acetonitrile (1.0 g) and stirring the mixture at 50° C. for 1 hour, and the resulting mixture was stirred for 21 hours while maintaining to 0° C. (starting material: target compound=1:248). The obtained reaction mixture was diluted with ethyl acetate (10 mL), and after separating the liquids with water (2 mL) and a 10 wt % aqueous citric acid solution (2 mL), the liquid was washed with a 10 wt % aqueous sodium chloride solution (2 mL) twice. The quantitative yield of Boc-Val-Pro-OH of the obtained organic layer was 99%.

Synthetic Example 82: Synthesis of Boc-Val-Pro-OH

Boc-Val-OH (100 mg, 0.46 mmol), N,N-dimethylacetamide (1.0 g) and N-methylmorpholine (61 mg, 0.60 mmol) were mixed, 2,4-dimethylpentan-3-yl carbonochloridate (99 mg, 0.55 mmol) was added to the mixture at 0° C. and the resulting mixture was stirred for 2.5 hours. To the solution was added a solution which had been separately prepared by mixing H-Pro-OH (64 mg, 0.55 mmol), N,O-bis(trimethylsilyl)acetamide (0.18 g, 0.88 mmol) and acetonitrile (1.0 g) and stirring the mixture at 50° C. for 1 hour, and the resulting mixture was stirred for 21 hours while maintaining to 0° C. (starting material:target compound=1:179). The obtained reaction mixture was diluted with ethyl acetate (5 mL), and after separating the liquids with a 10 wt % aqueous citric acid solution (2 mL), the liquid was washed with a 10 wt % aqueous sodium chloride solution (1.0 g) twice. The quantitative yield of Boc-Val-Pro-OH of the obtained organic layer and the aqueous layer was 89%.

Synthetic Example 83: Synthesis of Fmoc-Val-MeGly-OH

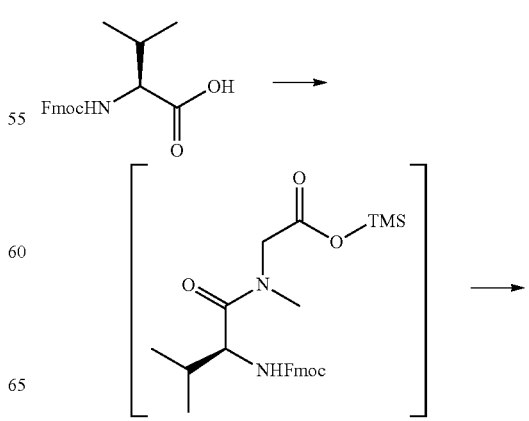

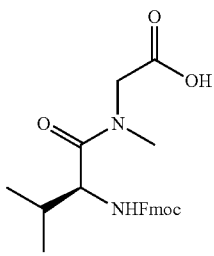

Fmoc-Val-OH (200 mg, 0.59 mmol), tetrahydrofuran (2.0 g) and N-methyl-morpholine (60 mg, 0.59 mmol) were mixed, isobutyl carbonochloridate (72 mg, 0.59 mmol) was added to the mixture at 0° C. and the resulting mixture was stirred for 2.5 hours. To the solution was added a solution which had been separately prepared by mixing H-MeGly-OH (55 mg, 0.62 mmol), N,N-diisopropylethylamine (0.16 g, 1.2 mmol), trimethylsilyl chloride (0.13 g, 1.2 mmol) and dichloromethane (3 mL) and stirring the mixture at 40° C. for 2 hours, and the resulting mixture was stirred for 15 hours while maintaining to 0° C. to obtain Fmoc-Val-MeGly-OH (starting material:target compound=1:1.9).

MASS (ESI+) m/z; (M+H)+411.28

In the following, otherwise specifically mentioned, the ratio of the starting material Fmoc-Val-OH and the product Fmoc-Val-MeGly-OH was calculated by the analysis <Analytical condition 5> using high performance liquid chromatography.

Synthetic Example 84: Synthesis of Fmoc-Val-MeGly-OH

Fmoc-Val-OH (200 mg, 0.59 mmol), acetonitrile (2.0 g) and N,N-diisopropyl-ethylamine (91 mg, 0.71 mmol) were mixed, a 50 wt % toluene solution of 2-(4,4-dimethylpentan-2-yl)-5,7,7-trimethyloctanoyl chloride (0.43 g, 0.71 mmol) was added to the mixture at 25° C. and the resulting mixture was stirred for 4 hours. To the solution was added a solution which had been separately prepared by mixing H-MeGly-OH (79 mg, 0.88 mmol), N,O-bis(trimethylsilyl)acetamide (0.22 g, 1.1 mmol) and acetonitrile (2.0 g) and stirring the mixture at 75° C. for 1 hour, and the resulting mixture was stirred for 15 hours while maintaining to 25° C. (starting material:target compound=1:61). The obtained reaction mixture was diluted with ethyl acetate (3.0 g), and after separating the liquids with a 10 wt % aqueous citric acid solution (2.0 g), the liquid was washed with a 10 wt % aqueous sodium chloride solution (1.0 g) twice. The quantitative yield of Fmoc-Val-MeGly-OH of the obtained organic layer was 97%.

In the following, otherwise specifically mentioned, the quantitative yield of Fmoc-Val-MeGly-OH was calculated by the quantitative analysis method by <Analytical condition 5>.

Standard substance: Fmoc-Val-MeGly-OH separately isolated and purified with reference to Indian Journal of Chemistry, 2004, vol. 43B, p. 1282 was made the standard substance.

MASS of the standard substance is shown.

MASS (ESI+) m/z; (M+H)+411.28

Quantitative Method; Absolute Calibration Method

Synthetic Example 85: Synthesis of Fmoc-Val-MeGly-OH

Fmoc-Val-OH (200 mg, 0.59 mmol), N,N-dimethylacetamide (2.0 g) and N-methylmorpholine (78 mg, 0.77 mmol) were mixed, 2,2,4-trimethylpentan-3-yl carbonochloridate (0.14 g, 0.71 mmol) was added to the mixture at 0° C. and the resulting mixture was stirred for 2.5 hours. To the solution was added a solution which had been separately prepared by mixing H-MeGly-OH (79 mg, 0.88 mmol), N,O-bis(trimethylsilyl)acetamide (0.22 g, 1.1 mmol) and acetonitrile (2.0 g) and stirring the mixture at 75° C. for 1 hour, and the resulting mixture was stirred for 15 hours while maintaining to 0° C. (starting material:target compound=1:64). The obtained reaction mixture was diluted with ethyl acetate (10 mL), and after separating the liquids with water (5 mL) and a 10 wt % aqueous citric acid solution (5 mL), the aqueous layer was extracted with ethyl acetate (10 mL). The organic layers were mixed and washed with a 10 wt % aqueous sodium chloride solution. The quantitative yield of Fmoc-Val-MeGly-OH of the obtained organic layer was 97%.

Synthetic Example 86: Synthesis of Fmoc-Val-MeGly-OH

Fmoc-Val-OH (100 mg, 0.29 mmol), tetrahydrofuran (1.0 g) and N,N-diisopropylethylamine (50 mg, 0.38 mmol) were mixed, 2,2-dimethylbutanoyl chloride (48 mg, 0.35 mmol) was added to the mixture at 0° C. and the resulting mixture was stirred for 2 hours. To the solution was added a solution which had been separately prepared by mixing H-MeGly-OH (32 mg, 0.35 mmol), N,O-bis(trimethylsilyl)acetamide (0.11 g, 0.55 mmol) and acetonitrile (1.0 g) and stirring the mixture at 75° C. for 1 hour, and the resulting mixture was stirred for 20 hours while maintaining to 0° C. (starting material:target compound=1:48). The obtained reaction mixture was diluted with ethyl acetate (5.0 mL), and after separating the liquids with a 10 wt % aqueous citric acid solution (2.0 mL), the liquid was washed with a 10 wt % aqueous sodium chloride solution (2.0 mL) twice. The quantitative yield of Fmoc-Val-MeGly-OH of the obtained organic layer was 95%.

Synthetic Example 87: Synthesis of Fmoc-Val-MeGly-OH

Fmoc-Val-OH (100 mg, 0.29 mmol), tetrahydrofuran (1.0 g) and N,N-diisopropylethylamine (50 mg, 0.38 mmol) were mixed, 2-ethylbutanoyl chloride (48 mg, 0.35 mmol) was added to the mixture at 0° C. and the resulting mixture was stirred for 2 hours. To the solution was added a solution which had been separately prepared by mixing H-MeGly-OH (32 mg, 0.35 mmol), N,O-bis(trimethylsilyl)acetamide (0.11 g, 0.55 mmol) and acetonitrile (1.0 g) and stirring the mixture at 75° C. for 1 hour, and the resulting mixture was stirred for 20 hours while maintaining to 0° C. (starting material:target compound=1:20). The obtained reaction mixture was diluted with ethyl acetate (5.0 mL), and after separating the liquids with a 10 wt % aqueous citric acid solution (2.0 mL), the liquid was washed with a 10 wt % aqueous sodium chloride solution (2.0 mL) twice. The quantitative yield of Fmoc-Val-MeGly-OH of the obtained organic layer was 92%.

Synthetic Example 88: Synthesis of Fmoc-Val-MeGly-OH

Fmoc-Val-OH (100 mg, 0.29 mmol), N,N-dimethylacetamide (1.0 g) and N-methylmorpholine (39 mg, 0.38 mmol) were mixed, 2,4-dimethylpentan-3-yl carbonochloridate (63 mg, 0.35 mmol) was added to the mixture at 0° C. and the resulting mixture was stirred for 2 hours. To the solution was added a solution which had been separately prepared by mixing H-MeGly-OH (32 mg, 0.35 mmol), N,O-bis(trimethylsilyl)acetamide (0.11 g, 0.55 mmol) and acetonitrile (1.0 g) and stirring the mixture at 75° C. for 1 hour, and the resulting mixture was stirred for 20 hours while maintaining to 0° C. (starting material:target compound=1:33). The obtained reaction mixture was diluted with ethyl acetate (5.0 mL), and after separating the liquids with a 10 wt % aqueous citric acid solution (2.0 mL), the liquid was washed with a 10 wt % aqueous sodium chloride solution (2.0 mL) twice. The quantitative yield of Fmoc-Val-MeGly-OH of the obtained organic layer and the aqueous layer was 88%.

Synthetic Example 89: Synthesis of Boc-Cys(Bn)-Pro-OH

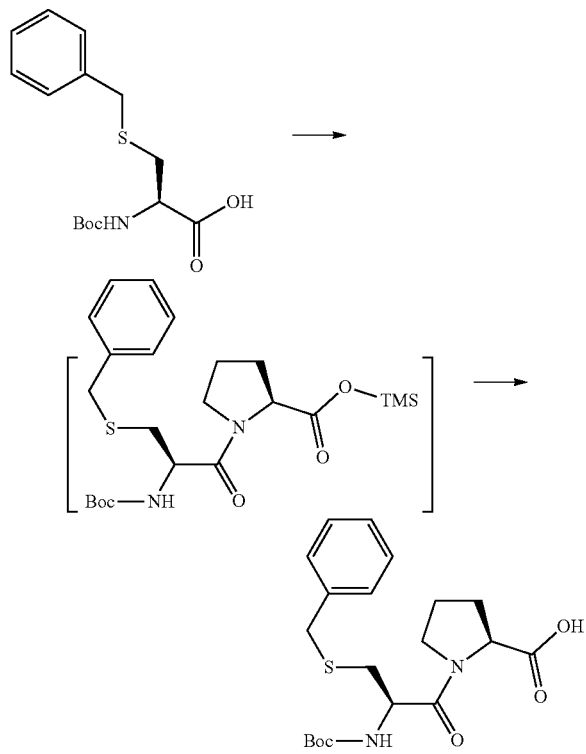

Boc-Cys(Bn)-OH (200 mg, 0.64 mmol), chloroform (1.3 mL) and triethyl-amine (67 mg, 0.66 mmol) were mixed, pivaloyl chloride (81 mg, 0.67 mmol) was added to the mixture at −20° C. and the resulting mixture was stirred for 1 hour. To the solution was added a solution which had been separately prepared by mixing H-Pro-OH (96 mg, 0.84 mmol), triethylamine (0.16 g, 1.6 mmol), trimethylsilyl chloride (0.11 g, 1.0 mmol), dichloromethane (1.6 mL) and N,N-dimethylformamide (0.32 mL) and stirring the mixture at 40° C. for 2 hours, and the resulting mixture was stirred for 3 hours while maintaining to −20° C. to obtain Boc-Cys (Bn)-Pro-OH (starting material:target compound=1:2.2).

MASS (ESI+) m/z; (M+H)+409.26

In the following, otherwise specifically mentioned, the ratio of the starting material Boc-Cys(Bn)-OH and the product Boc-Cys(Bn)-Pro-OH was calculated by the analysis <Analytical condition 6> using high performance liquid chromatography.

<Analytical Condition 6>
High performance liquid chromatography: HPLC-20A manufactured by Shimadzu Corporation
Column: Poroshell 120EC-C18 (2.7 μm, 3.0×100 mm) manufactured by Agilent Column oven temperature: 50° C.
Eluent: 0.2 vol % phosphoric acid acetonitrile solution:0.2 vol % phosphoric acid aqueous solution
35:65 (7 min), 35:65-95:5 (7-14 min), 95:5 (14-18 min), (v/v)
Eluent speed: 0.7 mL/min
Detection wavelength: 214 nm

Synthetic Example 90: Synthesis of Boc-Cys(Bn)-Pro-OH

Boc-Cys(Bn)-OH (100 mg, 0.32 mmol), acetonitrile (1.0 g) and N,N-diisopropylethylamine (50 mg, 0.39 mmol) were mixed, a 50 wt % toluene solution of 2-(4,4-dimethylpentan-2-yl)-5,7,7-trimethyloctanoyl chloride (231 mg, 0.39 mmol) was added to the mixture at 25° C. and the resulting mixture was stirred for 2 hours. To the solution was added a solution which had been separately prepared by mixing H-Pro-OH (48 mg, 0.42 mmol), N,O-bis(trimethylsilyl)acetamide (0.12 g, 0.59 mmol) and acetonitrile (1.0 g) and stirring the mixture at 50° C. for 1 hour, and the resulting mixture was stirred for 23 hours while maintaining to 25° C. (starting material:target compound=1:265). The obtained reaction mixture was diluted with ethyl acetate (3.0 g), and after separating the liquids with a 10 wt % aqueous citric acid solution (2.0 g), the liquid was washed with a 10 wt % aqueous sodium chloride solution (1.0 g) twice. The obtained organic layer and the aqueous layer were quantitated, and Boc-Cys(Bn)-Pro-OH was obtained with the quantitative yield of 97%.

In the following, otherwise specifically mentioned, the quantitative yield of Boc-Cys(Bn)-Pro-OH was calculated by the quantitative analysis method by <Analytical condition 6>.

Standard substance: Boc-Cys(Bn)-Pro-OH separately isolated and purified with reference to Chemistry of Nature Compounds, 1992, vol. 28, p. 344 was made the standard substance.

MASS of the standard substance is shown.
MASS (ESI+) m/z; (M+H)+409.26 Quantitative method; Absolute calibration method

Synthetic Example 91: Synthesis of Boc-Cys(Bn)-Pro-OH

Boc-Cys(Bn)-OH (100 mg, 0.32 mmol), N,N-dimethylacetamide (1.0 g), N-methylmorpholine (42 mg, 0.42 mmol) were mixed, 2,2,4-trimethylpentan-3-yl carbonochloridate (74 mg, 0.39 mmol) was added to the mixture at 0° C. and the resulting mixture was stirred for 2 hours. To the solution was added a solution which had been separately prepared by mixing H-Pro-OH (48 mg, 0.42 mmol), N,O-bis(trimethylsilyl)acetamide (0.12 g, 0.59 mmol) and acetonitrile (1.0 g) and stirring the mixture at 50° C. for 1 hour, and the resulting mixture was stirred for 15 hours while maintaining to 0° C. (starting material:target compound=1:461). The obtained reaction mixture was diluted with ethyl acetate (3.0 g), and after separating the liquids with a 10 wt % aqueous citric acid solution (2.0 g), the liquid was washed with a 10 wt % aqueous sodium chloride solution (1.0 g) twice. The obtained organic layer and the aqueous layer were quantitated, and Boc-Cys(Bn)-Pro-OH was obtained with the quantitative yield of 96%.

Synthetic Example 92: Synthesis of Boc-Cys(Bn)-Pro-OH

Boc-Cys(Bn)-OH (100 mg, 0.32 mmol), acetonitrile (1.0 g) and N,N-diisopropylethylamine (54 mg, 0.41 mmol) were mixed, 2,2-dimethylbutanoyl chloride (52 mg, 0.38 mmol) was added to the mixture at 0° C. and the resulting mixture was stirred for 2 hours. To the solution was added a solution which had been separately prepared by mixing H-Pro-OH (44 mg, 0.38 mmol), N,O-bis(trimethylsilyl)acetamide (0.12 g, 0.61 mmol) and acetonitrile (1.0 g) and stirring the mixture at 50° C. for 1 hour, and the resulting mixture was stirred for 19 hours while maintaining to 0° C. (starting material:target compound=1:31). The obtained reaction mixture was diluted with ethyl acetate (5.0 mL), and after separating the liquids with a 10 wt % aqueous citric acid solution (2.0 mL), the liquid was washed with a 10 wt % aqueous sodium chloride solution (2.0 mL) twice. The obtained organic layer was quantitated, and Boc-Cys(Bn)-Pro-OH was obtained with the quantitative yield of 97%.

Synthetic Example 93: Synthesis of Boc-Cys(Bn)-Pro-OH

Boc-Cys(Bn)-OH (100 mg, 0.32 mmol), acetonitrile (1.0 g) and N,N-diisopropylethylamine (54 mg, 0.41 mmol) were mixed, 2-ethylbutanoyl chloride (52 mg, 0.38 mmol) was added to the mixture at 0° C. and the resulting mixture was stirred for 2 hours. To the solution was added a solution which had been separately prepared by mixing H-Pro-OH (44 mg, 0.38 mmol), N,O-bis(trimethylsilyl)acetamide (0.12 g, 0.61 mmol) and acetonitrile (1.0 g) and stirring the mixture at 50° C. for 1 hour, and the resulting mixture was stirred for 19 hours while maintaining to 0° C. (starting material:target compound=1:30). The obtained reaction mixture was diluted with ethyl acetate (5.0 mL), and after separating the liquids with a 10 wt % aqueous citric acid solution (2.0 mL), the liquid was washed with a 10 wt % aqueous sodium chloride solution (2.0 mL) twice. The obtained organic layer was quantitated, and Boc-Cys(Bn)-Pro-OH was obtained with the quantitative yield of 97%.

Synthetic Example 94: Synthesis of Boc-Cys(Bn)-Pro-OH

Boc-Cys(Bn)-OH (100 mg, 0.32 mmol), N,N-dimethylacetamide (1.0 g) and N-methylmorpholine (42 mg, 0.42 mmol) were mixed, 2,4-dimethylpentan-3-yl carbonochloridate (69 mg, 0.38 mmol) was added to the mixture at 0° C. and the resulting mixture was stirred for 2 hours. To the solution was added a solution which had been separately prepared by mixing H-Pro-OH (48 mg, 0.42 mmol), N,O-bis(trimethylsilyl)acetamide (0.12 g, 0.59 mmol) and acetonitrile (1.0 g) and stirring the mixture at 50° C. for 1 hour, and the resulting mixture was stirred for 19 hours while maintaining to 0° C. (starting material:target compound=1:60). The obtained reaction mixture was diluted with ethyl acetate (5.0 mL), and after separating the liquids with a 10 wt % aqueous citric acid solution (2.0 mL), the liquid was washed with a 10 wt % aqueous sodium chloride solution (2.0 g) twice. The obtained organic layer was quantitated, and Boc-Cys(Bn)-Pro-OH was obtained with the quantitative yield of 98%.

Synthetic Example 95: Synthesis of Cbz-Phe-Phe-MePhe-OH

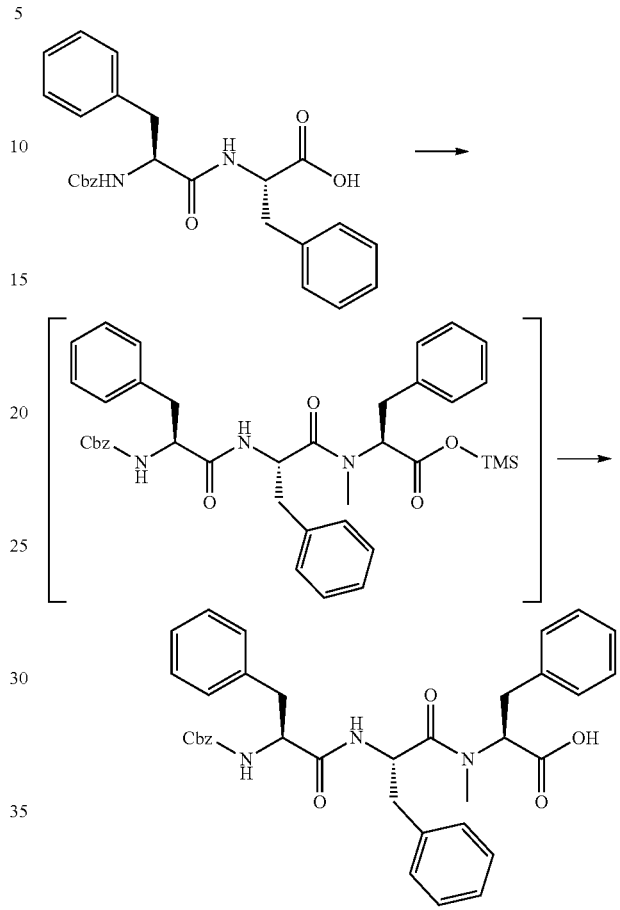

Cbz-Phe-Phe-OH (0.100 g, 0.224 mmol) and N,N-diisopropylethylamine (0.050 mL, 0.291 mmol) were mixed with tetrahydrofuran (1.0 g), 1-adamantane-carbonyl chloride (0.0534 g, 0.269 mmol) was added to the mixture at 0° C. and the resulting mixture was stirred for 1 hour. To the solution was added a solution which had been separately prepared by mixing H-MePhe-OH (0.060 g, 0.336 mmol), N,O-bis(trimethylsilyl)acetamide (0.103 mL, 0.420 mmol) and acetonitrile (0.60 g) and stirring the mixture at 50° C. for 1 hour, and the resulting mixture was further stirred for 22 hours while maintaining to 0° C. (starting material:target compound=1:32). The obtained reaction mixture was quenched with 2% n-propylamine/acetonitrile solution, and after diluting with ethyl acetate (5.0 g), the liquid was washed with a 10 wt % aqueous citric acid solution (2.0 g) and a saturated brine solution (1.0 g) twice. The quantitative yield of Cbz-Phe-Phe-MePhe-OH of the collected organic layer was 89%.

The ratio of the starting material Cbz-Phe-Phe-OH and the product Cbz-Phe-Phe-MePhe-OH was calculated by the analysis <Analytical condition 7> using high performance liquid chromatography.
<Analytical Condition 7>
High performance liquid chromatography: HPLC LC-20A manufactured by Shimadzu Corporation
Column:Poroshell 120EC-C18 (2.7 μm, 3.0×100 mm) manufactured by Agilent Column oven temperature: 50° C.
Eluent: 0.2 vol % TFA/acetonitrile:methanol=1:1
0.2 vol % TFA aqueous solution
55:45 (0-20 min), 55:45-95:5 (20-20.1 min), 95:5 (20.1-24 min) Post time 5 minutes (v/v)
Eluent speed: 0.7 mL/min
Detection wavelength: 214 nm The quantitative yield of Cbz-Phe-Phe-MePhe-OH was calculated by the quantitative analysis method by <Analytical condition 7>.
Standard substance: Cbz-Phe-Phe-MePhe-OH synthesized in Synthetic Example 96 was made the standard substance.
MASS of the standard substance is shown.
MASS (ESI+) m/z; (M+H)+608.4
Quantitative Method; Absolute Calibration Method Synthetic Example 96: Synthesis of Cbz-Phe-Phe-MePhe-OH To 2-chlorotrityl chloride resin (200-400 mesh) (0.10 g, 0.13 mmol) were added dichloromethane (1.0 mL), Fmoc-MePhe-OH (0.062 g, 0.15 mmol) and N,N-diisopropylethylamine (0.11 mL, 0.61 mmol) and the mixture was stirred overnight. To the obtained suspension were successively added the following solutions and filtered each time. (1) A mixed solution of (dichloromethane/methanol/N,N-diisopropylethyl-amine=17/2/1) three times, (2) dichloromethane three times, (3) N-methylpyrrolidone twice, (4) dichloromethane twice, and (5) methanol five times. N-methylpyrrolidone was added thereto so that the resin after filtration was sufficiently immersed, and the mixture was stirred for 15 minutes. Thereafter, filtration was carried out, 20% piperidine/N-methylpyrrolidone solution was added thereto so that the resin after filtration was sufficiently immersed, and the mixture was stirred for 20 minutes. Subsequently, filtration was carried out, and the resin was washed with N-methyl-pyrrolidone 10 times. To the obtained resin (0.10 g, 0.050 mmol) were added 0.80 mL of 0.5M ethylcyano (hydroxyimino)acetate/N-methylpyrrolidone solution, Fmoc-Phe-OH (0.078 mg, 0.20 mmol), N-[1-(cyano-2-ethoxy-2-oxoethylideneaminoxy)-dimethylamino (morpholino)]uronium hexafluorophosphate (0.086 g, 0.20 mmol) and N,N-diisopropylethylamine (0.085 mL, 0.50 mmol), and the mixture was stirred for 2 hours. The reaction solution was filtered, and the resin was washed with N-methylpyrrolidone 10 times. Thereafter, the above-mentioned condensation and washing operations were carried out again, and after addition of 20% piperidine/N-methylpyrrolidone, stirring for 20 minutes and washing with N-methylpyrrolidone were carried out 10 times. To the obtained resin were added 0.400 mL of 0.5M ethylcyano-(hydroxyimino)acetate/N-methylpyrrolidone solution, Cbz-Phe-OH (0.060 mg, 0.20 mmol) and N,N-diisopropylcarbodiimide (0.032 mL, 0.20 mmol), and the mixture was stirred overnight. The reaction solution was filtered, and then, the resin was washed with N-methylpyrrolidone 10 times and with methanol 10 times, and 30% hexafluoroisopropanol was added thereto so that the resin was sufficiently immersed, and the operations of stirring the mixture for 10 minutes and then filtration were carried out 5 times. The collected solution was concentrated under reduced pressure and as a result, Cbz-Phe-Phe-MePhe-OH (0.031 g, 100%) was obtained.
MASS (ESI+) m/z; (M+H)+608.4

In the above-mentioned Synthetic Example, Synthetic Examples 1 to 7, 66 and 96 are Reference Examples relating to syntheses of starting materials used in Examples, and Synthetic Examples 1 to 2 and Synthetic Examples 3 to 4 are also Examples of the invention relating to the compounds of the present application. In addition, Synthetic Examples 8 to 13, 18 to 28, 32 to 35, 38, 41 to 48, 51, 55 to 63, 68 to 76, 78 to 82, 84 to 88, and 90 to 95 are Examples of the invention relating to the method for producing the peptide of the present application, and Synthetic Examples 14 to 17, 29 to 31, 36 to 37, 39 to 40, 49 to 50, 52 to 54, 64 to 65, 67, 77, 83, 89 and 96 are Comparative Examples thereof.

Synthetic Example 97: Synthesis of Fmoc-Val-MeTyr(tBu)-OH

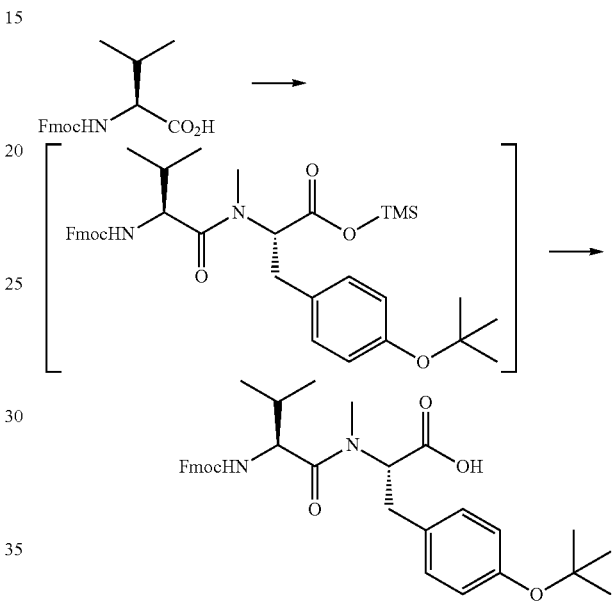

Fmoc-Val-OH (0.102 g, 0.30 mmol) was mixed with tetrahydrofuran (1.5 mL), triethylamine (0.050 mL, 0.36 mmol) and pivaloyl chloride (0.041 mL, 0.33 mmol) were added to the mixture at 0° C. and the resulting mixture was stirred at 0° C. for 2 hours. To the solution was added a solution which had been separately prepared by mixing H-MeTyr(tBu)-OH (0.090 g, 0.36 mmol), N,O-bis(trimethylsilyl)acetamide (0.19 mL, 0.72 mmol) and acetonitrile (1.5 mL) and stirring the mixture at 50° C. for 1 hour, and after the resulting mixture was further stirred at 0° C. for 1 hour, the mixture was stirred at 25° C. for 20 hours (starting material:target compound=1:7 (Analytical condition 3)). The obtained reaction mixture was diluted with ethyl acetate (20 mL), and successively washed with a saturated aqueous sodium hydrogen carbonate solution (20 mL), water (5 mL) and a saturated aqueous sodium chloride solution (5 mL). The obtained organic layer was concentrated to obtain Fmoc-Val-MeTyr(tBu)-OH (0.18 g, yield: 106%) as a pale yellowish solid.

Synthetic Example 98: Synthesis of Fmoc-Val-MeTyr(tBu)-OH

Fmoc-Val-OH (0.068 g, 0.20 mmol) was mixed with tetrahydrofuran (1.0 mL), triethylamine (0.033 mL, 0.24 mmol) and 2-(4,4-dimethylpentan-2-yl)-5,7,7-trimethyl-octanoyl chloride (0.66 g, 0.22 mmol) were added to the mixture at 0° C. and the resulting mixture was stirred for 2 hours. To the solution was added a solution which had been separately prepared by mixing H-MeTyr(tBu)-OH (0.090 g, 0.36 mmol), N,O-bis(trimethylsilyl)acetamide (0.185 mL, 0.72 mmol) and acetonitrile (1.5 mL) and stirring the mixture at 50° C. for 1 hour, and after the resulting mixture was further stirred at 0° C. for 1 hour, the mixture was stirred at 25° C. for 24 hours (starting material:target compound=1: 20 (Analytical condition 3)). The obtained reaction mixture was diluted with ethyl acetate (5 mL), a saturated aqueous sodium hydrogen carbonate solution (5 mL) was added thereto, and after stirring the mixture for 1 hour, the mixture was successively washed with water (5 mL) and a saturated aqueous sodium chloride solution (5 mL). After the obtained organic layer was concentrated, the concentrate was washed with hexane to obtain Fmoc-Val-MeTyr(tBu)-OH (0.170 g, yield: 99%) as a white solid.

Synthetic Example 99: Synthesis of Fmoc-Val-MeVal-OH

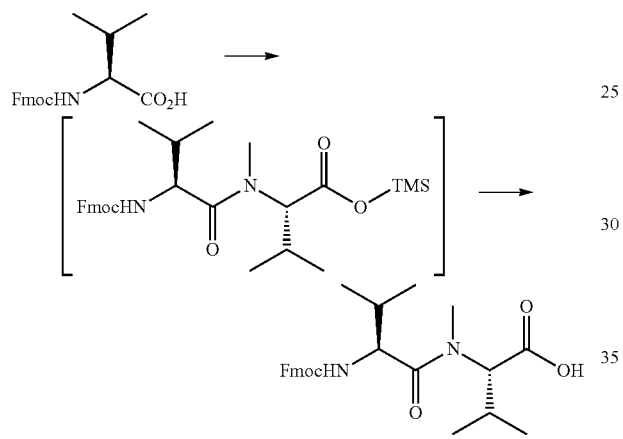

Fmoc-Val-OH (0.10 g, 0.30 mmol) was mixed with tetrahydrofuran (1.5 mL), triethylamine (0.050 mL, 0.36 mmol) and pivaloyl chloride (0.041 mL, 0.33 mmol) were added to the mixture at 0° C. and the resulting mixture was stirred for 2 hours. To the solution was added a solution which had been separately prepared by mixing H-MeVal-OH (0.047 g, 0.36 mmol), N,O-bis(trimethylsilyl)acetamide (0.19 mL, 0.72 mmol) and acetonitrile (1.5 mL) and stirring the mixture at 50° C. for 1 hour, and after the resulting mixture was further stirred at 0° C. for 1 hour, the mixture was stirred at 25° C. for 15 hours (starting material:target compound=2.4:1 (Analytical condition 3)). The obtained reaction mixture was diluted with ethyl acetate (5 mL), and successively washed with a saturated aqueous sodium hydrogen carbonate solution (5 mL), a 10 wt % aqueous citric acid solution (5 mL), water (5 mL) and a saturated aqueous sodium chloride solution (5 mL). The obtained organic layer was concentrated to obtain Fmoc-Val-MeVal-OH (0.16 g, yield: 116%) as a pale yellowish solid.

Synthetic Example 100: Synthesis of Fmoc-Val-MeVal-OH

Fmoc-Val-OH (0.068 g, 0.20 mmol) was mixed with tetrahydrofuran (1.0 mL), triethylamine (0.033 mL, 0.24 mmol) and 2-(4,4-dimethylpentan-2-yl)-5,7,7-trimethyl-octanoyl chloride (0.66 g, 0.22 mmol) were added to the mixture at 0° C. and the resulting mixture was stirred for 2 hours. To the solution was added a solution which had been separately prepared by mixing H-MeVal-OH (0.032 g, 0.24 mmol), N,O-bis(trimethylsilyl)acetamide (0.12 mL, 0.48 mmol) and acetonitrile (1.0 mL) and stirring the mixture at 50° C. for 1 hour, and after the resulting mixture was further stirred at 0° C. for 2 hours, the mixture was stirred at 25° C. for 36 hours (starting material:target compound=1:16 (Analytical condition 3)). The obtained reaction mixture was diluted with ethyl acetate (5 mL), a saturated aqueous sodium hydrogen carbonate solution (5 mL) was added thereto followed by stirring for 1 hour, and the mixture was successively washed with water (5 mL) and a saturated aqueous sodium chloride solution (5 mL). After the obtained organic layer was concentrated, the concentrate was washed with hexane to obtain Fmoc-Val-MeVal-OH (0.092 g, yield: 92%) as a white solid.

Synthetic Example 101: Synthesis of Fmoc-Val-MeSer(tBu)-OH

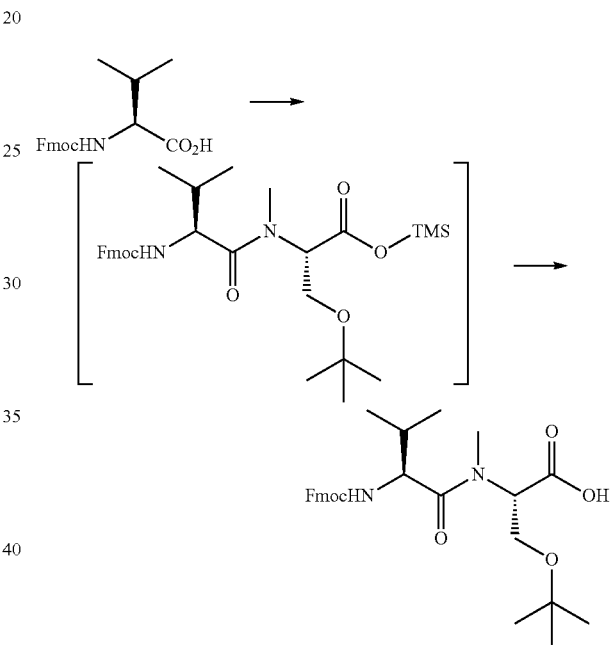

Fmoc-Val-OH (0.10 g, 0.30 mmol) was mixed with tetrahydrofuran (1.5 mL), triethylamine (0.050 mL, 0.36 mmol) and pivaloyl chloride (0.041 mL, 0.33 mmol) were added to the mixture at 0° C. and the resulting mixture was stirred for 1 hour. To the solution was added a solution which had been separately prepared by mixing H-MeSer(tBu)-OH (0.063 g, 0.36 mmol), N,O-bis(trimethylsilyl)acetamide (0.19 mL, 0.72 mmol) and acetonitrile (1.5 mL) and stirring the mixture at 50° C. for 1 hour, and the resulting mixture was further stirred at 0° C. for 15 hours. (starting material: target compound=1:19 (Analytical condition 3)). The obtained reaction mixture was diluted with ethyl acetate (5 mL), and successively washed with water (5 mL) and a saturated aqueous sodium chloride solution (5 mL). The obtained organic layer was concentrated to obtain Fmoc-Val-MeSer(tBu)-OH (0.14 g, yield: 94%) as a pale yellowish solid.

Synthetic Example 102: Synthesis of Fmoc-Val-MeSer(tBu)-OH

Fmoc-Val-OH (0.068 g, 0.20 mmol) was mixed with tetrahydrofuran (1.0 mL), triethylamine (0.033 mL, 0.24 mmol) and 2-(4,4-dimethylpentan-2-yl)-5,7,7-trimethyl-octanoyl chloride (0.66 g, 0.22 mmol) were added to the mixture at 0° C. and the resulting mixture was stirred for 2 hours. To the solution was added a solution which had been separately prepared by mixing H-MeSer(tBu)-OH (0.045 g, 0.26 mmol), N,O-bis(trimethylsilyl)acetamide (0.13 mL, 0.52 mmol) and acetonitrile (1.0 mL) and stirring the mixture at 50° C. for 1 hour, and after the resulting mixture was further stirred at 0° C. for 1 hour, the mixture was stirred at 25° C. for 15 hours (starting material:target compound=1: 25 (Analytical condition 3)). The obtained reaction mixture was diluted with ethyl acetate (5 mL), a saturated aqueous sodium hydrogen carbonate solution (5 mL) was added thereto followed by stirring for 1 hour, and the mixture was successively washed with water (5 mL) and a saturated aqueous sodium chloride solution (5 mL). After the obtained organic layer was concentrated, the concentrate was washed with hexane to obtain Fmoc-Val-MeSer(tBu)-OH (0.095 g, yield: 96%) as a white solid.

Synthetic Example 103: Synthesis of Fmoc-Val-MeDap(Boc)-OH

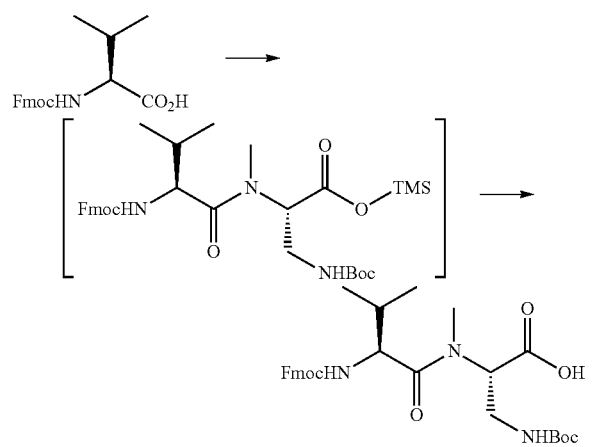

Fmoc-Val-OH (0.034 g, 0.1 mmol) was mixed with tetrahydrofuran (1.0 mL), triethylamine (0.017 mL, 0.12 mmol) and pivaloyl chloride (0.014 mL, 0.11 mmol) were added to the mixture at 0° C. and the resulting mixture was stirred for 1 hour. To the solution was added a solution which had been separately prepared by mixing Nα-Boc-Nβ-methyl-2,3-diaminopropionic acid (H-MeDap(Boc)-OH) (0.026 g, 0.12 mmol), N,O-bis(trimethylsilyl)acetamide (0.62 mL, 0.24 mmol) and acetonitrile (1.0 mL) and stirring the mixture at 50° C. for 1 hour, and after the resulting mixture was further stirred at 0° C. for 1 hour, the mixture was stirred at 25° C. for 24 hours. (starting material:target compound=1:2.4 (Analytical condition 3)).

Synthetic Example 104: Synthesis of Fmoc-Val-MeDap(Boc)-OH

Fmoc-Val-OH (0.068 g, 0.20 mmol) was mixed with tetrahydrofuran (1.0 mL), triethylamine (0.033 mL, 0.24 mmol) and 2-(4,4-dimethylpentan-2-yl)-5,7,7-trimethyl-octanoyl chloride (0.66 g, 0.22 mmol) were added to the mixture at 0° C. and the resulting mixture was stirred for 2 hours. To the solution was added a solution which had been separately prepared by mixing H-MeDap(Boc)-OH (0.052 g, 0.24 mmol), N,O-bis(trimethylsilyl)acetamide (0.12 mL, 0.48 mmol) and acetonitrile (1.0 mL) and stirring the mixture at 50° C. for 1 hour, and after the resulting mixture was further stirred at 0° C. for 1 hour, the mixture was stirred at 25° C. for 36 hours (starting material:target compound=1: 20 (Analytical condition 3)). The obtained reaction mixture was diluted with ethyl acetate (5 mL), a saturated aqueous sodium hydrogen carbonate solution (5 mL) was added thereto followed by stirring for 1 hour, and the mixture was successively washed with water (5 mL) and a saturated aqueous sodium chloride solution (5 mL). After the obtained organic layer was concentrated, the concentrate was washed with hexane to obtain Fmoc-Val-MeDap(Boc)-OH (0.107 g, yield: 99%) as a white solid.

Synthetic Example 105: Synthesis of Fmoc-Val-MeGln(Trt)-OH

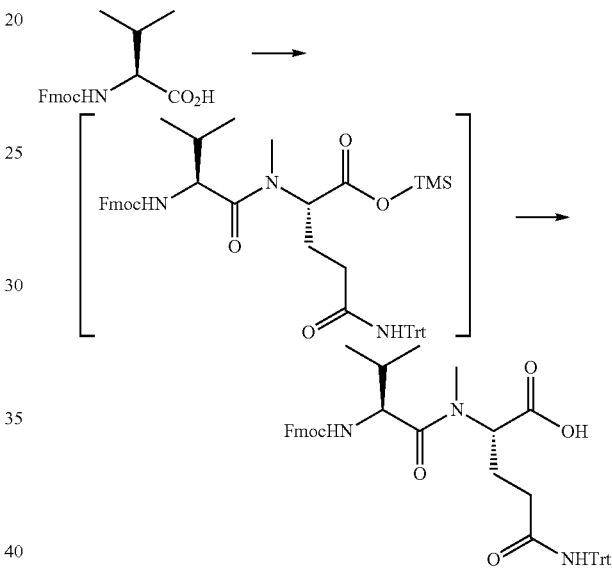

Fmoc-Val-OH (0.33 g, 0.10 mmol) was mixed with tetrahydrofuran (0.5 mL), triethylamine (0.017 mL, 0.12 mmol) and pivaloyl chloride (0.014 mL, 0.11 mmol) were added to the mixture at 0° C. and the resulting mixture was stirred for 1 hour. To the solution was added a solution which had been separately prepared by mixing H-MeGln(Trt)-OH (0.048 g, 0.12 mmol), N,O-bis(trimethylsilyl)acetamide (0.062 mL, 0.24 mmol) and acetonitrile (1.5 mL) and stirring the mixture at 50° C. for 1 hour, and after the resulting mixture was further stirred at 0° C. for 30 minutes, the mixture was stirred at 25° C. for 24 hours (starting material:target compound=1:8 (Analytical condition 3)). The obtained reaction mixture was diluted with ethyl acetate (5 mL), a saturated aqueous sodium hydrogen carbonate solution (5 mL) was added thereto followed by stirring for 1 hour, and the mixture was successively washed with water (5 mL) and a saturated aqueous sodium chloride solution (5 mL). The obtained organic layer was concentrated to obtain Fmoc-Val-MeGln(Trt)-OH (0.75 g, yield: 105%) as a pale yellowish solid.

Synthetic Example 106: Synthesis of Fmoc-Val-MeGln(Trt)-OH

Fmoc-Val-OH (0.068 g, 0.20 mmol) was mixed with tetrahydrofuran (1.0 mL), triethylamine (0.033 mL, 0.24 mmol) and 2-(4,4-dimethylpentan-2-yl)-5,7,7-trimethyl-octanoyl chloride (0.66 g, 0.22 mmol) were added to the mixture at 0° C. and the resulting mixture was stirred for 2 hours. To the solution was added a solution which had been separately prepared by mixing H-MeGln(Trt)-OH (0.097 g, 0.24 mmol), N,O-bis(trimethylsilyl)acetamide (0.12 mL, 0.48 mmol) and acetonitrile (1.0 mL) and stirring the mixture at 50° C. for 1 hour, and after the resulting mixture was further stirred at 0° C. for 1 hour, the mixture was stirred at 25° C. for 44 hours (starting material:target compound=1: 21 (Analytical condition 3)). The obtained reaction mixture was diluted with ethyl acetate (5 mL), a saturated aqueous sodium hydrogen carbonate solution (5 mL) was added thereto followed by stirring for 1 hour, and the mixture was successively washed with water (5 mL) and a saturated aqueous sodium chloride solution (5 mL). After the obtained organic layer was concentrated, the concentrate was washed with hexane to obtain Fmoc-Val-MeGln(Trt)-OH (0.151 g, yield: 104%) as a white solid.

Synthetic Example 107: Synthesis of Fmoc-Val-MeGlu(OtBu)-OH

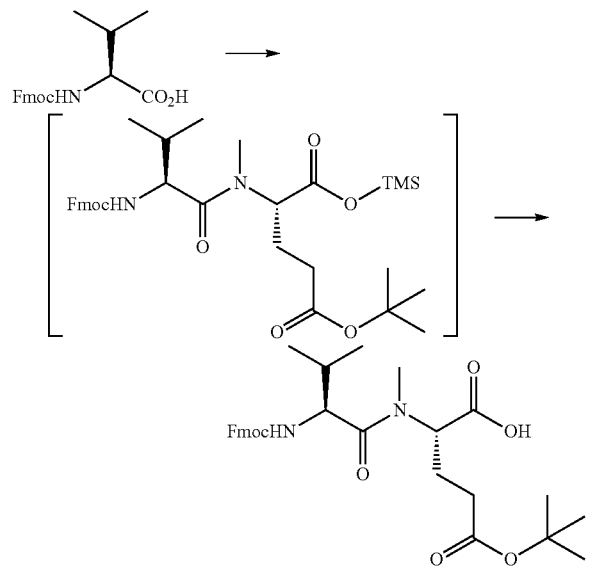

Fmoc-Val-OH (0.10 g, 0.30 mmol) was mixed with tetrahydrofuran (1.5 mL), triethylamine (0.050 mL, 0.36 mmol) and pivaloyl chloride (0.041 mL, 0.33 mmol) were added to the mixture at 0° C. and the resulting mixture was stirred for 1 hour. To the solution was added a solution which had been separately prepared by mixing H-MeGlu (OtBu)-OH (0.098 g, 0.45 mmol), N,O-bis(trimethylsilyl)acetamide (0.23 mL, 0.90 mmol) and acetonitrile (1.5 mL) and stirring the mixture at 50° C. for 1 hour, and after the resulting mixture was further stirred at 0° C. for 30 minutes, the mixture was stirred at 25° C. for 18 hours (starting material: target compound=1:18 (Analytical condition 3)). The obtained reaction mixture was diluted with ethyl acetate (5 mL), a saturated aqueous sodium hydrogen carbonate solution (5 mL) was added thereto followed by stirring for 1 hour, and the mixture was successively washed with water (5 mL) and a saturated aqueous sodium chloride solution (5 mL). The obtained organic layer was concentrated to obtain Fmoc-Val-MeGlu (OtBu)-OH (0.16 g, yield: 100%) as a pale yellowish solid.

Synthetic Example 108: Synthesis of Fmoc-Val-MeGlu (OtBu)-OH

Fmoc-Val-OH (0.068 g, 0.20 mmol) was mixed with tetrahydrofuran (1.0 mL), triethylamine (0.033 mL, 0.24 mmol) and 2-(4,4-dimethylpentan-2-yl)-5,7,7-trimethyl-octanoyl chloride (0.66 g, 0.22 mmol) were added to the mixture at 0° C. and the resulting mixture was stirred for 2 hours. To the solution was added a solution which had been separately prepared by mixing H-MeGlu (OtBu)-OH (0.078 g, 0.36 mmol), N,O-bis(trimethylsilyl)acetamide (0.185 mL, 0.72 mmol) and acetonitrile (1.5 mL) and stirring the mixture at 50° C. for 1 hour, and after the resulting mixture was further stirred at 0° C. for 1 hour, the mixture was stirred at 25° C. for 24 hours (starting material:target compound=1: 25 (Analytical condition 3)). The obtained reaction mixture was diluted with ethyl acetate (5 mL), a saturated aqueous sodium hydrogen carbonate solution (5 mL) was added thereto followed by stirring for 1 hour, and the mixture was successively washed with water (5 mL) and a saturated aqueous sodium chloride solution (5 mL). After the obtained organic layer was concentrated, the concentrate was washed with hexane to obtain Fmoc-Val-MeGlu (OtBu)-OH (0.176 g, yield: 109%) as a white solid.

Synthetic Example 109: Synthesis of Fmoc-Val-EtAla-OH

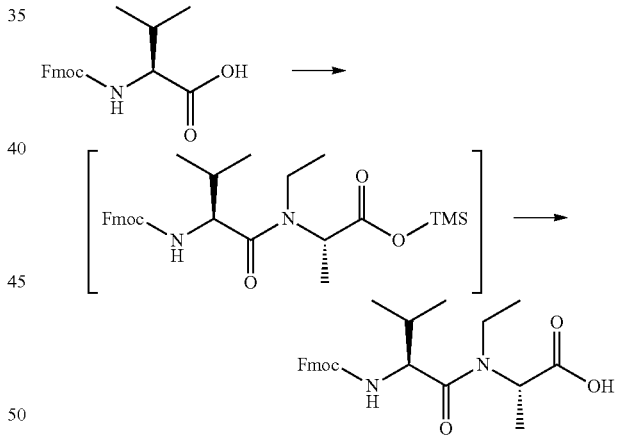

Fmoc-Val-OH (0.10 g, 0.30 mmol) was mixed with tetrahydrofuran (1.5 mL), triethylamine (0.049 mL, 0.35 mmol) and 2-(4,4-dimethylpentan-2-yl)-5,7,7-trimethyl-octanoyl chloride (0.11 g, 0.32 mmol) were added to the mixture at 0° C. and the resulting mixture was stirred for 1 hour. To the solution was added a solution which had been separately prepared by mixing H-EtAla-OH (0.041 g, 0.35 mmol), N,O-bis(trimethylsilyl)acetamide (0.17 mL, 0.71 mmol) and acetonitrile (1.5 mL) and stirring the mixture at 25° C. for 60 minutes, and the resulting mixture was further stirred at 25° C. for 22 hours (starting material:target compound=1:19 (Analytical condition 3)). The obtained reaction mixture was concentrated and diluted with acetonitrile (2.0 mL), hexane (2.0 mL) was added thereto to wash the mixture. The acetonitrile solution was diluted with ethyl acetate (6.0 mL), and successively washed with a saturated aqueous sodium hydrogen carbonate solution (4.0 mL), water (3.0 mL) and a saturated aqueous sodium chloride solution (5.0 mL). The obtained organic layer was concentrated to obtain Fmoc-Val-EtAla-OH (0.13 g, yield: 104%) as a pale yellowish solid.

Synthetic Example 110: Synthesis of Fmoc-Ala-BnAla-OH

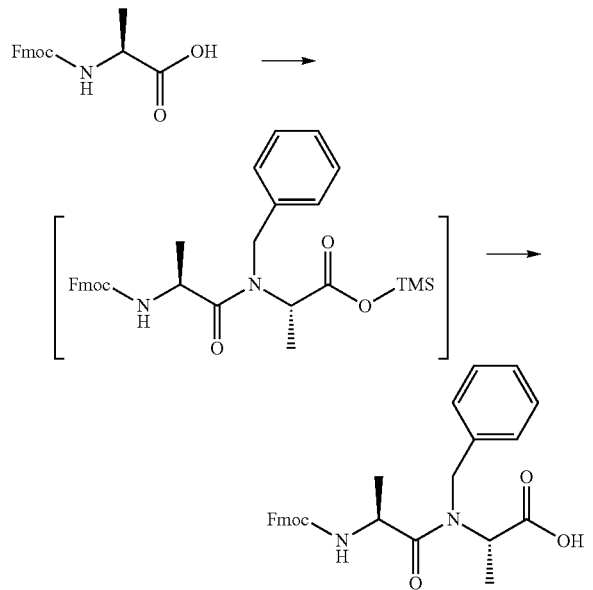

Fmoc-Ala-OH (0.10 g, 0.32 mmol) was mixed with tetrahydrofuran (1.6 mL), triethylamine (0.054 mL, 0.39 mmol) and 2-(4,4-dimethylpentan-2-yl)-5,7,7-trimethyl-octanoyl chloride (0.13 g, 0.35 mmol) were added to the mixture at 0° C. and the resulting mixture was stirred for 1 hour. To the solution was added a solution which had been separately prepared by mixing H-BnAla-OH (0.069 g, 0.39 mmol), N,O-bis(trimethylsilyl)acetamide (0.19 mL, 0.77 mmol) and acetonitrile (1.6 mL) and stirring the mixture at 25° C. for 60 minutes, and the resulting mixture was further stirred at 25° C. for 12 hours (starting material:target compound=1:1 (Analytical condition 3)). The obtained reaction mixture was concentrated and diluted with ethyl acetate (8.0 mL), and successively washed with a saturated aqueous sodium hydrogen carbonate solution (6.0 mL), water (6.0 mL) and a saturated aqueous sodium chloride solution (6.0 mL). After the obtained organic layer was concentrated, the concentrate was washed with hexane to obtain Fmoc-Ala-BnAla-OH (0.13 g, yield: 82%) as a white solid.

Synthetic Example 111: Synthesis of Fmoc-Ala-BnAla-OH

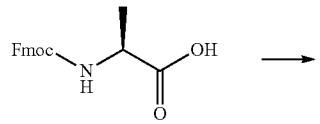

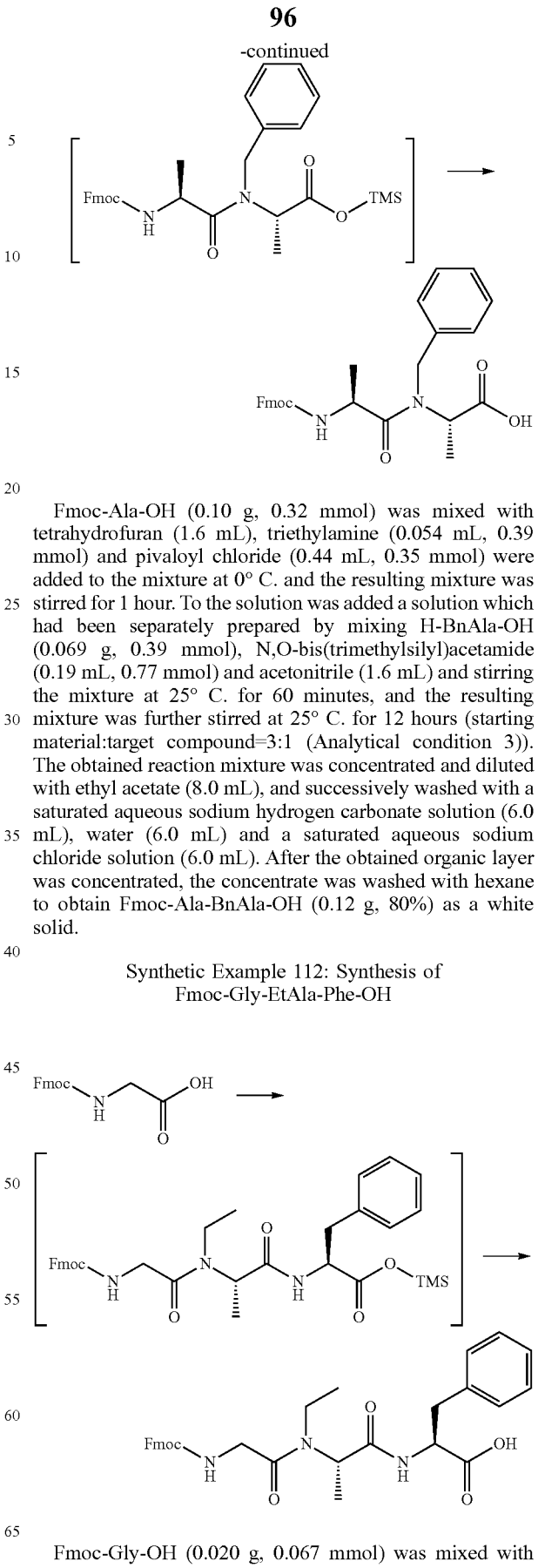

Fmoc-Ala-OH (0.10 g, 0.32 mmol) was mixed with tetrahydrofuran (1.6 mL), triethylamine (0.054 mL, 0.39 mmol) and pivaloyl chloride (0.44 mL, 0.35 mmol) were added to the mixture at 0° C. and the resulting mixture was stirred for 1 hour. To the solution was added a solution which had been separately prepared by mixing H-BnAla-OH (0.069 g, 0.39 mmol), N,O-bis(trimethylsilyl)acetamide (0.19 mL, 0.77 mmol) and acetonitrile (1.6 mL) and stirring the mixture at 25° C. for 60 minutes, and the resulting mixture was further stirred at 25° C. for 12 hours (starting material:target compound=3:1 (Analytical condition 3)). The obtained reaction mixture was concentrated and diluted with ethyl acetate (8.0 mL), and successively washed with a saturated aqueous sodium hydrogen carbonate solution (6.0 mL), water (6.0 mL) and a saturated aqueous sodium chloride solution (6.0 mL). After the obtained organic layer was concentrated, the concentrate was washed with hexane to obtain Fmoc-Ala-BnAla-OH (0.12 g, 80%) as a white solid.

Synthetic Example 112: Synthesis of Fmoc-Gly-EtAla-Phe-OH

Fmoc-Gly-OH (0.020 g, 0.067 mmol) was mixed with tetrahydrofuran (0.42 mL), triethylamine (0.011 mL, 0.080 mmol) and 2-(4,4-dimethylpentan-2-yl)-5,7,7-trimethyloctanoyl chloride (0.026 g, 0.074 mmol) were added to the mixture at 0° C. and the resulting mixture was stirred for 1 hour. To the solution was added a solution which had been separately prepared by mixing H-EtAla-Phe-OH (0.022 g, 0.080 mmol), N,O-bis(trimethylsilyl)acetamide (0.039 mL, 0.16 mmol) and acetonitrile (0.84 mL) and stirring the mixture at 25° C. for 60 minutes, and the resulting mixture was further stirred at 25° C. for 6 hours (starting material: target compound=1:33 (Analytical condition 3)). The obtained reaction mixture was diluted with ethyl acetate (5.0 mL), and successively washed with a saturated aqueous sodium hydrogen carbonate solution (5.0 mL), water (5.0 mL) and a saturated aqueous sodium chloride solution (5.0 mL). After the obtained organic layer was concentrated, the concentrate was washed with hexane to obtain Fmoc-Gly-EtAla-Phe-OH (0.040 g, yield: 109%) as a white solid.

Synthetic Example 113: Synthesis of Fmoc-Gly-EtAla-Phe-OH

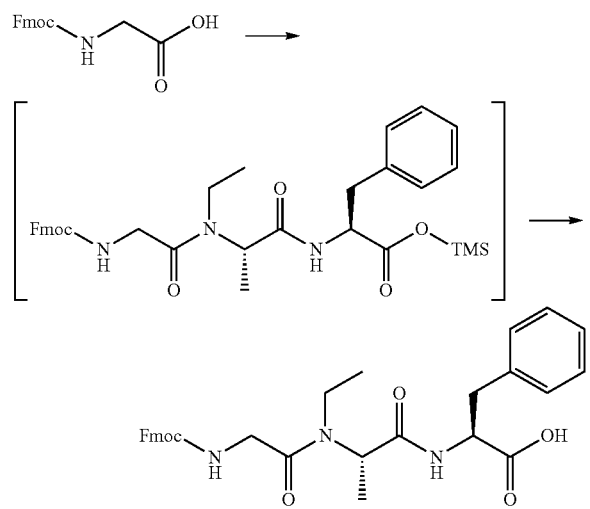

Fmoc-Gly-OH (0.025 g, 0.084 mmol) was mixed with tetrahydrofuran (0.42 mL), triethylamine (0.014 mL, 0.10 mmol) and pivaloyl chloride (0.011 mL, 0.092 mmol) were added to the mixture at 0° C. and the resulting mixture was stirred for 1 hour. To the solution was added a solution which had been separately prepared by mixing H-EtAla-Phe-OH (0.027 g, 0.10 mmol), N,O-bis(trimethylsilyl)acetamide (0.049 mL, 0.20 mmol) and acetonitrile (0.42 mL) and stirring the mixture at 25° C. for 60 minutes, and the resulting mixture was further stirred at 25° C. for 6 hours (starting material:target compound=1:9 (Analytical condition 3)). The obtained reaction mixture was diluted with ethyl acetate (5.0 mL), and successively washed with a saturated aqueous sodium hydrogen carbonate solution (5.0 mL), water (5.0 mL) and a saturated aqueous sodium chloride solution (5.0 mL). After the obtained organic layer was concentrated, the concentrate was washed with hexane to obtain Fmoc-Gly-EtAla-Phe-OH (0.050 g, yield: 109%) as a white solid.

Synthetic Example 114: Synthesis of Fmoc-Val-cHexmGly-OH

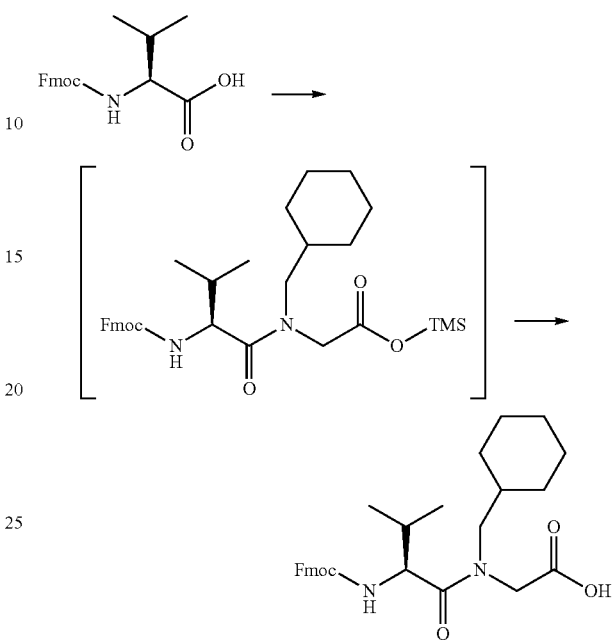

Fmoc-Val-OH (0.10 g, 0.30 mmol) was mixed with tetrahydrofuran (1.5 mL), triethylamine (0.049 mL, 0.35 mmol) and 2-(4,4-dimethylpentan-2-yl)-5,7,7-trimethyl-octanoyl chloride (0.098 g, 0.32 mmol) were added to the mixture at 0° C. and the resulting mixture was stirred for 2 hours. To the solution was added a solution which had been separately prepared by mixing N-(cyclohexylmethyl)glycine (H-cHexmGly-OH) (0.061 g, 0.35 mmol), N,O-bis(trimethylsilyl)acetamide (0.18 mL, 0.71 mmol) and acetonitrile (1.5 mL) and stirring the mixture at 50° C. for 60 minutes, and the resulting mixture was further stirred at 25° C. for 15 hours (starting material:target compound=1:32 (Analytical condition 3)). The obtained reaction mixture was concentrated and diluted with acetonitrile (6.0 mL), and hexane (11 mL) was added thereto to wash the mixture. The acetonitrile solution was diluted with ethyl acetate (10 mL), and successively washed with a saturated aqueous sodium hydrogen carbonate solution (10 mL), 1M hydrochloric acid (10 mL), water (10 mL) and a saturated aqueous sodium chloride solution (12 mL). The obtained organic layer was concentrated to obtain Fmoc-Val-cHexmGly-OH (0.15 g, yield: 104%) as a white solid.

Synthetic Example 115: Synthesis of Fmoc-Val-cHexmGly-OH

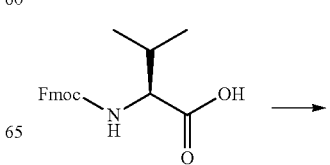

-continued

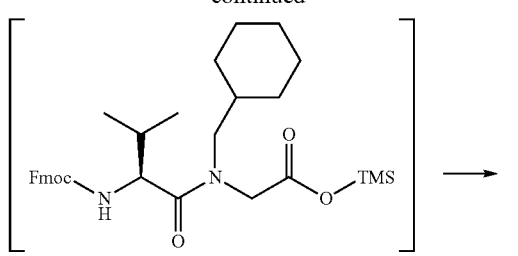

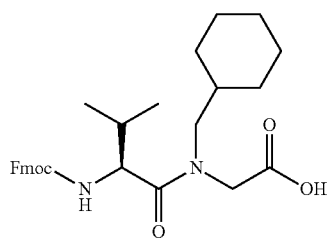

Fmoc-Val-OH (0.030 g, 0.088 mmol) was mixed with tetrahydrofuran (0.44 mL), triethylamine (0.015 mL, 0.11 mmol) and pivaloyl chloride (0.012 mL, 0.097 mmol) were added to the mixture at 0° C. and the resulting mixture was stirred for 1 hour. To the solution was added a solution which had been separately prepared by mixing H-cHexmGly-OH (0.018 g, 0.11 mmol), N,O-bis(trimethylsilyl)acetamide (0.052 mL, 0.21 mmol) and acetonitrile (0.44 mL) and stirring the mixture at 50° C. for 60 minutes, and the resulting mixture was further stirred at 0° C. for 15 hours (starting material:target compound=1:3 (Analytical condition 3)). The obtained reaction mixture was concentrated and diluted with ethyl acetate (5.0 mL), and successively washed with a saturated aqueous sodium hydrogen carbonate solution (5.0 mL), 1M hydrochloric acid (5.0 mL), water (6.0 mL) and a saturated aqueous sodium chloride solution (6.0 mL). The obtained organic layer was concentrated to obtain Fmoc-Val-cHexmGly-OH (0.048 g, yield: 109%) as a white solid.

Synthetic Example 116: Synthesis of
Fmoc-Val-Tic-OH

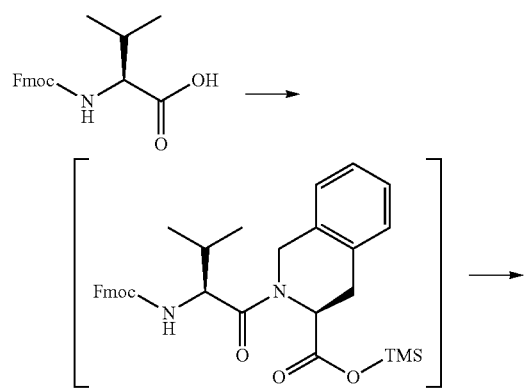

-continued

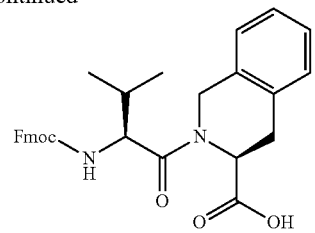

Fmoc-Val-OH (0.10 g, 0.30 mmol) was mixed with tetrahydrofuran (1.5 mL), triethylamine (0.049 mL, 0.35 mmol) and 2,2-dimethylbutanoyl chloride (0.045 mL, 0.32 mmol) were added to the mixture at 0° C. and the resulting mixture was stirred for 1 hour. To the solution was added a solution which had been separately prepared by mixing 1,2,3,4-tetrahydroisoquinoline-3-carboxylic acid (H-Tic-OH) (0.063 g, 0.35 mmol), N,O-bis(trimethylsilyl)acetamide (0.17 mL, 0.71 mmol) and acetonitrile (1.5 mL) and stirring the mixture at 25° C. for 60 minutes, and the resulting mixture was further stirred at 0° C. for 4 hours (starting material:target compound=1:99 (Analytical condition 3)). The obtained reaction mixture was diluted with ethyl acetate (10 mL), and successively washed with a saturated aqueous sodium hydrogen carbonate solution (8.0 mL), a 10 wt % aqueous citric acid solution (8.0 mL), water (10 mL) and a saturated aqueous sodium chloride solution (10 mL). The collected organic layer was concentrated to obtain Fmoc-Val-Tic-OH (0.15 g, yield: 100%) as a white solid.

Synthetic Example 117: Synthesis of
Fmoc-Val-Tic-OH

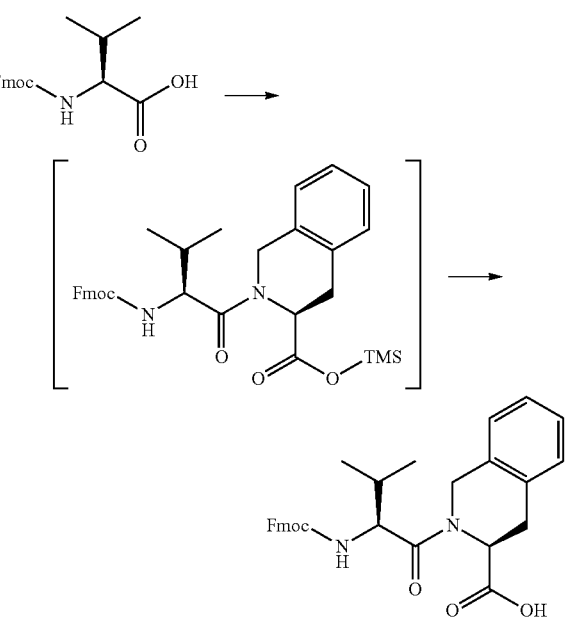

Fmoc-Val-OH (0.10 g, 0.30 mmol) was mixed with tetrahydrofuran (1.5 mL), triethylamine (0.049 mL, 0.35 mmol) and pivaloyl chloride (0.040 mL, 0.32 mmol) were added to the mixture at 0° C. and the resulting mixture was stirred for 1 hour. To the solution was added a solution which had been separately prepared by mixing H-Tic-OH (0.063 g, 0.35 mmol), N,O-bis(trimethylsilyl)acetamide (0.17 mL, 0.71 mmol) and acetonitrile (1.5 mL) and stirring the mixture at 25° C. for 60 minutes, and the resulting mixture was further stirred at 0° C. for 4 hours (starting material: target compound=1:32 (Analytical condition 3)). The obtained reaction mixture was diluted with ethyl acetate (10 mL), and successively washed with a saturated aqueous sodium hydrogen carbonate solution (8.0 mL), 10 wt % aqueous citric acid solution (8.0 mL), water (10 mL) and a saturated aqueous sodium chloride solution (10 mL). The collected organic layer was concentrated to obtain Fmoc-Val-Tic-OH (0.14 g, yield: 97%) as a white solid.

Synthetic Example 118: Synthesis of 2-(4,4-dimethylpentan-2-yl)-5,7,7-trimethyloctanoyl bromide

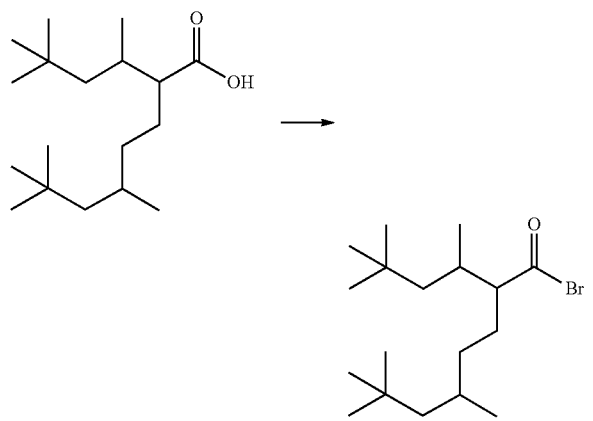

2-(4,4-dimethylpentan-2-yl)-5,7,7-trimethyloctanoic acid (3.0 g, 10.6 mmol) and phosphorus tribromide (0.94 g, 3.48 mmol) were mixed, and the mixture was stirred at 50° C. for 24 hours. The obtained mixture was diluted with hexane (30 mL), and washed with water (20 mL). The organic layer was concentrated to obtain 2-(4,4-dimethylpentan-2-yl)-5,7,7-trimethyloctanoyl bromide (3.7 g, 10.6 mmol) as a colorless liquid.

Synthetic Example 119: Synthesis of Fmoc-Val-MeGlu (OtBu)-OH

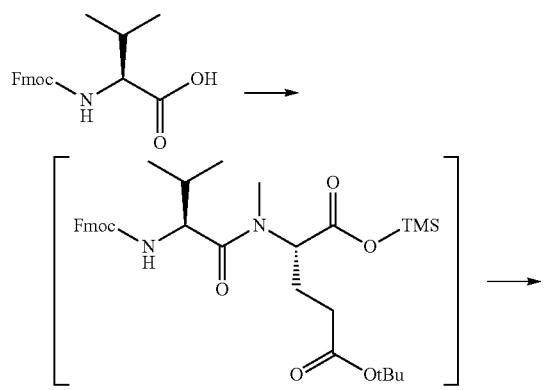

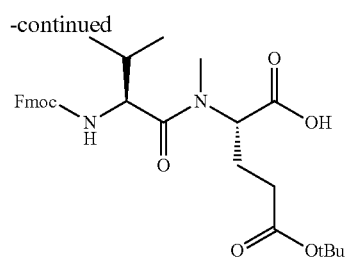

Fmoc-Val-OH (0.10 g, 0.30 mmol) was mixed with tetrahydrofuran (1.5 mL), triethylamine (0.049 mL, 0.35 mmol) and 2-(4,4-dimethylpentan-2-yl)-5,7,7-trimethyl-octanoyl bromide (0.13 g, 0.32 mmol) were added to the mixture at 0° C. and the resulting mixture was stirred for 1 hour. To the solution was added a solution which had been separately prepared by mixing H-MeGlu(OtBu)-OH (0.077 g, 0.35 mmol), N,O-bis(trimethylsilyl)acetamide (0.17 mL, 0.71 mmol) and acetonitrile (1.5 mL) and stirring the mixture at 50° C. for 60 minutes, and the resulting mixture was further stirred at 25° C. for 20 hours (starting material: target compound=<1:99 (Analytical condition 3)). The obtained reaction mixture was concentrated and diluted with acetonitrile (8.0 mL), and hexane (8.0 mL) was added thereto to wash the mixture twice. The acetonitrile solution was diluted with ethyl acetate (8.0 mL), and successively washed with a saturated aqueous sodium hydrogen carbonate solution (7.0 mL), 1M hydrochloric acid (7.0 mL), water (10 mL) and a saturated aqueous sodium chloride solution (10 mL). The obtained organic layer was concentrated to obtain Fmoc-Val-MeGlu(OtBu)-OH (0.16 g, yield: 98%) as a white solid.

Synthetic Example 120: Synthesis of Fmoc-Val-(Me)βAla-OH

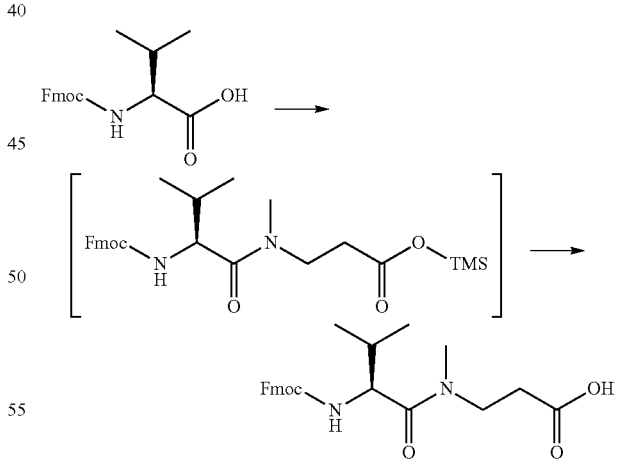

Fmoc-Val-OH (0.10 g, 0.30 mmol) was mixed with tetrahydrofuran (1.5 mL), triethylamine (0.058 mL, 0.41 mmol) and 2-(4,4-dimethylpentan-2-yl)-5,7,7-trimethyl-octanoyl chloride (0.12 g, 0.38 mmol) were added to the mixture at 0° C. and the resulting mixture was stirred for 2 hours. To the solution was added a solution which had been separately prepared by mixing H-(Me)βAla-OH hydrochloride (0.058 g, 0.41 mmol), N,O-bis(trimethylsilyl)acetamide (0.40 mL, 1.6 mmol) and acetonitrile (1.5 mL) and stirring the mixture at 25° C. for 60 minutes, and the resulting mixture was further stirred at 0° C. for 7 hours (starting material:target compound=1:24 (Analytical condition 3)). The obtained reaction mixture was diluted with ethyl acetate (4.0 mL), a saturated aqueous sodium hydrogen carbonate solution (4.0 mL) was added thereto and the resulting mixture was stirred at 25° C. for 1 hour. The obtained organic layer was successively washed with a 10 wt % aqueous citric acid solution (4.0 mL), water (3.0 mL) and a saturated aqueous sodium chloride solution (3.0 mL). The collected organic layer was concentrated, and the concentrate was washed with hexane to obtain Fmoc-Val-(Me)βAla-OH (0.125 g, yield: 94%) as a white solid.

Synthetic Example 121: Synthesis of Fmoc-Val-(Me)βAla-OH

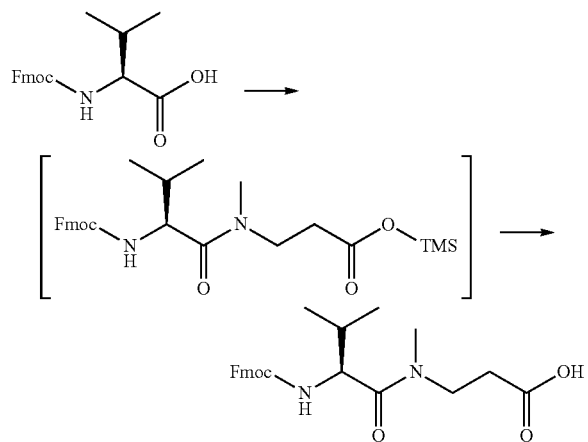

Fmoc-Val-OH (0.10 g, 0.30 mmol) was mixed with tetrahydrofuran (1.5 mL), triethylamine (0.049 mL, 0.35 mmol) and pivaloyl chloride (0.040 mL, 0.32 mmol) were added to the mixture at 0° C. and the resulting mixture was stirred for 1 hour. To the solution was added a solution which had been separately prepared by mixing H-(Me)βAla-OH hydrochloride (0.049 g, 0.35 mmol), N,O-bis(trimethylsilyl) acetamide (0.35 mL, 1.4 mmol) and acetonitrile (1.4 mL) and stirring the mixture at 25° C. for 60 minutes, and after the resulting mixture was further stirred at 0° C. for 1 hour, the mixture was stirred at 25° C. for 1 hour (starting material:target compound=1:1 (Analytical condition 3)). The obtained reaction mixture was diluted with ethyl acetate (3.0 mL), a saturated aqueous sodium hydrogen carbonate solution (4.0 mL) was added thereto and the resulting mixture was stirred at 25° C. for 1 hour. The obtained organic layer was successively washed with a 10 wt % aqueous citric acid solution (4.0 mL), water (3.0 mL) and a saturated aqueous sodium chloride solution (3.0 mL). The collected organic layer was concentrated, and the concentrate was washed with hexane to obtain Fmoc-Val-(Me)βAla-OH (0.13 g, yield: 102%) as a white solid.

Synthetic Example 122: Synthesis of Fmoc-Val-MeGABA-OH

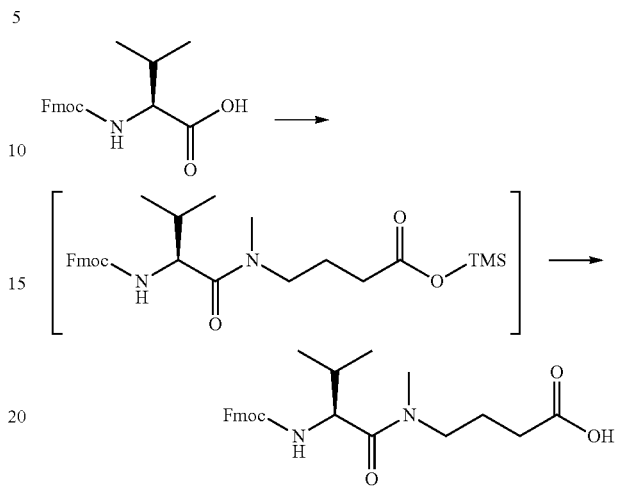

Fmoc-Val-OH (0.10 g, 0.30 mmol) was mixed with tetrahydrofuran (1.5 mL), triethylamine (0.058 mL, 0.41 mmol) and 2-(4,4-dimethylpentan-2-yl)-5,7,7-trimethyl-octanoyl chloride (0.12 mL, 0.38 mmol) were added to the mixture at 0° C. and the resulting mixture was stirred for 2 hours. To the solution was added a solution which had been separately prepared by mixing H-MeGABA-OH hydrochloride (0.063 g, 0.41 mmol), N,O-bis(trimethylsilyl)acetamide (0.38 mL, 1.5 mmol) and acetonitrile (1.5 mL) and stirring the mixture at 25° C. for 60 minutes, and after the resulting mixture was further stirred at 0° C. for 7 hours, the mixture was stirred at 10° C. for 12 hours (starting material:target compound=1:19 (Analytical condition 3)). The obtained reaction mixture was diluted with ethyl acetate (4.0 mL), a saturated aqueous sodium hydrogen carbonate solution (4.0 mL) was added thereto and the mixture was stirred at 25° C. for 1 hour. The obtained organic layer was successively washed with a 10 wt % aqueous citric acid solution (4.0 mL), water (3.0 mL) and a saturated aqueous sodium chloride solution (3.0 mL). The collected organic layer was concentrated, and the concentrate was washed with hexane to obtain Fmoc-Val-MeGABA-OH (0.135 g, yield: 104%) as a white solid.

Synthetic Example 123: Synthesis of Fmoc-Val-MeGABA-OH

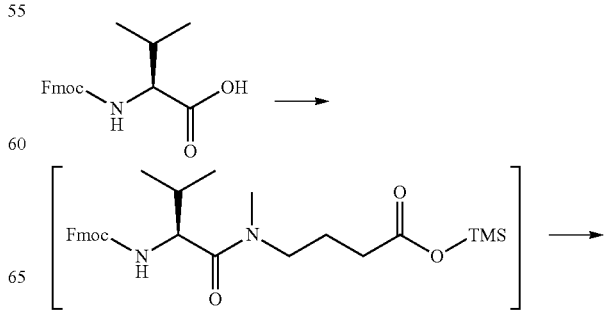

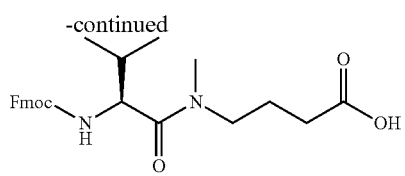

Fmoc-Val-OH (0.10 g, 0.30 mmol) was mixed with tetrahydrofuran (1.5 mL), triethylamine (0.049 mL, 0.35 mmol) and pivaloyl chloride (0.040 mL, 0.32 mmol) were added to the mixture at 0° C. and the resulting mixture was stirred for 1 hour. To the solution was added a solution which had been separately prepared by mixing H-MeGABA-OH hydrochloride (0.054 g, 0.35 mmol), N,O-bis(trimethylsilyl)acetamide (0.35 mL, 1.4 mmol) and acetonitrile (1.5 mL) and stirring the mixture at 25° C. for 60 minutes, and after the resulting mixture was further stirred at 0° C. for 1 hour, the mixture was stirred at 25° C. for 1 hour (starting material:target compound=1:4 (Analytical condition 3)). The obtained reaction mixture was diluted with ethyl acetate (4.0 mL), a saturated aqueous sodium hydrogen carbonate solution (4.0 mL) was added thereto and the mixture was stirred at 25° C. for 1 hour. The obtained organic layer was successively washed with a 10 wt % aqueous citric acid solution (4.0 mL), water (3.0 mL) and a saturated aqueous sodium chloride solution (3.0 mL). The collected organic layer was concentrated, and the concentrate was washed with hexane to obtain Fmoc-Val-MeGABA-OH (0.125 g, yield: 97%) as a white solid.

Synthetic Example 124: Synthesis of Fmoc-Val-(Me)βAla-MePhe-OH

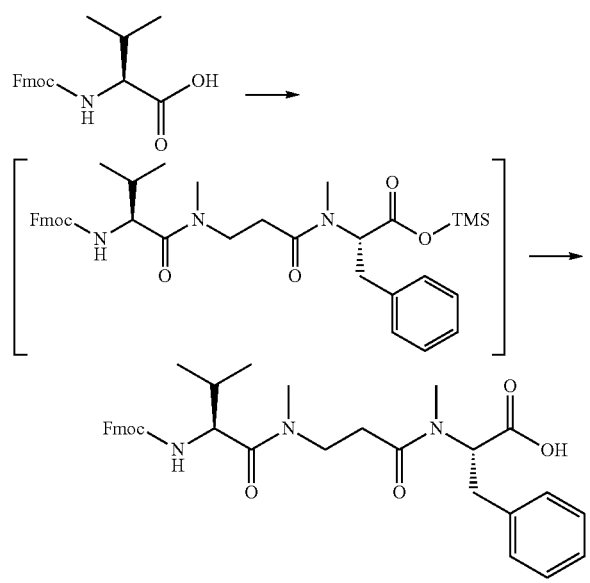

Fmoc-Val-OH (0.100 g, 0.30 mmol) was mixed with tetrahydrofuran (1.5 mL), triethylamine (0.049 mL, 0.35 mmol) and 2-(4,4-dimethylpentan-2-yl)-5,7,7-trimethyl-octanoyl chloride (0.12 g, 0.32 mmol) were added to the mixture at 0° C. and the resulting mixture was stirred for 1 hour. To the solution was added a solution which had been separately prepared by mixing H-(Me)βAla-MePhe-OH (0.093 g, 0.35 mmol), N,O-bis(trimethylsilyl)acetamide (0.17 mL, 0.71 mmol) and acetonitrile (1.5 mL) and stirring the mixture at 25° C. for 60 minutes, and the resulting mixture was stirred at 0° C. for 2 hours (starting material: target compound=1:48 (Analytical condition 3)). The obtained reaction mixture was diluted with ethyl acetate (4.0 mL), and successively washed with a saturated aqueous sodium hydrogen carbonate solution (4.0 mL), water (3.0 mL) and a saturated aqueous sodium chloride solution (3.0 mL). After the obtained organic layer was concentrated, the concentrate was washed with hexane to obtain Fmoc-Val-(Me)βAla-MePhe-OH (0.18 g, yield: 107%) as a white solid.

Synthetic Example 125: Synthesis of Fmoc-Val-(Me)βAla-MePhe-OH

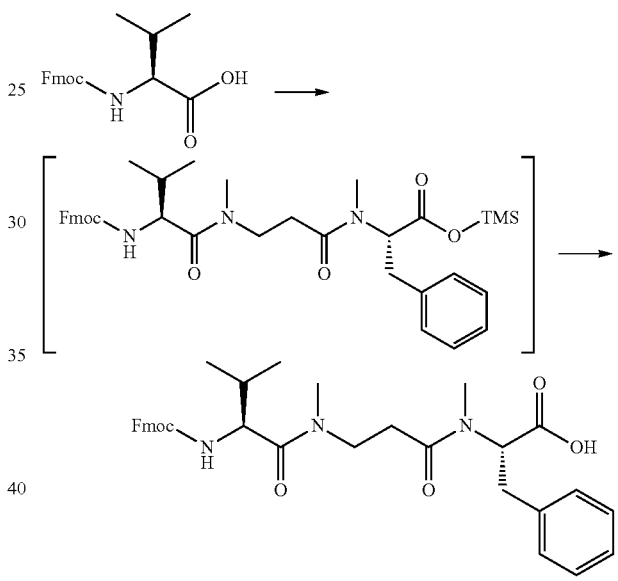

Fmoc-Val-OH (0.100 g, 0.30 mmol) was mixed with tetrahydrofuran (1.5 mL), triethylamine (0.049 mL, 0.35 mmol) and pivaloyl chloride (0.040 mL, 0.32 mmol) were added to the mixture at 0° C. and the resulting mixture was stirred for 1 hour. To the solution was added a solution which had been separately prepared by mixing H-(Me)βAla-MePhe-OH (0.093 g, 0.35 mmol), N,O-bis(trimethylsilyl)acetamide (0.17 mL, 0.71 mmol) and acetonitrile (1.5 mL) and stirring the mixture at 25° C. for 60 minutes, and the mixture was stirred at 0° C. for 2 hours (starting material: target compound=1:24 (Analytical condition 3)). The obtained reaction mixture was diluted with ethyl acetate (4.0 mL), and successively washed with a saturated aqueous sodium hydrogen carbonate solution (4.0 mL), water (3.0 mL) and a saturated aqueous sodium chloride solution (3.0 mL). After the obtained organic layer was concentrated, the concentrate was washed with hexane to obtain Fmoc-Val-(Me)βAla-MePhe-OH (0.19 g, yield: 109%) as a white solid.

Synthetic Example 126: Synthesis of Fmoc-Val-MeGABA-MePhe-OH

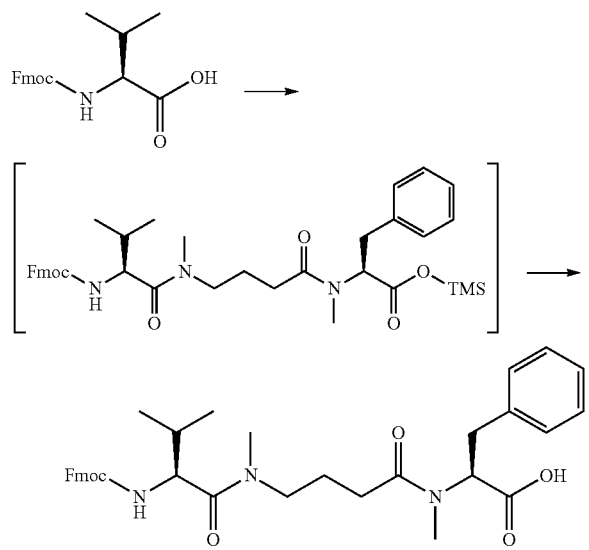

Fmoc-Val-OH (0.100 g, 0.30 mmol) was mixed with tetrahydrofuran (1.5 mL), triethylamine (0.049 mL, 0.35 mmol) and 2-(4,4-dimethylpentan-2-yl)-5,7,7-trimethyl-octanoyl chloride (0.12 g, 0.32 mmol) were added to the mixture at 0° C. and the resulting mixture was stirred for 1 hour. To the solution was added a solution which had been separately prepared by mixing H-MeGABA-MePhe-OH (0.098 g, 0.35 mmol), N,O-bis(trimethylsilyl)acetamide (0.17 mL, 0.71 mmol) and acetonitrile (1.5 mL) and stirring the mixture at 25° C. for 60 minutes, and the mixture was stirred at 0° C. for 2 hours (starting material:target compound=1:16 (Analytical condition 3)). The obtained reaction mixture was diluted with ethyl acetate (4.0 mL), and successively washed with a saturated aqueous sodium hydrogen carbonate solution (4.0 mL), water (3.0 mL) and a saturated aqueous sodium chloride solution (3.0 mL). After the obtained organic layer was concentrated, the concentrate was washed with hexane to obtain Fmoc-Val-MeGABA-MePhe-OH (0.18 g, yield: 107%) as a white solid.

Synthetic Example 127: Synthesis of Fmoc-Val-MeGABA-MePhe-OH

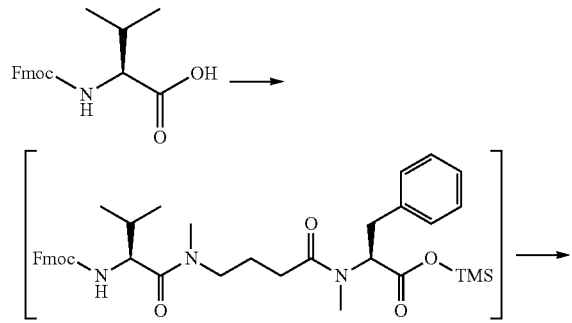

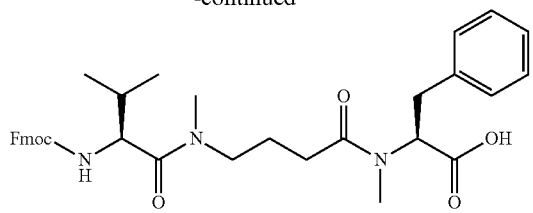

Fmoc-Val-OH (0.100 g, 0.30 mmol) was mixed with tetrahydrofuran (1.5 mL), triethylamine (0.049 mL, 0.35 mmol) and pivaloyl chloride (0.040 mL, 0.32 mmol) were added to the mixture at 0° C. and the resulting mixture was stirred for 1 hour. To the solution was added a solution which had been separately prepared by mixing H-MeGABA-MePhe-OH (0.098 g, 0.35 mmol), N,O-bis(trimethylsilyl)acetamide (0.17 mL, 0.71 mmol) and acetonitrile (1.5 mL) and stirring the mixture at 25° C. for 60 minutes, and the mixture was stirred at 0° C. for 2 hours (starting material:target compound=1:3 (Analytical condition 3)). The obtained reaction mixture was diluted with ethyl acetate (4.0 mL), and successively washed with a saturated aqueous sodium hydrogen carbonate solution (4.0 mL), water (3.0 mL) and a saturated aqueous sodium chloride solution (3.0 mL). After the obtained organic layer was concentrated, the concentrate was washed with hexane to obtain Fmoc-Val-MeGABA-MePhe-OH (0.19 g, yield: 108%) as a white solid.

Synthetic Example 128: Synthesis of Fmoc-Val-(Me)βhomoTrp(1-Me)-OH

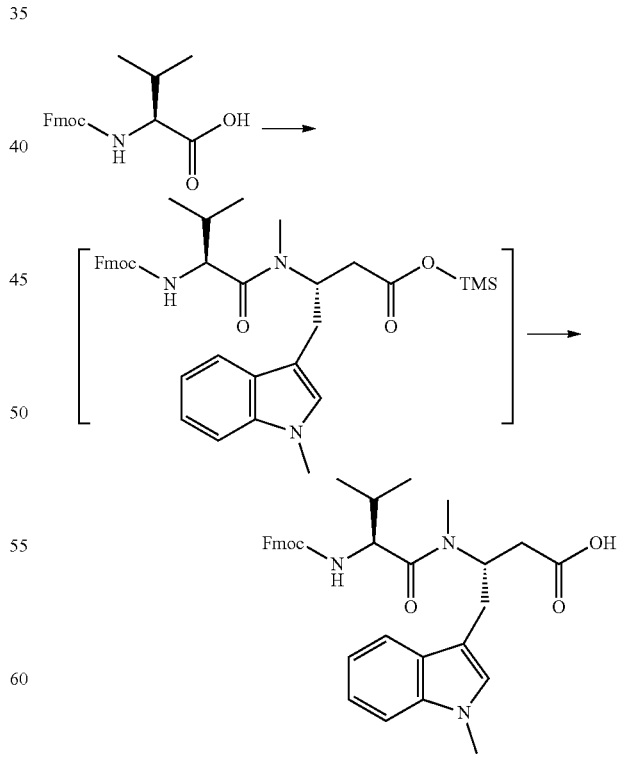

Fmoc-Val-OH (0.030 g, 0.11 mmol) was mixed with tetrahydrofuran (0.44 mL), triethylamine (0.015 mL, 0.11 mmol) and 2-(4,4-dimethylpentan-2-yl)-5,7,7-trimethyloctanoyl chloride (0.035 g, 0.097 mmol) were added to the mixture at 0° C. and the resulting mixture was stirred for 2 hours. To the solution was added a solution which had been separately prepared by mixing H-(Me)βhomoTrp(1-Me)-OH hydrochloride (0.030 g, 0.11 mmol), N,O-bis(trimethylsilyl)acetamide (0.10 mL, 0.42 mmol) and acetonitrile (0.44 mL) and stirring the mixture at 25° C. for 60 minutes, and the mixture was stirred at 25° C. for 15 hours (starting material:target compound=1:24 (Analytical condition 3)). The obtained reaction mixture was diluted with ethyl acetate (4.0 mL), and successively washed with a saturated aqueous sodium hydrogen carbonate solution (4.0 mL), water (3.0 mL) and a saturated aqueous sodium chloride solution (3.0 mL). After the obtained organic layer was concentrated, the concentrate was washed with hexane to obtain Fmoc-Val-(Me)βhomoTrp(1-Me)-OH (0.056 g, yield: 111%) as a white solid.

Synthetic Example 129: Synthesis of Fmoc-Val-(Me)βhomoTrp(1-Me)-OH

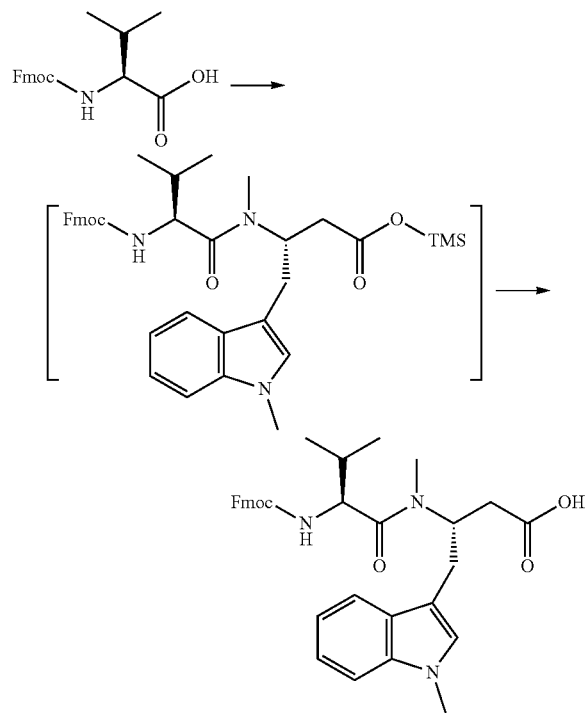

Fmoc-Val-OH (0.070 g, 0.21 mmol) was mixed with tetrahydrofuran (1.0 mL), triethylamine (0.035 mL, 0.11 mmol) and pivaloyl chloride (0.028 mL, 0.23 mmol) were added to the mixture at 0° C. and the resulting mixture was stirred for 1 hour. To the solution was added a solution which had been separately prepared by mixing H-(Me)βhomoTrp(1-Me)-OH hydrochloride (0.070 g, 0.25 mmol), N,O-bis(trimethyl-silyl)acetamide (0.24 mL, 0.99 mmol) and acetonitrile (1.0 mL) and stirring the mixture at 25° C. for 60 minutes, and after the resulting mixture was stirred at 0° C. for 15 hours, the mixture was further stirred at 25° C. for 4 hours (starting material:target compound=1:8 (Analytical condition 3)). The obtained reaction mixture was diluted with ethyl acetate (4.0 mL), a saturated aqueous sodium hydrogen carbonate solution (4.0 mL) was added thereto and the mixture was stirred at 25° C. for 1 hour. The obtained organic layer was successively washed with a 10 wt % aqueous citric acid solution (4.0 mL), water (3.0 mL) and a saturated aqueous sodium chloride solution (3.0 mL). The collected organic layer was concentrated, and the concentrate was washed with hexane to obtain Fmoc-Val-(Me)βhomoTrp(1-Me)-OH (0.090 g, yield: 77%) as a white solid.

Synthetic Example 130: Synthesis of Fmoc-Val-βhomoTrp(1-Me)-OH

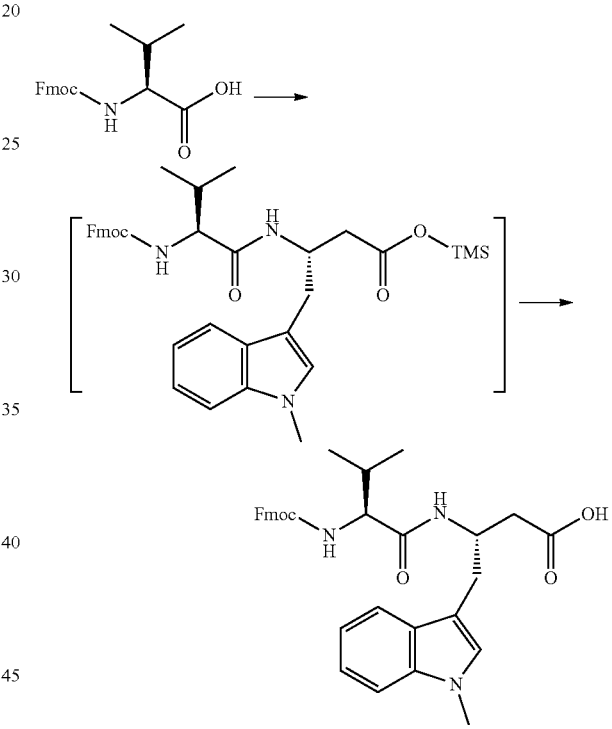

Fmoc-Val-OH (0.050 g, 0.15 mmol) was mixed with tetrahydrofuran (0.74 mL), triethylamine (0.025 mL, 0.18 mmol) and 2-(4,4-dimethylpentan-2-yl)-5,7,7-trimethyloctanoyl chloride (0.049 g, 0.16 mmol) were added to the mixture at 0° C. and the resulting mixture was stirred for 1 hour. To the solution was added a solution which had been separately prepared by mixing H-βhomoTrp (1-Me)-OH hydrochloride (0.048 g, 0.18 mmol), N,O-bis(trimethylsilyl)acetamide (0.17 mL, 0.71 mmol) and acetonitrile (0.74 mL) and stirring the mixture at 50° C. for 60 minutes, and the resulting mixture was stirred at 25° C. for 15 hours (starting material:target compound=1:99 (Analytical condition 3)). The obtained reaction mixture was diluted with ethyl acetate (4.0 mL), and successively washed with a saturated aqueous sodium hydrogen carbonate solution (4.0 mL), water (3.0 mL) and a saturated aqueous sodium chloride solution (3.0 mL). After the obtained organic layer was concentrated, the concentrate was washed with hexane to obtain Fmoc-Val-βhomoTrp(1-Me)-OH (0.11 g, yield: 130%) as a white solid.

Synthetic Example 131: Synthesis of Fmoc-Val-βhomoTrp(1-Me)-OH

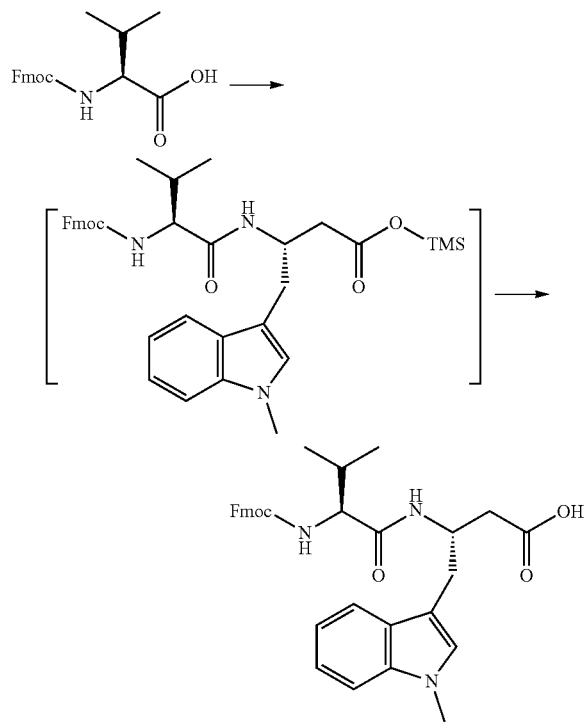

Fmoc-Val-OH (0.050 g, 0.15 mmol) was mixed with tetrahydrofuran (0.74 mL), triethylamine (0.025 mL, 0.18 mmol) and pivaloyl chloride (0.020 g, 0.16 mmol) were added to the mixture at 0° C. and the resulting mixture was stirred for 1 hour. To the solution was added a solution which had been separately prepared by mixing H-βhomoTrp(1-Me)-OH hydrochloride (0.048 g, 0.18 mmol), N,O-bis(trimethylsilyl)-acetamide (0.17 mL, 0.71 mmol) and acetonitrile (0.74 mL) and stirring the mixture at 50° C. for 60 minutes, and the resulting mixture was stirred at 25° C. for 15 hours (starting material:target compound=1:19 (Analytical condition 3)). The obtained reaction mixture was diluted with ethyl acetate (4.0 mL), and successively washed with a saturated aqueous sodium hydrogen carbonate solution (4.0 mL), water (3.0 mL) and a saturated aqueous sodium chloride solution (3.0 mL). After the obtained organic layer was concentrated, the concentrate was washed with hexane to obtain Fmoc-Val-βhomoTrp(1-Me)-OH (0.079 g, yield: 97%) as a white solid.

Synthetic Example 132: Synthesis of Fmoc-Val-(Me)βhomoLeu-OH

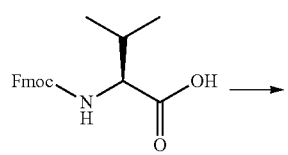

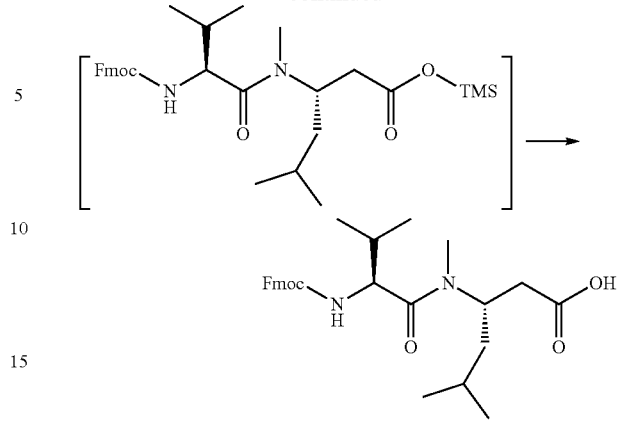

Fmoc-Val-OH (0.030 g, 0.088 mmol) was mixed with tetrahydrofuran (0.44 mL), triethylamine (0.015 mL, 0.11 mmol) and 2-(4,4-dimethylpentan-2-yl)-5,7,7-trimethyloctanoyl chloride (0.035 g, 0.097 mmol) were added to the mixture at 0° C. and the resulting mixture was stirred for 2 hours. To the solution was added a solution which had been separately prepared by mixing H-(Me)βhomoLeu-OH hydrochloride (0.021 g, 0.11 mmol), N,O-bis(trimethylsilyl) acetamide (0.10 mL, 0.42 mmol) and acetonitrile (0.44 mL) and stirring the mixture at 25° C. for 60 minutes, and the resulting mixture was further stirred at 25° C. for 15 hours (starting material:target compound=1:24 (Analytical condition 3)). The obtained reaction mixture was diluted with ethyl acetate (4.0 mL), and successively washed with a saturated aqueous sodium hydrogen carbonate solution (4.0 mL), water (3.0 mL) and a saturated aqueous sodium chloride solution (3.0 mL). After the obtained organic layer was concentrated, the concentrate was washed with hexane and a mixed solution of 10% isopropyl ether/hexane to obtain Fmoc-Val-(Me)βhomoLeu-OH (0.045 g, yield: 106%) as a white solid.

Synthetic Example 133: Synthesis of Fmoc-Val-(Me)βhomoLeu-OH

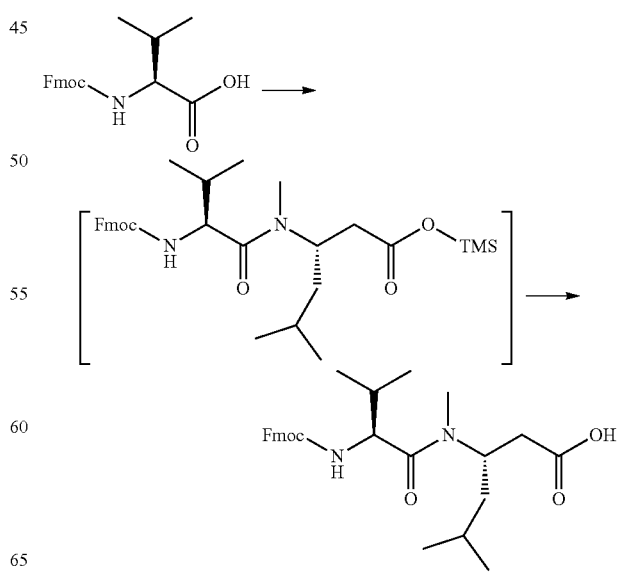

Fmoc-Val-OH (0.070 g, 0.21 mmol) was mixed with tetrahydrofuran (1.0 mL), triethylamine (0.035 mL, 0.25 mmol) and pivaloyl chloride (0.028 mL, 0.23 mmol) were added to the mixture at 0° C. and the resulting mixture was stirred for 1 hour. To the solution was added a solution which had been separately prepared by mixing H-(Me)βhomoLeu-OH hydrochloride (0.048 g, 0.25 mmol), N,O-bis(trimethylsilyl)-acetamide (0.24 mL, 0.99 mmol) and acetonitrile (1.0 mL) and stirring the mixture at 25° C. for 60 minutes, and after the resulting mixture was stirred at 0° C. for 15 hours, the mixture was further stirred at 25° C. for 2 hours (starting material:target compound=1:5 (Analytical condition 3)). The obtained reaction mixture was diluted with ethyl acetate (4.0 mL), a saturated aqueous sodium hydrogen carbonate solution (4.0 mL) and water (3.0 mL) were added thereto, and the resulting mixture was stirred at 25° C. for 1 hour. The obtained organic layer was successively washed with a 10 wt % aqueous citric acid solution (4 mL), water (3.0 mL) and a saturated aqueous sodium chloride solution (3.0 mL). The collected organic layer was concentrated, and the concentrate was washed with hexane to obtain Fmoc-Val-(Me)βhomoLeu-OH (0.095 g, yield: 96%) as a white solid.

Synthetic Example 134: Synthesis of Fmoc-(Me)βAla-MePhe-OH

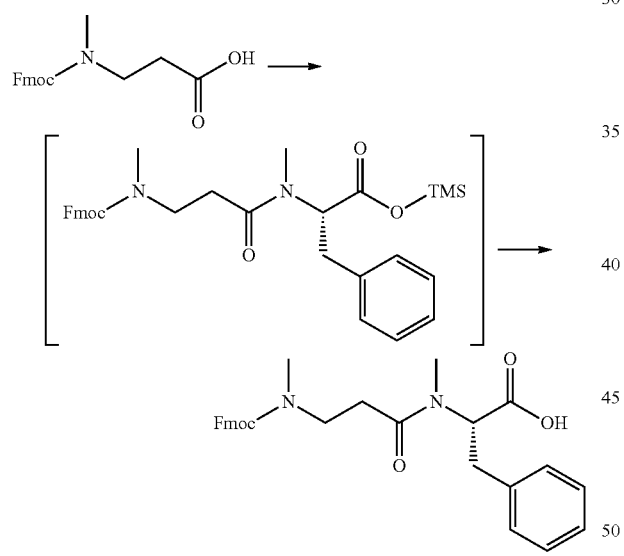

Fmoc-(Me)βAla-OH (1.0 g, 3.1 mmol) was mixed with tetrahydrofuran (15 mL), triethylamine (0.51 mL, 3.7 mmol) and 2-(4,4-dimethylpentan-2-yl)-5,7,7-trimethyloctanoyl chloride (1.2 g, 3.4 mmol) were added to the mixture at 0° C. and the resulting mixture was stirred for 1 hour. To the solution was added a solution which had been separately prepared by mixing H-MePhe-OH (0.66 g, 3.7 mmol), N,O-bis(trimethylsilyl)acetamide (1.8 mL, 7.4 mmol) and acetonitrile (15 mL) and stirring the mixture at 25° C. for 60 minutes, and the resulting mixture was further stirred at 0° C. for 3 hours (starting material:target compound=1:48 (Analytical condition 3)). The obtained reaction mixture was diluted with ethyl acetate (40 mL), and successively washed with water (15 mL) and a saturated aqueous sodium chloride solution (15 mL). The collected organic layer was concentrated, and the concentrate was purified by column chromatography to obtain Fmoc-(Me)βAla-MePhe-OH (1.3 g, yield: 85%) as a white solid.

Synthetic Example 135: Synthesis of Fmoc-(Me)βAla-MePhe-OH

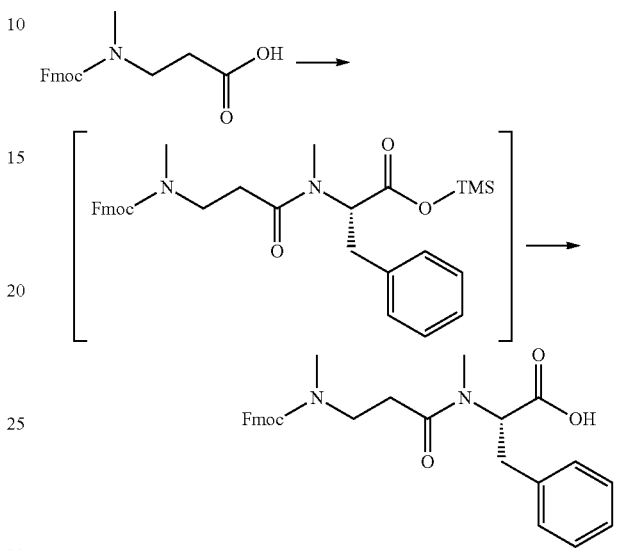

Fmoc-(Me)βAla-OH (0.10 g, 0.31 mmol) was mixed with tetrahydrofuran (1.5 mL), triethylamine (0.051 mL, 0.37 mmol) and pivaloyl chloride (0.041 mL, 0.34 mmol) were added to the mixture at 0° C. and the resulting mixture was stirred for 1 hour. To the solution was added a solution which had been separately prepared by mixing H-MePhe-OH (0.066 g, 0.37 mmol), N,O-bis(trimethylsilyl)acetamide (0.18 mL, 0.74 mmol) and acetonitrile (1.5 mL) and stirring the mixture at 25° C. for 60 minutes, and the resulting mixture was further stirred at 0° C. for 6 hours (starting material:target compound=1:33 (Analytical condition 3)). The obtained reaction mixture was diluted with ethyl acetate (10 mL), and successively washed with a saturated aqueous sodium hydrogen carbonate solution (8.0 mL), 1M hydrochloric acid (8.0 mL), water (10 mL) and a saturated aqueous sodium chloride solution (10 mL). The collected organic layer was concentrated to obtain Fmoc-(Me)βAla-MePhe-OH (0.16 g, yield: 107%) as a white solid.

Synthetic Example 136: Synthesis of Fmoc-MeGABA-MePhe-OH

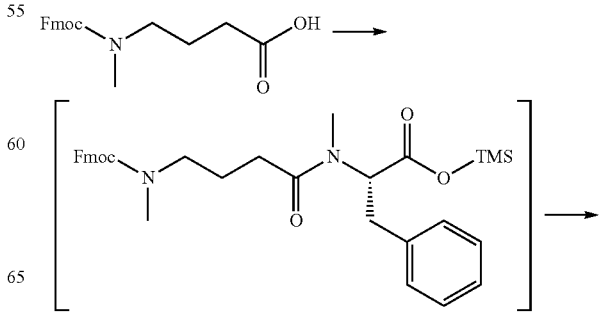

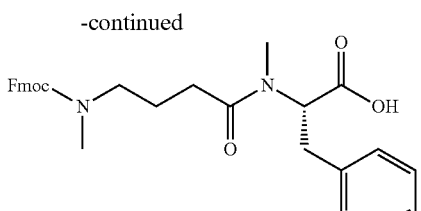

Fmoc-MeGABA-OH (1.0 g, 3.0 mmol) was mixed with tetrahydrofuran (15 mL), triethylamine (0.50 mL, 3.5 mmol) and 2-(4,4-dimethylpentan-2-yl)-5,7,7-trimethyloctanoyl chloride (1.2 g, 3.2 mmol) were added to the mixture at 0° C. and the resulting mixture was stirred for 1 hour. To the solution was added a solution which had been separately prepared by mixing H-MePhe-OH (0.63 g, 3.5 mmol), N,O-bis(trimethylsilyl)acetamide (1.7 mL, 7.1 mmol) and acetonitrile (15 mL) and stirring the mixture at 25° C. for 60 minutes, and the resulting mixture was further stirred at 0° C. for 3 hours (starting material:target compound=1:48 (Analytical condition 3)). The obtained reaction mixture was diluted with ethyl acetate (40 mL), and successively washed with water (15 mL) and a saturated aqueous sodium chloride solution (15 mL). The collected organic layer was concentrated, and the concentrate was purified by column chromatography to obtain Fmoc-MeGABA-MePhe-OH (1.3 g, yield: 88%) as a white solid.

Synthetic Example 137: Synthesis of Fmoc-MeGABA-MePhe-OH

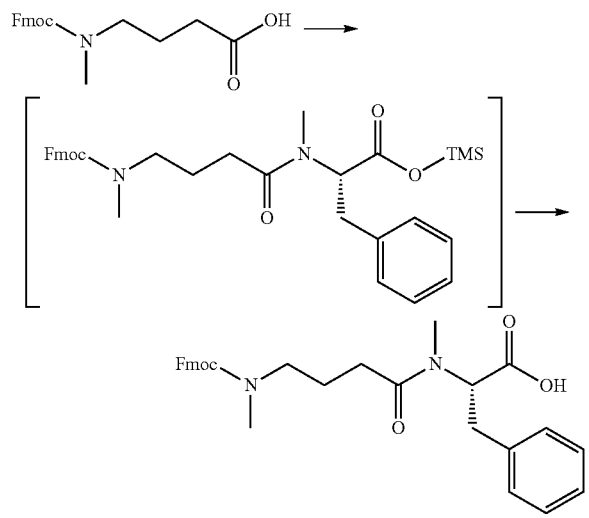

Fmoc-MeGABA-OH (0.10 g, 0.30 mmol) was mixed with tetrahydrofuran (1.5 mL), triethylamine (0.049 mL, 0.35 mmol) and pivaloyl chloride (0.040 mL, 0.32 mmol) were added to the mixture at 0° C. and the resulting mixture was stirred for 1 hour. To the solution was added a solution which had been separately prepared by mixing H-MePhe-OH (0.063 g, 0.35 mmol), N,O-bis(trimethylsilyl)acetamide (0.17 mL, 0.71 mmol) and acetonitrile (1.5 mL) and stirring the mixture at 25° C. for 60 minutes, and the resulting mixture was further stirred at 0° C. for 6 hours (starting material:target compound=1:12 (Analytical condition 3)). The obtained reaction mixture was diluted with ethyl acetate (10 mL), and successively washed with a saturated aqueous sodium hydrogen carbonate solution (8.0 mL), 1M hydrochloric acid (8.0 mL), water (10 mL) and a saturated aqueous sodium chloride solution (10 mL). The collected organic layer was concentrated to obtain Fmoc-MeGABA-MePhe-OH (0.15 g, yield: 105%) as a white solid.

Synthetic Example 138: Synthesis of Fmoc-(2SMe)βAla-(Me)βAla-OH

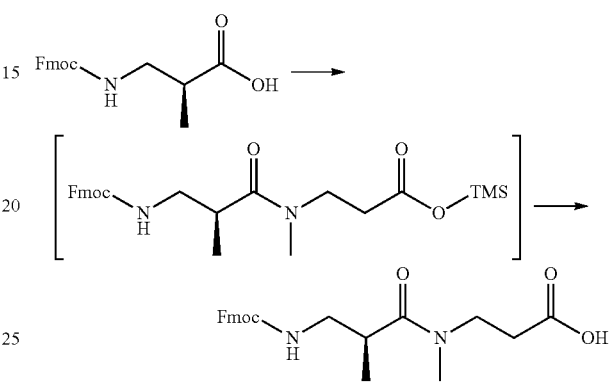

Fmoc-(2SMe)βAla-OH (0.050 g, 0.15 mmol) was mixed with tetrahydrofuran (0.42 mL), triethylamine (0.026 mL, 0.18 mmol) and 2-(4,4-dimethylpentan-2-yl)-5,7,7-trimethyloctanoyl chloride (0.051 g, 0.17 mmol) were added to the mixture at 0° C. and the resulting mixture was stirred for 1 hour. To the solution was added a solution which had been separately prepared by mixing H-(Me)βAla-OH hydrochloride (0.026 g, 0.18 mmol), N,O-bis(trimethylsilyl)acetamide (0.18 mL, 0.74 mmol) and acetonitrile (0.84 mL) and stirring the mixture at 25° C. for 60 minutes, and the resulting mixture was further stirred at 25° C. for 2 hours (starting material:target compound=1:7 (Analytical condition 3)). The obtained reaction mixture was diluted with acetonitrile (6.0 mL), and washed with hexane (8.0 mL). The obtained acetonitrile solution was diluted with ethyl acetate (8.0 mL), and successively washed with a saturated aqueous sodium hydrogen carbonate solution (8.0 mL), a 10% aqueous citric acid solution (8.0 mL), water (10 mL) and a saturated aqueous sodium chloride solution (10 mL). The obtained organic layer was concentrated to obtain Fmoc-(2SMe)βAla-(Me)βAla-OH (0.069 g, yield: 109%) as a colorless oil.

Synthetic Example 139: Synthesis of Fmoc-(2SMe)βAla-(Me)βAla-OH

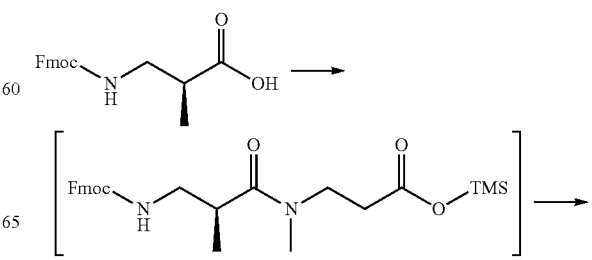

-continued

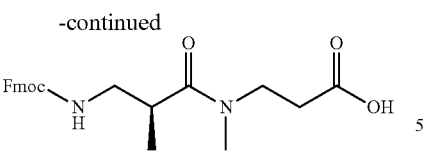

Fmoc-(2SMe)βAla-OH (0.050 g, 0.15 mmol) was mixed with tetrahydrofuran (0.42 mL), triethylamine (0.026 mL, 0.18 mmol) and pivaloyl chloride (0.021 mL, 0.17 mmol) were added to the mixture at 0° C. and the resulting mixture was stirred for 1 hour. To the solution was added a solution which had been separately prepared by mixing H-(Me)βAla-OH hydrochloride (0.026 g, 0.18 mmol), N,O-bis(trimethylsilyl)-acetamide (0.18 mL, 0.74 mmol) and acetonitrile (0.84 mL) and stirring the mixture at 25° C. for 60 minutes, and the resulting mixture was further stirred at 25° C. for 2 hours (starting material:target compound=1:3 (Analytical condition 3)). The obtained reaction mixture was diluted with acetonitrile (6.0 mL), and washed with hexane (8.0 mL). The obtained acetonitrile solution was diluted with ethyl acetate (8.0 mL), and successively washed with a saturated aqueous sodium hydrogen carbonate solution (8.0 mL), a 10% aqueous citric acid solution (8.0 mL), water (10 mL) and a saturated aqueous sodium chloride solution (10 mL). The obtained organic layer was concentrated to obtain Fmoc-(2SMe)βAla-(Me)βAla-OH (0.070 g, yield: 110%) as a colorless oil.

Synthetic Example 140: Synthesis of Fmoc-GABA-(Me)βAla-OH

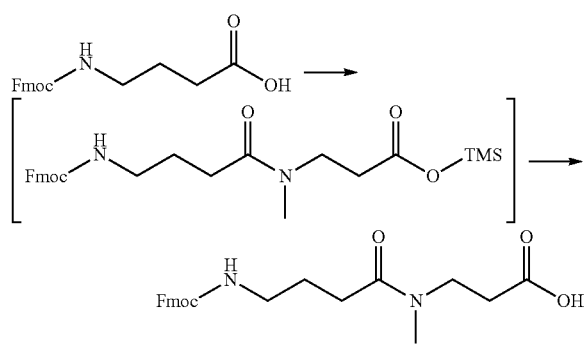

Fmoc-GABA-OH (0.10 g, 0.31 mmol) was mixed with tetrahydrofuran (1.5 mL), triethylamine (0.051 mL, 0.37 mmol) and 2-(4,4-dimethylpentan-2-yl)-5,7,7-trimethyloctanoyl chloride (0.12 g, 0.34 mmol) were added to the mixture at 0° C. and the resulting mixture was stirred for 1 hour. To the solution was added a solution which had been separately prepared by mixing H-(Me)βAla-OH hydrochloride (0.052 g, 0.37 mmol), N,O-bis(trimethylsilyl)acetamide (0.36 mL, 1.5 mmol) and acetonitrile (1.5 mL) and stirring the mixture at 25° C. for 60 minutes, and the resulting mixture was further stirred at 0° C. for 15 hours (starting material:target compound=1:99 (Analytical condition 3)). The obtained reaction mixture was diluted with acetonitrile (6.0 mL), and washed with hexane (10 mL). The obtained acetonitrile solution was diluted with ethyl acetate (10 mL), and successively washed with 1M hydrochloric acid (8.0 mL), water (10 mL) and a saturated aqueous sodium chloride solution (10 mL). The obtained organic layer was concentrated to obtain Fmoc-GABA-(Me)βAla-OH (0.14 g, yield: 108%) as a colorless oil.

Synthetic Example 141: Synthesis of Fmoc-GABA-(Me)βAla-OH

Fmoc-GABA-OH (0.10 g, 0.31 mmol) was mixed with tetrahydrofuran (1.5 mL), triethylamine (0.051 mL, 0.37 mmol) and pivaloyl chloride (0.042 mL, 0.34 mmol) were added to the mixture at 0° C. and the resulting mixture was stirred for 1 hour. To the solution was added a solution which had been separately prepared by mixing H-(Me)βAla-OH hydrochloride (0.052 g, 0.37 mmol), N,O-bis(trimethylsilyl)-acetamide (0.36 mL, 1.5 mmol) and acetonitrile (1.5 mL) and stirring the mixture at 25° C. for 60 minutes, and the resulting mixture was further stirred at 0° C. for 15 hours (starting material:target compound=1:49 (Analytical condition 3)). The obtained reaction mixture was diluted with acetonitrile (8.0 mL), and washed with hexane (15 mL). The obtained acetonitrile solution was diluted with ethyl acetate (10 mL), and successively washed with 1M hydrochloric acid (8.0 mL), water (10 mL) and a saturated aqueous sodium chloride solution (10 mL). The obtained organic layer was concentrated to obtain Fmoc-GABA-(Me)βAla-OH (0.13 g, yield: 104%) as a colorless oil.

In the above-mentioned Synthetic Examples, Synthetic Example 118 is Reference Example relating to synthesis of the starting material used in Examples. In addition, Synthetic Examples 98, 100, 102, 104, 106, 108 to 110, 112, 114, 116, 119, 120, 122, 124, 126, 128, 132, 134, 136, 138 and 140 are Examples of the invention relating to the method for producing the peptide of the present application, Synthetic Examples 97, 99, 101, 103, 105, 107, 111, 113, 115, 117, 121, 123, 125, 127, 129, 133, 135, 137, 139 and 141 are Comparative Examples thereof, and Synthetic Examples 130 and 131 are Reference Examples.

The invention claimed is:

1. A method for producing a peptide which comprises the following Steps (1) to (3):

(1) a step of mixing an N-terminal protected amino acid or an N-terminal protected peptide represented by the formula (I) P-A$^1$-OH wherein P is an N-terminal protective group, and A$^1$ represents a group derived from an amino acid, a group derived from an N—C$_{1-6}$ alkylamino acid, where the C$_{1-6}$ alkyl may have a substituent(s), or a group derived from a peptide, with an activating agent represented by the formula (II)

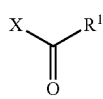

wherein X represents a halogen atom, and $R^1$ represents a secondary $C_{5-40}$ alkyl group which may have a substituent(s);

(2) a step of mixing an amino acid or a peptide represented by the formula (IV): $H-A^2-OH$ wherein $A^2$ represents a group derived from an $N-C_{1-6}$ alkylamino acid, where the $C_{1-6}$ alkyl may have a substituent(s), or a group derived from a 4- to 6-membered cyclic secondary amino acid, where the 4- to 6-membered ring may be fused with a cyclic compound selected from the group consisting of a $C_{6-14}$ aryl ring, a $C_{6-14}$ haloaryl ring and a $C_{3-8}$ cycloalkyl ring, or a group derived from a peptide in which the N-terminal residue is an $N-C_{1-6}$ alkylamino acid, where the $C_{1-6}$ alkyl may have a substituent(s), or a 4- to 6-membered cyclic secondary amino acid, where the 4- to 6-membered ring may be fused with a cyclic compound selected from the group consisting of a $C_{6-14}$ aryl ring, a $C_{6-14}$ haloaryl ring and a $C_{3-8}$ cycloalkyl ring, with a silylating agent; and (3) a step of mixing a product obtained in Step (1) and a product obtained in Step (2).

2. The method for producing a peptide of claim 1, which comprises the following Steps (1) to (3):

(1) a step of mixing an N-terminal protected amino acid represented by the formula (I): $P-A^1-OH$ wherein P is an N-terminal protective group, and $A^1$ represents a group derived from an amino acid or a group derived from an $N-C_{1-6}$ alkylamino acid, where the $C_{1-6}$ alkyl may have a substituent(s), with an activating agent represented by the formula (II):

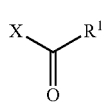

wherein X represents a halogen atom, and $R^1$ represents a secondary $C_{5-40}$ alkyl group which may have a substituent(s);

(2) a step of mixing an amino acid or a peptide represented by the formula (IV): $H-A^2-OH$ wherein $A^2$ represents a group derived from an N-methylamino acid, a group derived from an $N-C_{1-6}$ alkylglycine, where the $C_{1-6}$ alkyl may have a substituent(s), or a group derived from a 4- to 6-membered cyclic secondary amino acid, or a group derived from a peptide in which the N-terminal residue is an N-methylamino acid, an $N-C_{1-6}$ alkylglycine, where the $C_{1-6}$ alkyl may have a substituent(s), or a 4- to 6-membered cyclic secondary amino acid, with a silylating agent; and (3) a step of mixing a product obtained in Step (1) and a product obtained in Step (2).

3. The method for producing a peptide of claim 1, which comprises the following Steps (1) to (3):

(1) a step of mixing an N-terminal protected peptide represented by the formula (V): $P-A^3-OH$ wherein P is an N-terminal protective group, and $A^3$ represents a group derived from a peptide, with an activating agent represented by the formula (II)

wherein X represents a halogen atom, and $R^1$ represents a secondary $C_{5-40}$ alkyl group which may have a substituent(s);

(2) a step of mixing an amino acid represented by the formula (IV'): $H-A^{2'}-OH$ wherein $A^{2'}$ represents a group derived from an N-methylamino acid, a group derived from an $N-C_{1-6}$ alkylglycine, where the $C_{1-6}$ alkyl may have a substituent(s), or a group derived from a 4- to 6-membered cyclic secondary amino acid, with a silylating agent; and (3) a step of mixing a product obtained in Step (1) and a product obtained in Step (2).

4. The method for producing a peptide according to any one of claims 1 to 3, which comprises a step of removing the protective group of the N-terminal of the peptide obtained in Step (3).

5. The method for producing a peptide according to any one of claims 1 to 3, which further comprises repeating one or more times of the following Steps (4) and (5):

(4) a step of removing the protective group of the N-terminal of the peptide obtained in Step (3) or (5);

(5) a step of reacting an N-terminal protected amino acid or an N-terminal protected peptide with the N-terminal of the peptide obtained in Step (4).

6. The method for producing a peptide according to claim 1 or 3, wherein the amino acid positioned at the C-terminal in the N-terminal protected peptide represented by the formula (I): $P-A^1-OH$ or the formula (V): $P-A^3-OH$ wherein P is an N-terminal protective group, and $A^1$ and $A^3$ each represent a group derived from a peptide, is an amino acid other than the $N-C_{1-6}$ alkylamino acid, where the $C_{1-6}$ alkyl may have a substituent(s), or a 4- to 6-membered cyclic secondary amino acid, where the 4- to 6-membered ring may be fused with a cyclic compound selected from the group consisting of a $C_{6-14}$ aryl ring, a $C_{6-14}$ haloaryl ring and a $C_{3-8}$ cycloalkyl ring.

7. The method for producing a peptide according to claim 1 or 2, wherein $A^1$ is a group derived from an amino acid.

8. The method for producing a peptide according to claim 1 or 2, wherein the N-terminal protected amino acid represented by the formula (I) or the amino acid positioned at the C-terminal in the N-terminal protected peptide represented by the formula (I) is an α-amino acid, a β-amino acid or a γ-amino acid.

9. The method for producing a peptide according to claim 8, wherein the N-terminal protected amino acid represented by the formula (I) or the amino acid positioned at the C-terminal in the N-terminal protected peptide represented by the formula (I) is an α-amino acid.

10. The method for producing a peptide according to claim 1, wherein the amino acid represented by the formula (IV) or the amino acid positioned at the N-terminal in the peptide represented by the formula (IV) is an N—$C_{1-6}$ alkyl-α-amino acid, where the $C_{1-6}$ alkyl may have a substituent(s), or a 4- to 6-membered cyclic secondary-α-amino acid.

11. The method for producing a peptide according to claim 1, wherein the amino acid represented by the formula (IV) or the amino acid positioned at the N-terminal in the peptide represented by the formula (IV) is an N-methyl-α-amino acid or an N-ethyl-α-amino acid, where N-methyl and N-ethyl each may have a substituent(s), or a 4- to 6-membered cyclic secondary-α-amino acid.

12. The method for producing a peptide according to any one of claims 1 to 3, wherein $R^1$ is a secondary $C_{5-20}$ alkyl group and X is a chlorine atom.

13. The method for producing a peptide according to any one of claims 1 to 3, wherein the activating agent is

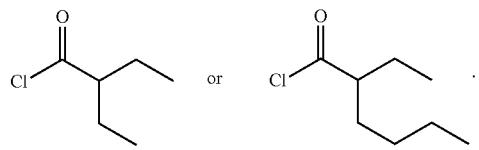

14. The method for producing a peptide according to any one of claims 1 to 3, wherein the activating agent is

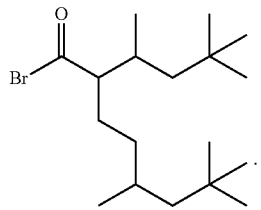

15. The method for producing a peptide according to any one of claims 1 to 3, wherein the activating agent is

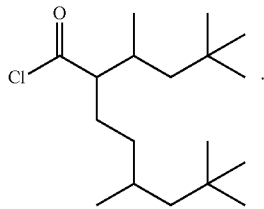 [SMILES: CC(CCC(C(=O)Cl)C(C)CC(C)(C)C)CC(C)(C)C]

16. The method for producing a peptide according to any one of claims 1 to 3, wherein the silylating agent is a trimethylsilylating agent.

17. The method for producing a peptide according to any one of claims 1 to 3, wherein the silylating agent is N,N'-bis(trimethylsilyl)urea or N,O-bis(trimethylsilyl)trifluoroacetamide.

18. The method for producing a peptide according to any one of claims 1 to 3, wherein the silylating agent is N,O-bis(trimethylsilyl)acetamide.

19. The method for producing a peptide according to claim 1, wherein the amino acid or peptide represented by the formula (IV) are each an amino acid other than proline or a peptide in which the N-terminal residue is an amino acid residue other than proline.

20. The method for producing a peptide according to claim 3, wherein the amino acid represented by the formula (IV') is an amino acid other than proline.

* * * * *